(12) United States Patent
Zankel et al.

(10) Patent No.: US 7,560,431 B2
(45) Date of Patent: Jul. 14, 2009

(54) METHODS OF INCREASING DELIVERY OF ACTIVE AGENTS TO BRAIN COMPRISING ADMINISTERING RECEPTOR ASSOCIATED PROTEIN (RAP) FRAGMENTS CONJUGATED TO ACTIVE AGENTS

(75) Inventors: Todd Zankel, San Francisco, CA (US); Christopher M. Starr, Sonoma, CA (US); Reinhard Gabathuler, San Rafael, CA (US)

(73) Assignee: Raptor Pharmaceutical Inc., Novato, CA (US)

( * ) Notice: Subject to any disclaimer, the term of this patent is extended or adjusted under 35 U.S.C. 154(b) by 0 days.

(21) Appl. No.: 11/202,566

(22) Filed: Aug. 12, 2005

(65) Prior Publication Data

US 2006/0029609 A1    Feb. 9, 2006

Related U.S. Application Data

(62) Division of application No. 10/600,862, filed on Jun. 20, 2003, now abandoned.

(51) Int. Cl.
| | |
|---|---|
| A61K 38/18 | (2006.01) |
| C07K 19/00 | (2006.01) |
| C07K 14/435 | (2006.01) |
| C07K 14/48 | (2006.01) |
| C07K 14/485 | (2006.01) |
| C07K 14/50 | (2006.01) |

(52) U.S. Cl. ..................................... 514/12
(58) Field of Classification Search .................. None
See application file for complete search history.

(56) References Cited

U.S. PATENT DOCUMENTS

| | | | |
|---|---|---|---|
| 4,018,884 A | 4/1977 | Cleeland, Jr. et al. | |
| 4,391,904 A | 7/1983 | Litman et al. | |
| 4,394,448 A | 7/1983 | Szoka, Jr. et al. | |
| 4,744,981 A | 5/1988 | Pavanasasivam | |
| 4,897,255 A | 1/1990 | Fritzberg et al. | |
| 4,988,496 A | 1/1991 | Srinivasan et al. | |
| 5,106,951 A | 4/1992 | Morgan, Jr. et al. | |
| 5,186,941 A | 2/1993 | Callahan et al. | |
| 5,474,766 A | 12/1995 | Schwartz et al. | |
| 5,604,198 A * | 2/1997 | Poduslo et al. ............ | 514/6 |
| 5,650,391 A | 7/1997 | Schwartz et al. | |
| 5,962,012 A | 10/1999 | Lin et al. | |
| 5,962,266 A | 10/1999 | White et al. | |
| 5,981,194 A * | 11/1999 | Jefferies et al. ............ | 435/7.1 |
| 6,072,041 A | 6/2000 | Davis et al. | |
| 6,165,476 A | 12/2000 | Strom et al. | |
| 6,261,595 B1 | 7/2001 | Stanley et al. | |
| 6,447,775 B1 | 9/2002 | Strickland et al. | |
| 7,122,353 B2 * | 10/2006 | Shen ...................... | 435/69.7 |

2003/0129186 A1 *  7/2003  Beliveau et al.

FOREIGN PATENT DOCUMENTS

| | | |
|---|---|---|
| WO | 00/71714 | * 11/2000 |
| WO | WO 01/59459 A2 | 8/2001 |
| WO | WO 02/13843 A2 | 2/2002 |
| WO | WO 03/009815 | * 2/2003 |

OTHER PUBLICATIONS

Pardridge 2002. Nature Reviews Drug Discovery 1:131-139.*
Dehouck 1997. Journal of Cell Biology 138:877-889.*
Neels 1999. Journal of Biological Chemistry 274:31305-31311.*
Albeck 1997. Neuroreport 8:2293-2298.*
Altschul et al., "Basic Local Alignment Search Tool," *J. Mol. Biol.*, 215(3):403-410 (1990).
Ashcom et al., "The Human α2-Macroglobulin Receptor: Identification of A 420-kD Cell Surface Glycoprotein Specific for the Activated Conformation of α2-Macroglobulin," *J. Cell. Biol.*, 110(4):1041-1048 (1990).
Bickel et al., "Delivery of Peptides and Proteins Through the Blood-brain Barrier," *Adv. Drug Deliv. Rev.*, 46(1-3):247-279 (2001).
Bickel et al., "Pharmacologic Effects in Vivo in Brain by Vector-mediated Peptide Drug Delivery," *Proc. Natl. Acad. Sci. USA*, 90:2618-2622 (1993).
Blair et al., "Linkage of Cytotoxic Agents to Immunoglobulins," *J. Immunol. Methods*, 59(2):129-143 (1983).
Blattler et al., "New Heterobifunctional Protein Cross-linking Reagent that Forms an Acid-labile Link," *Biochem.*, 24:1517-1524 (1985).
Bu et al., "RAP, a Novel Type of ER Chaperone," *Trends Cell Biol.*, 8(7):272-276 (1998).
Bu et al., "Receptor-associated Protein is a Folding Chaperone for Low Density Lipoprotein Receptor-related Protein," *J. Biol. Chem.*, 271(36):22218-22224 (1996).
Czekay et al., "Endocytic Trafficking of Megalin/RAP Complexes: Dissociation of the Complexes in Late Endosomes," *Mol. Biol. Cell.*, 8(3):517-532 (1997).
Dehouck et al., "A New Function for the LDL Receptor: Transcytosis of LDL Across the Blood-brain Barrier," *J. Cell Biol.*, 138(4):877-889 (1997).

(Continued)

*Primary Examiner*—Daniel E. Kolker
(74) *Attorney, Agent, or Firm*—Marshall, Gerstein & Borun LLP

(57) ABSTRACT

This invention provides compounds of conjugates of therapeutic or active agents with RAP or a RAP polypeptide, their pharmaceutical compositions and methods for using the such compounds and compositions in the diagnosis, prophylaxis, or treatment of diseases and conditions, including particularly diseases of the central nervous system or lysosomal storage diseases.

12 Claims, 20 Drawing Sheets

OTHER PUBLICATIONS

Fahrlander et al., "Amplifying DNA Probe Signals: A "Christmas Tree" Approach," *Bio/Technology*, 6:1165-1168 (1988).

Feng et al., "Progressive Sequence Alignment as a Prerequisite to Correct Phylogenetic Trees," *J. Mol. Evol.*, 25:351-360 (1987).

Fillebeen et al., "Receptor-mediated Transcytosis of Lactoferrin Through the Blood-brain Barrier," *J. Biol. Chem.*, 274:7011-7017 (1999).

FitzGerald et al., "Pseudomonas Exotoxin-mediated Selection Yields Cells with Altered Expression of Low-density Lipoprotein Receptor-related Protein," *J. Cell. Biol.*, 129(6):1533-1541 (1995).

Genbank Accession No. AAH49517, Printed Apr. 22, 2004.
Genbank Accession No. AAM90301, Printed Apr. 22, 2004.
Genbank Accession No. CAA05085, Printed Apr. 22, 2004.
Genbank Accession No. NP_506187, Printed May 21, 2004.
Genbank Accession No. NP_649950, Printed May 21, 2004.
Genbank Accession No. P30533, Printed Apr. 22, 2004.
Genbank Accession No. Q99068, Printed Apr. 22, 2004.
Genbank Accession No. X13916, printed Apr. 22, 2004.
Genbank Accession No. XP_132029, printed May 21, 2004.
Genbank Accession No. XP_313261, printed May 21, 2004.

Gutierrez et al., "Murine Tumor Necrosis Factor Alpha is Transported from Blood to Brain in the Mouse," *J. Neuroimmunology*, 47(2):169-176 (1993).

Henikoff et al., "Amino Acid Substitution Matrices from Protein Blocks," *Proc. Natl. Acad. Sci. USA*, 89:10915-10919 (1989).

Herz et al., "39-kDa Protein Modulates Binding of Ligands to Low Density Lipoprotein Receptor-related Protein/α2-Marcoglobulin Receptor," *J. Biol. Chem.*, 266(32):21232-21238 (1991).

Herz et al., "Gene Transfer and Disruption Strategies to Elucidate Hepatic Lipoprotein Receptor Functions," *Atherosclerosis*, 118 SUppl:S37-S41 (1995).

Herz et al., "LRP: A Multifunctional Scavenger and Signaling Receptor," *J. Clin. Invest.*, 108(6):779-784 (2001).

Higgins et al., "Fast and Sensitive Multiple Sequence Alignments on a Microcomputer," *Comput. Appl. Biosco.*, 5(2):151-153 (1989).

Hoogerbrugge et al., "Allogeneic Bone Marrow Transplantation for Lysosomal Storage Diseases," *Lancet*, 345(8962):1398-1402 (1995).

Jensen et al., "Purification of the Human Placental α-2-Macroglobulin Receptor," *FEBS Lett.*, 255(2):275-280 (1989).

Karlin et al., "Applications and Statistics for Multiple High-Scoring Segments in Molecular Sequences," *Proc. Natl. Acad. Sci. USA*, 90(12):5873-5877 (1993).

Kilic et al., "Intravenous TAT-GDNF is Protective after Focal Cerebral Ischemia in Mice," *Stroke*, 34(5):1304-1310 (2003).

King et al., "Preparation of Protein Conjugates via Intermolecular Hydrazone Linkage," *Biochem.*, 25(19):5774-5779 (1986).

Kusuhara et al., "Efflux Transport Systems for Drugs at the Blood-brain Barrier and Blood-cerebrospinal Fluid Barrier (Part 1)," *Drug Discov. Today*, 6(3):150-156 (2001).

Lin et al., "GDNF: A Glial Cell Line-derived Neurotrohpic Factor for Midbrain Dopaminergic Neurons," *Science*, 260(5111):1130-1132 (1993).

Lisi et al., "Preferential Megalin-mediated Transcytosis of Low-hormonogenic Thyroglobulin: a Control Mechanism for Thyroid Hormone Release," *Proc. Natl. Acad. Sci. USA*, 100(25):14858-14863 (2003).

Medved et al., "Domain Organizatioin of the 39-kDa Receptor-assoicated Protein," *J. biol. Chem.*, 274(2):717-727 (1999).

Meilinger et al., "Removal of Lactoferrin From Plasma is Mediated by Binding to Low Density Lipoprotein Receptor-related Protein/α2-Macroglobulin Receptor and Transport to Endosomes," *FEBS Lett.*, 360(1):70-74 (1995).

Melman et al., "High Affinity Binding of Receptor-associated Protein to Heparin and Low Density Lipoprotein Receptor-related Protein Required Similar Basic Amino Acid Sequence Motifs," *J. Biol. Chem.*, 276(31):29338-29346 (2001).

Needleman et al., "A General Method Applicable to the Search for Similarities in teh Amino Acid Sequence of Two Proteins," *J. Mol. Biol.*, 48(3):443-453 (1970).

Nielsen et al., "The Solution Structure of the N-terminal Domain of α2-Macroglobulin Receptor-associated Protein," *Proc. Natl. Avad. Sci. USA*, 94(14):7521-7525 (1997).

Orlando et al., "Functional Domains of the Receptor-associated Protein (RAP)," *Proc. Natl. Acad. Sci. USA*, 91(8):3161-3165 (1994).

Pardridge, "Blood-brain Barrier Biology and Methodology," *J. Neurovirol.*, 5(6):556-569 (1999).

Pearson et al., "Improved Tools for Biological Sequence Comparison," *Proc. Natl. Acad. Sci. USA*, 85(8):2444-2448 (1988).

Rall et al., "The Domain Structure of Human Receptor-associated Protein," *J. Biol. Chem.*, 273(37):24152-24157 (1998).

Savonen et al., "The Carboxyl-terminal Domain of Receptor-associated Protein Facilitates Proper Folding and Trafficking of the Very Low Density Lipoprotein Receptor by Interaction with the Three Amino-terminal Ligand-binding Repeats of the Receptor," *J. Biol. Chem.*, 274(36):25877-25882 (1999).

Smith et al., "Comparison of Biosequences," *Adv. Appl. Math.*, 2:482-489 (1981).

Srinivasachar et al., "New Protein Cross-linking Reagents that are Cleaved by Mild Acid," *Biochem.*, 28(6):2501-2509 (1989).

Swiss-Prot Primary Accession No. Q07954, printed Apr. 22, 2004.

Takahashi et al., "Rabbit Very Low Density Lipoprotein Receptor: A Low Density Lipoprotein Receptor-like Protein with Distinct Ligand Specificity," *Proc. Natl. Acad. Sci. USA*, 89(19):9252-9256 (1992).

Thompson et al., "Clustal W: Improving the Sensitivity of Progressive Multiple Sequence Alignment Through Sequence Weighting, Position-specific Gap Penalties and Weight Matrix Choice," *Nucleic Acids Res.*, 22(22):4673-4680 (1994).

Tsuji et al., "Carrier-mediated or Specialized Transport of Drugs Across the Blood-brain Barrier," *Adv. Drug Deliv. Rev.*, 36(2-3):277-290 (1999).

Warshawsky et al., "Binding Analysis of Amino-terminal and Carboxyl-terminal Regions of the 39-kDa Protein to the Low Density Lipoprotein Receptor-related Protein," *J. Biol. Chem.*, 269(5):3325-3330 (1994).

Wilchek et al., "The Avidin-Biotin Complex in Bioanalytical Applications," *Anal. Biochem.*, 171:1-32 (1988).

Williams et al., "A Novel Mechanism for Controlling the Activity of α-2-Macroglobulin Receptor/Low Density Lipoprotein Receptor-related Protein," *J. Biol. Chem.*, 267(13):9035-9040 (1992).

Willnow et al., "Low Density Lipoprotein Receptor-related Protein and gp330 Bind Similar Ligands, Including Plasminogen Activator-inhibitor Complexes and Lactoferrin, and Inhibitor of Chylomicron Remnant Clearance," *J. Biol. Chem.*, 267(36):26172-26180 (1992).

Wisselaar et al., "Structural and Functional Changes of Lysosomal Acid α-Glucosidase During Intracellular Transport and Maturation," *J. Biol. Chem.*, 268(3):2223-2231 (1993).

Yenofsky et al., "A Mutant Neomycin Phosphotransferase II Gene Reduces the Resistance of Transformants to Antibiotic Selection Pressure," *Proc. Natl. Acad. Sci. USA*, 87(9):3435-3439 (1990).

Zlokovic et al., "Glycoprotein 330/megalin: Probable Role in Receptor-mediated Transport of Apolipoprotein J Alone and in a Complex with Alzheimer Disease Amyloid Beta at the Blood-brain and Blood-cerebrospinal Fluid Barriers," *Proc. Natl. Acad. Sci. USA*, 93:4229-4234 (1996).

Anderson et al., "Differential Binding of Ligands to the Apolipoprotein E Receptor 2," *Biochemistry*, 42:9355-9364 (2003).

Anderson et al., "Dominant Thermodynamic Role of the Third Independent Receptor Binding Site in the Receptor-Associated Protein RAP," *Biochemistry*, 40:15408-15417 (2001).

Anderson et al., "Identification of the Minimal Functional Unit in the Low Density Lipoprotein Receptor-related Protein for Binding the Receptor-associated Protein (RAP)," *J. Biol. Chem.*, 275(28):21017-21024 (2000).

Bajari et al., "A Minimal Binding Domain of the Low Density Lipoprotein Receptor Family," *Biol. Chem.*, 379:1053-1062 (1998).

Bogan et al., "Anatomy of Hot Spots in Protein Interfaces," *J. Mol. Biol.*, 280:1-9 (1998).

Bu, "The Roles of Receptor-Associated Protein (RAP) as a Molecular Chaperone for Members of the LDL Receptor Family," *Int. Rev. Cytol.*, 209:79-116 (2001).

Clackson et al., "A Hot Spot of Binding Energy in a Hormone-receptor Interface," *Science*, 267:383-386 (1995).

DeLano, "Unraveling Hot Spots in Binding Interfaces: Progress and Challenges," *Curr. Opin. Struct. Biol.*, 12:14-20 (2002).

Dwyer et al., "High Affinity RNase S-Peptide Variants Obtained by Phage Display Have a Novel Hot Spot of Binding Energy," *Biochemistry*, 40:13491-13500 (2001).

Fisher et al., "Structure of an LDLR-RAP Complex Reveals a General Mode for Ligand Recognition by Lipoprotein Receptors," *Molecular Cell*, 22:277-283 (2006).

Gao et al., "Structure-based Method for Analyzing Protein-Protein Interfaces," *J. Mol. Model*, 10:4-54 (2004).

Halperin et al., "Protein-Protein Interactions: Coupling of Structurally Conserved Residues and of Hot Spots Across Interfaces. Implications for Docking," *Structure*, 12:1027-1038 (2004).

Horn et al., "Molecular Analysis of Ligand Binding to the Second Cluster of Complement-type Repeats of the Low Density Lipoprotein Receptor-related Protein," *J. Biol. Chem.*, 272(21):13608-13613 (1997).

Jensen et al., "Binding Site Structure of One LRP-RAP Complex: Implications for a Common Ligand-Receptor Binding Motif," *J. Mol. Biol.*, 362:700-716 (2006).

Kounnas et al., "The 39-kDa Receptor-Associated Protein Interacts with Two Members of the Low Density Lipoprotein Receptor Family, 2-Macroglobulin Receptor and Glycoprotein 330," *J. Biol. Chem.*, 267(29):21162-21166 (1992).

Lee et al., "RAP uses a histidine switch to regulate its interaction with LRP in the ER and Golgi," *Mol. Cell*, 22:423-430 (2006).

Li et al., "Magnitude of the Hydrophobic Effect at Central Versus Peripheral Sites in Protein-Protein Interfaces," *Structure*, 13:297-307 (2005).

Mazumder et al., "Translational Control by the 3'-UTR: The Ends Specify the Means," *Trends in Biochemical Sciences*, 28:91-98 (2003).

McCormick et al., "Independent and Cooperative Roles of N-Glycans and Molecular Chaperones in the Folding and Disulfide Bond Formation of the Low-Density Lipoprotein (LDL) Receptor-Related Protein," *Biochemistry*, 44:5794-5803 (2005).

Migliorini et al., "Allosteric Modulation of Ligand Binding to Low Density Lipoprotein Receptor-related Protein by the Receptor-associated Protein Requires Critical Lysine Residues within its Carboxyl-terminal Domain," *J. Biol. Chem.*, 278(20):17986-17992 (2003).

Neels et al., "The Second and Fourth Cluster of Class a Cysteine-rich Repeats of the Low Density Lipoprotein Receptor-related Protein Share Ligand-binding Properties," *J. Biol. Chem.*, 274(44):31305-31311 (1999).

Obermoeller et al., "Differential Functions of Triplicated Repeats Suggest Two Independent Roles for the Receptor-Associated Protein as a Molecular Chaperone," *J. Biol. Chem.*, 272(16):10761-10768 (1997).

Prince et al., "Lipoprotein Receptor Binding, Cellular Uptake, and Lysosomal Delivery of Fusions Between the Receptor-Associated Protein (RAP) and -L-Iduronidase or Acid -Glucosidase," *J. Biol. Chem.*, 279(33):35037-35046 (2004).

Reddy, "Controlled-released, Pegylation, Liposomal Formulations: New Mechanisms in the Delivery of Injectable Drugs," *Annals of Pharmacology*, 34:915-923 (2000).

Russell et al., "Recombinant Proteins for Genetic Disease," *Clinical Genetics*, 55:389-394 (1999).

Van den Hout et al., "Recombinant Human α-glucosidase from Rabbit Milk in Pompe Patients," *Lancet*, 356:397-398 (2000).

Canals et al., J. Neuroscience, 24(35):7727-7739 (2004).

Ferrer et al., Brain Research, 866, 257-261 (2000).

Kells et al., Molecular Therapy, 9 (5) 682-688 (2004).

Spires, et al., J. Neuroscience, 24(9) 2270-2276 (2004).

Zuccato et al., Science, 293, 493-498 (2001).

* cited by examiner

FIGURE 2a. Primers used to obtain sequences high-fidelity PCR amplification of human cDNA.

RAPF:   GCGATAGGATCCTACTCGCGGGAGAAGAACCAGCCCAAGCCGTCCCCGA

RAPR:   GCGATAAACCGGTTTCTGCCTCGGCGCGAGCTCTGGAGATCCTGCCGGACAGGTCCT

GAAF:   GCGATAACCGGTGCACACCCCGGCCGTCCCAGAGCAGTG

GAAR:   GCGATACTCGAGTCAACACCAGCTGACGAGAAACTGC

IDUF:   GCGATAACCGGTGAGGCCCCCCGCACCTGGTGCATGTGGACGCGGC

IDUR:   GCGATACTCGAGTCATGGATTGCCCGGGGATGGGGGCCCTCTTGG

GDNF:   ACAGTGACCGGTTCACCAGATAAACAAATGGCA

GDNR:   ACAGTGCTCGAGTCTAGATCAGATACATCCACACCTTT

FIGURE 2b. GDNF fusion, substitution of RAPF with RAPBACF in RAP amplification of GDNF construct.

RAPBACF: ACAGTGGCCATGGGGGGTTCTTACTCGCGGGAGAAGAACCAGCCCAAGCCG

FIGURE 3. Nucleotide and protein sequences of the RAP-GAA fusion

```
cttaccgccatgcggggtccgagcggggctctgtggctgctcctggctctgcgcaccgtg
          M   R   G   P   S   G   A   L   W   L   L   L   A   L   R   T   V
ctcggatcctactcgcgggagaagaaccagcccaagccgtccccgaaacgcgagtccgga
 L   G   S   Y   S   R   E   K   N   Q   P   K   P   S   P   K   R   E   S   G
gaggagttccgcatggagaagttgaaccagctgtgggagaaggcccagcgactgcatctt
 E   E   F   R   M   E   K   L   N   Q   L   W   E   K   A   Q   R   L   H   L
cctcccgtgaggctggccgagctccacgctgatctgaagatacaggagagggacgaactc
 P   P   V   R   L   A   E   L   H   A   D   L   K   I   Q   E   R   D   E   L
gcctggaagaaactaaagcttgacggcttggacgaagatggggagaaggaagcgagactc
 A   W   K   K   L   K   L   D   G   L   D   E   D   G   E   K   E   A   R   L
atacgcaacctcaatgtcatcttggccaagtatggtctggacggaaagaaggacgctcgg
 I   R   N   L   N   V   I   L   A   K   Y   G   L   D   G   K   K   D   A   R
caggtgaccagcaactccctcagtggcacccaggaagacgggctggatgaccccaggctg
 Q   V   T   S   N   S   L   S   G   T   Q   E   D   G   L   D   D   P   R   L
gaaaagctgtggcacaaggcgaagacctctgggaaattctccggcgaagaactggacaag
 E   K   L   W   H   K   A   K   T   S   G   K   F   S   G   E   E   L   D   K
ctctggcgggagttcctgcatcacaaagagaaagttcacgagtacaacgtcctgctggag
 L   W   R   E   F   L   H   H   K   E   K   V   H   E   Y   N   V   L   L   E
accctgagcaggaccgaagaaatccacgagaacgtcattagcccctcggacctgagcgac
 T   L   S   R   T   E   E   I   H   E   N   V   I   S   P   S   D   L   S   D
atcaagggcagcgtcctgcacagcaggcacacggagctgaaggagaagctgcgcagcatc
 I   K   G   S   V   L   H   S   R   H   T   E   L   K   E   K   L   R   S   I
aaccagggcctggaccgcctgcgcagggtcagccaccagggctacagcactgaggctgag
 N   Q   G   L   D   R   L   R   R   V   S   H   Q   G   Y   S   T   E   A   E
ttcgaggagcccagggtgattgacctgtgggacctggcgcagtccgccaacctcacggac
 F   E   E   P   R   V   I   D   L   W   D   L   A   Q   S   A   N   L   T   D
aaggagctggaggcgttccggagggagctcaagcacttcgaagccaaaatcgagaagcac
 K   E   L   E   A   F   R   E   E   L   K   H   F   E   A   K   I   E   K   H
aaccactaccagaagcagctggagattgcgcacgagaagctgaggcacgcagagagcgtg
 N   H   Y   Q   K   Q   L   E   I   A   H   E   K   L   R   H   A   E   S   V
ggcgacggcgagcgtgtgagccgcagccgcgagaagcacgccctgctggaggggcggacc
 G   D   G   E   R   V   S   R   S   R   E   K   H   A   L   L   E   G   R   T
aaggagctgggctacacggtgaagaagcatctgcaggacctgtccggcaggatctccaga
 K   E   L   G   Y   T   V   K   K   H   L   Q   D   L   S   G   R   I   S   R
gctcgcgccgaggcagaaaccggtgcacaccccggccgtcccagagcagtgcccacacag
 A   R   A   E   A   E   T   G   A   H   P   G   R   P   R   A   V   P   T   Q
tgcgacgtccccccaacagccgcttcgattgcgcccctgacaaggccatcacccaggaa
 C   D   V   P   P   N   S   R   F   D   C   A   P   D   K   A   I   T   Q   E
cagtgcgaggcccgcggctgctgctacatccctgcaaagcaggggctgcagggagcccag
 Q   C   E   A   R   G   C   C   Y   I   P   A   K   Q   G   L   Q   G   A   Q
atggggcagccctggtgcttcttcccacccagctaccccagctacaagctggagaacctg
 M   G   Q   P   W   C   F   F   P   P   S   Y   P   S   Y   K   L   E   N   L
agctcctctgaaatgggctacacggccacccctgacccgtaccaccccaccttcttcccc
 S   S   S   E   M   G   Y   T   A   T   L   T   R   T   T   P   T   F   F   P
aaggacatcctgaccctgcggctggacgtgatgatggagactgagaaccgcctccacttc
 K   D   I   L   T   L   R   L   D   V   M   M   E   T   E   N   R   L   H   F
acgatcaaagatccagctaacaggcgctacgaggtgcccttggagaccccgcgtgtccac
 T   I   K   D   P   A   N   R   R   Y   E   V   P   L   E   T   P   R   V   H
agccgggcaccgtccccactctacagcgtggagttctccgaggagcccttcggggtgatc
 S   R   A   P   S   P   L   Y   S   V   E   F   S   E   E   P   F   G   V   I
gtgcaccggcagctggacggccgcgtgctgctgaacacgacggtggcgcccctgttcttt
 V   H   R   Q   L   D   G   R   V   L   L   N   T   T   V   A   P   L   F   F
gcggaccagttccttcagctgtccacctcgctgccctcgcagtatatcacaggcctcgcc
 A   D   Q   F   L   Q   L   S   T   S   L   P   S   Q   Y   I   T   G   L   A
gagcacctcagtcccctgatgctcagcaccagctggaccaggatcaccctgtggaaccgg
 E   H   L   S   P   L   M   L   S   T   S   W   T   R   I   T   L   W   N   R
gaccttgcgcccacgcccggtgcgaacctctacgggtctcaccctttctacctggcgctg
 D   L   A   P   T   P   G   A   N   L   Y   G   S   H   P   F   Y   L   A   L
gaggacggcgggtcggcacacggggtgttcctgctaaacagcaatgccatggatgtggtc
```

```
           E   D   G   G   S   A   H   G   V   F   L   L   N   S   N   A   M   D   V   V
          ctgcagccgagccctgcccttagctggaggtcgacaggtgggatcctggatgtctacatc
           L   Q   P   S   P   A   L   S   W   R   S   T   G   G   I   L   D   V   Y   I
          ttcctgggcccagagcccaagagcgtggtgcagcagtacctggacgttgtgggataccog
           F   L   G   P   E   P   K   S   V   V   Q   Q   Y   L   D   V   V   G   Y   P
          ttcatgccgccatactggggcctggcttccacctgtgccgctggggctactcctccacc
           F   M   P   P   Y   W   G   L   G   F   H   L   C   R   W   G   Y   S   S   T
          gctatcacccgccaggtggtggagaacatgaccagggcccacttcccccctggacgtccaa
           A   I   T   R   Q   V   V   E   N   M   T   R   A   H   F   P   L   D   V   Q
          tggaacgacctggactacatggactcccggagggacttcacgttcaacaaggatggcttc
           W   N   D   L   D   Y   M   D   S   R   R   D   F   T   F   N   K   D   G   F
          cgggacttccccggccatggtgcaggagctgcaccagggcggccggcgctacatgatgatc
           R   D   F   P   A   M   V   Q   E   L   H   Q   G   G   R   R   Y   M   M   I
          gtggatcctgccatcagcagctcgggcctgccggagctacaggccctacgacgagggt
           V   D   P   A   I   S   S   S   G   P   A   G   S   Y   R   P   Y   D   E   G
          ctgcggaggggggttttcatcaccaacgagaccggccagccgctgattgggaaggtatgg
           L   R   R   G   V   F   I   T   N   E   T   G   Q   P   L   I   G   K   V   W
          cccgggtccactgcccttccccgacttcaccaaccccacagccctggcctggtgggaggac
           P   G   S   T   A   F   P   D   F   T   N   P   T   A   L   A   W   W   E   D
          atggtggctgagttccatgaccaggtgcccttcgacggcttgtggattgacatgaacgag
           M   V   A   E   F   H   D   Q   V   P   F   D   G   L   W   I   D   M   N   E
          ccttccaacttcatcagaggctctgaggacggctgccccaacaatgagctggagaaccca
           P   S   N   F   I   R   G   S   E   D   G   C   P   N   N   E   L   E   N   P
          ccctacgtgcctggggtggttgggggaccctccaggcggccaccatctgtgcctccagc
           P   Y   V   P   G   V   V   G   G   T   L   Q   A   A   T   I   C   A   S   S
          caccagtttctctccacacactacaacctgcacaacctctacggcctgaccgaagccatc
           H   Q   F   L   S   T   H   Y   N   L   H   N   L   Y   G   L   T   E   A   I
          gcctcccacagggcgctggtgaaggctcgggggacacgcccatttgtgatctcccgctcg
           A   S   H   R   A   L   V   K   A   R   G   T   R   P   F   V   I   S   R   S
          acctttgctggccacggccgatacgccggccactggacgggggacgtgtggagctcctgg
           T   F   A   G   H   G   R   Y   A   G   H   W   T   G   D   V   W   S   S   W
          gagcagctcgcctcctccgtgccagaaatcctgcagtttaacctgctgggggtgcctctg
           E   Q   L   A   S   S   V   P   E   I   L   Q   F   N   L   L   G   V   P   L
          gtcggggccgacgtctgcggcttcctgggcaacacctcagaggagctgtgtgtgcgctgg
           V   G   A   D   V   C   G   F   L   G   N   T   S   E   E   L   C   V   R   W
          acccagctgggggccttctaccccttcatgcggaaccacaacagcctgctcagtctgccc
           T   Q   L   G   A   F   Y   P   F   M   R   N   H   N   S   L   L   S   L   P
          caggagccgtacagcttcagcgagccggcccagcaggccatgaggaaggccctcaccctg
           Q   E   P   Y   S   F   S   E   P   A   Q   Q   A   M   R   K   A   L   T   L
          cgctacgcactcctccccccacctctacacactgttccaccaggcccacgtcgcggggggag
           R   Y   A   L   L   P   H   L   Y   T   L   F   H   Q   A   H   V   A   G   E
          accgtggcccggccccttcctggagttccccaaggactctagcacctggactgtggac
           T   V   A   R   P   L   F   L   E   F   P   K   D   S   S   T   W   T   V   D
          caccagctcctgtgggggaggccctgctcatcaccccagtgctccaggccgggaaggcc
           H   Q   L   L   W   G   E   A   L   L   I   T   P   V   L   Q   A   G   K   A
          gaagtgactggctacttccccttgggcacatggtacgacctgcagacggtgccaatagag
           E   V   T   G   Y   F   P   L   G   T   W   Y   D   L   Q   T   V   P   I   E
          gcccttggcagcctcccaccccccacctgcagctccccgtgagccagccatccacagcgag
           A   L   G   S   L   P   P   P   A   A   P   R   E   P   A   I   H   S   E
          gggcagtgggtgacgctgccggccccctggacaccatcaacgtccacctccgggctggg
           G   Q   W   V   T   L   P   A   P   L   D   T   I   N   V   H   L   R   A   G
          tacatcatccccctgcagggccctggcctcacaaccacagagtcccgccagcagcccatg
           Y   I   I   P   L   Q   G   P   G   L   T   T   T   E   S   R   Q   Q   P   M
          gccctggctgtggccctaaccaagggtggagaggcccgaggggagctgttctgggacgat
           A   L   A   V   A   L   T   K   G   G   E   A   R   G   E   L   F   W   D   D
          ggagagagcctggaagtgctggagcgaggggcctacacacaggtcatcttcctggccagg
           G   E   S   L   E   V   L   E   R   G   A   Y   T   Q   V   I   F   L   A   R
          aataacacgatcgtgaatgagctggtacgtgtgaccagtgagggagctggcctgcagctg
           N   N   T   I   V   N   E   L   V   R   V   T   S   E   G   A   G   L   Q   L
          cagaaggtgactgtcctgggcgtggccacggcgccccagcaggtcctctccaacggtgtc
           Q   K   V   T   V   L   G   V   A   T   A   P   Q   Q   V   L   S   N   G   V
```

FIGURE 3 (CONT)

```
cctgtctccaacttcacctacagccccgacaccaaggtcctggacatctgtgtctcgctg
 P   V   S   N   F   T   Y   S   P   D   T   K   V   L   D   I   C   V   S   L
ttgatgggagagcagtttctcgtcagctggtgttgactcgag
 L   M   G   E   Q   F   L   V   S   W   C   -
```

Melanotransferrin signal sequence is italicized. Linker peptide is underlined.

FIGURE 3 (CONT)

FIGURE 4. Nucleotide and protein sequences of the RAP-IDU fusion

```
aagcttaccgccatgcggggtccgagcggggctctgtggctgctcctggctctgcgcacc
              M  R  G  P  S  G  A  L  W  L  L  L  A  L  R  T
gtgctcggatcctactcgcgggagaagaaccagcccaagccgtccccgaaacgcgagtcc
 V  L  G  S  Y  S  R  E  K  N  Q  P  K  P  S  P  K  R  E  S
ggagaggagttccgcatggagaagttgaaccagctgtgggagaaggcccagcgactgcat
 G  E  E  F  R  M  E  K  L  N  Q  L  W  E  K  A  Q  R  L  H
cttcctcccgtgaggctggccgagctccacgctgatctgaagatacaggagagggacgaa
 L  P  P  V  R  L  A  E  L  H  A  D  L  K  I  Q  E  R  D  E
ctcgcctggaagaaactaaagcttgacggcttggacgaagatggggagaaggaagcgaga
 L  A  W  K  K  L  K  L  D  G  L  D  E  D  G  E  K  E  A  R
ctcatacgcaacctcaatgtcatcttggccaagtatggtctggacggaaagaaggacgct
 L  I  R  N  L  N  V  I  L  A  K  Y  G  L  D  G  K  K  D  A
cggcaggtgaccagcaactccctcagtggcacccaggaagacgggctggatgaccccagg
 R  Q  V  T  S  N  S  L  S  G  T  Q  E  D  G  L  D  D  P  R
ctggaaaagctgtggcacaaggcgaagacctctgggaaattctccggcgaagaactggac
 L  E  K  L  W  H  K  A  K  T  S  G  K  F  S  G  E  E  L  D
aagctctggcgggagttcctgcatcacaaagagaaagttcacgagtacaacgtcctgctg
 K  L  W  R  E  F  L  H  H  K  E  K  V  H  E  Y  N  V  L  L
gagaccctgagcaggaccgaagaaatccacgagaacgtcattagcccctcggacctgagc
 E  T  L  S  R  T  E  E  I  H  E  N  V  I  S  P  S  D  L  S
gacatcaagggcagcgtcctgcacagcaggcacacggagctgaaggagaagctgcgcagc
 D  I  K  G  S  V  L  H  S  R  H  T  E  L  K  E  K  L  R  S
atcaaccagggcctggaccgcctgcgcagggtcagccaccagggctacagcactgaggct
 I  N  Q  G  L  D  R  L  R  R  V  S  H  Q  G  Y  S  T  E  A
gagttcgaggagcccagggtgattgacctgtgggacctggcgcagtccgccaacctcacg
 E  F  E  E  P  R  V  I  D  L  W  D  L  A  Q  S  A  N  L  T
gacaaggagctggaggcgttccgggaggagctcaagcacttcgaagccaaaatcgagaag
 D  K  E  L  E  A  F  R  E  E  L  K  H  F  E  A  K  I  E  K
cacaaccactaccagaagcagctggagattgcgcacgagaagctgaggcacgcagagagc
 H  N  H  Y  Q  K  Q  L  E  I  A  H  E  K  L  R  H  A  E  S
gtgggcgacggcgagcgtgtgagccgcagccgagaagcacgccctgctggaggggcgg
 V  G  D  G  E  R  V  S  R  S  R  E  K  H  A  L  L  E  G  R
accaaggagctgggctacacggtgaagaagcatctgcaggacctgtccggcaggatctcc
 T  K  E  L  G  Y  T  V  K  K  H  L  Q  D  L  S  G  R  I  S
agagctcgcgccgaggcagaaaccggtgaggccccgcacctggtgcatgtggacgcggcc
 R  A  R  A  E  A  E  T  G  E  A  P  H  L  V  H  V  D  A  A
           ‾‾‾‾‾‾‾‾‾‾‾‾
cgcgcgctgtggcccctgcggcgcttctggaggagcacaggcttctgccccccgctgcca
 R  A  L  W  P  L  R  R  F  W  R  S  T  G  F  C  P  P  L  P
cacagccaggctgaccagtacgtcctcagctgggaccagcagctcaacctcgcctatgtg
 H  S  Q  A  D  Q  Y  V  L  S  W  D  Q  Q  L  N  L  A  Y  V
ggcgccgtccctcaccgcggcatcaagcaggtccggacccactggctgctggagcttgtc
 G  A  V  P  H  R  G  I  K  Q  V  R  T  H  W  L  L  E  L  V
accaccagggggtccactggacggggcctgagctacaacttcacccacctggacgggtac
 T  T  R  G  S  T  G  R  G  L  S  Y  N  F  T  H  L  D  G  Y
ttggaccttctcagggagaaccagctcctcccagggtttgagctgatgggcagcgcctcg
 L  D  L  L  R  E  N  Q  L  L  P  G  F  E  L  M  G  S  A  S
ggccacttcactgactttgaggacaagcagcaggtgtttgagtggaaggacttggtctcc
 G  H  F  T  D  F  E  D  K  Q  Q  V  F  E  W  K  D  L  V  S
agcctggccaggagatacatcggtaggtacggactggcgcatgtttccaagtggaacttc
 S  L  A  R  R  Y  I  G  R  Y  G  L  A  H  V  S  K  W  N  F
gagacgtggaatgagccagaccaccacgactttgacaacgtctccatgaccatgcaaggc
 E  T  W  N  E  P  D  H  H  D  F  D  N  V  S  M  T  M  Q  G
ttcctgaactactacgatgcctgctcggagggtctgcgcgccgccagccccgccctgcgg
 F  L  N  Y  Y  D  A  C  S  E  G  L  R  A  A  S  P  A  L  R
ctgggaggccccggcgactccttccacacccaccgcgatccccgctgagctggggcctc
 L  G  G  P  G  D  S  F  H  T  P  P  R  S  P  L  S  W  G  L
ctgcgccactgccacgacggtaccaacttcttcactggggaggcgggcgtgcggctggac
 L  R  H  C  H  D  G  T  N  F  F  T  G  E  A  G  V  R  L  D
```

```
tacatctccctccacaggaagggtgcgcgcagctccatctccatcctggagcaggagaag
 Y  I  S  L  H  R  K  G  A  R  S  S  I  S  I  L  E  Q  E  K
gtcgtcgcgcagcagatccggcagctcttccccaagttcgcggacacccccatttacaac
 V  V  A  Q  Q  I  R  Q  L  F  P  K  F  A  D  T  P  I  Y  N
gacgaggcggacccgctggtgggctggtccctgccacagccgtggagggcggacgtgacc
 D  E  A  D  P  L  V  G  W  S  L  P  Q  P  W  R  A  D  V  T
tacgcggccatggtggtgaaggtcatcgcgcagcatcagaacctgctactggccaacacc
 Y  A  A  M  V  V  K  V  I  A  Q  H  Q  N  L  L  A  N  T
acctccgccttcccctacgcgctcctgagcaacgacaatgccttcctgagctaccacccg
 T  S  A  F  P  Y  A  L  L  S  N  D  N  A  F  L  S  Y  H  P
cacccgttcgcgcagcgcacgctcaccgcgcgcttccaggtcaacaacacccgcccgccg
 H  P  F  A  Q  R  T  L  T  A  R  F  Q  V  N  N  T  R  P  P
cacgtgcagctgttgcgcaagccggtgctcacggccatggggctgctggcgctgctggat
 H  V  Q  L  L  R  K  P  V  L  T  A  M  G  L  L  A  L  L  D
gaggagcagctctgggccgaagtgtcgcaggccgggaccgtcctggacagcaaccacacg
 E  E  Q  L  W  A  E  V  S  Q  A  G  T  V  L  D  S  N  H  T
gtgggcgtcctggccagcgcccaccgccccagggcccggccgacgcctggcgcgccgcg
 V  G  V  L  A  S  A  H  R  P  Q  G  P  A  D  A  W  R  A  A
gtgctgatctacgcgagcgacgacacccgcgcccaccccaaccgcagcgtcgcggtgacc
 V  L  I  Y  A  S  D  D  T  R  A  H  P  N  R  S  V  A  V  T
ctgcggctgcgcggggtgccccccggcccgggcctggtctacgtcacgcgctacctggac
 L  R  L  R  G  V  P  P  G  P  G  L  V  Y  V  T  R  Y  L  D
aacgggctctgcagccccgacggcgagtggcggcgcctgggccggcccgtcttccccacg
 N  G  L  C  S  P  D  G  E  W  R  R  L  G  R  P  V  F  P  T
gcagagcagttccggcgcatgcgcgcggctgaggacccggtggccgcggcgccccgcccc
 A  E  Q  F  R  R  M  R  A  A  E  D  P  V  A  A  A  P  R  P
ttacccgccggcggccgcctgaccctgcgccccgcgctgcggctgccgtcgcttttgctg
 L  P  A  G  G  R  L  T  L  R  P  A  L  R  L  P  S  L  L  L
gtgcacgtgtgtgcgcgccccgagaagccgcccgggcaggtcacgcggctccgcgccctg
 V  H  V  C  A  R  P  E  K  P  P  G  Q  V  T  R  L  R  A  L
cccctgacccaagggcagctggttctggtctggtcggatgaacacgtgggctccaagtgc
 P  L  T  Q  G  Q  L  V  L  V  W  S  D  E  H  V  G  S  K  C
ctgtggacatacgagatccagttctctcaggacggtaaggcgtacaccccggtcagcagg
 L  W  T  Y  E  I  Q  F  S  Q  D  G  K  A  Y  T  P  V  S  R
aagccatcgaccttcaacctctttgtgttcagcagacacaggtgctgtctctggctcc
 K  P  S  T  F  N  L  F  V  F  S  P  D  T  G  A  V  S  G  S
taccgagttcgagccctggactactgggcccgaccaggccccttctcggaccctgtgccg
 Y  R  V  R  A  L  D  Y  W  A  R  P  G  P  F  S  D  P  V  P
tacctggaggtccctgtgccaagagggcccccatccccgggcaatccatgactcgag
 Y  L  E  V  P  V  P  R  G  P  P  S  P  G  N  P  -
```

Melanotransferrin signal sequence is italicized. Linker peptide is underlined.

FIGURE 4 (CONT)

FIGURE 5. Nucleotide and protein sequences of the RAP-GDNF fusion

```
atggggggttcttactcgcgggagaagaaccagcccaagccgtccccgaaacgcgagtcc
 M  G  G  S  Y  S  R  E  K  N  Q  P  K  P  S  P  K  R  E  S
ggagaggagttccgcatggagaagttgaaccagctgtgggagaaggcccagcgactgcat
 G  E  E  F  R  M  E  K  L  N  Q  L  W  E  K  A  Q  R  L  H
cttcctcccgtgaggctggccgagctccacgctgatctgaagatacaggagagggacgaa
 L  P  P  V  R  L  A  E  L  H  A  D  L  K  I  Q  E  R  D  E
ctcgcctggaagaaactaaagcttgacggcttggacgaagatggggagaaggaagcgaga
 L  A  W  K  K  L  K  L  D  G  L  D  E  D  G  E  K  E  A  R
ctcatacgcaacctcaatgtcatcttggccaagtatggtctggacggaaagaaggacgct
 L  I  R  N  L  N  V  I  L  A  K  Y  G  L  D  G  K  K  D  A
cggcaggtgaccagcaactccctcagtggcacccaggaagacgggctggatgacccagg
 R  Q  V  T  S  N  S  L  S  G  T  Q  E  D  G  L  D  D  P  R
ctggaaaagctgtggcacaaggcgaagacctctgggaaattctccggcgaagaactggac
 L  E  K  L  W  H  K  A  K  T  S  G  K  F  S  G  E  E  L  D
aagctctggcgggagttcctgcatcacaaagagaaagttcacgagtacaacgtcctgctg
 K  L  W  R  E  F  L  H  H  K  E  K  V  H  E  Y  N  V  L  L
gagaccctgagcaggaccgaagaaatccacgagaacgtcattagcccctcggacctgagc
 E  T  L  S  R  T  E  E  I  H  E  N  V  I  S  P  S  D  L  S
gacatcaagggcagcgtcctgcacagcaggcacacggagctgaaggagaagctgcgcagc
 D  I  K  G  S  V  L  H  S  R  H  T  E  L  K  E  K  L  R  S
atcaaccagggcctggaccgcctgcgcagggtcagccaccagggctacagcactgaggct
 I  N  Q  G  L  D  R  L  R  R  V  S  H  Q  G  Y  S  T  E  A
gagttcgaggagcccagggtgattgacctgtgggacctggcgcagtccgccaacctcacg
 E  F  E  E  P  R  V  I  D  L  W  D  L  A  Q  S  A  N  L  T
gacaaggagctggaggcgttccgggaggagctcaagcacttcgaagccaaaatcgagaag
 D  K  E  L  E  A  F  R  E  E  L  K  H  F  E  A  K  I  E  K
cacaaccactaccagaagcagctggagattgcgcacgagaagctgaggcacgcagagagc
 H  N  H  Y  Q  K  Q  L  E  I  A  H  E  K  L  R  H  A  E  S
gtgggcgacggcgagcgtgtgagccgcagccgcgagaagcacgccctgctggaggggcgg
 V  G  D  G  E  R  V  S  R  S  R  E  K  H  A  L  L  E  G  R
accaaggagctgggctacacggtgaagaagcatctgcaggacctgtccggcaggatctcc
 T  K  E  L  G  Y  T  V  K  K  H  L  Q  D  L  S  G  R  I  S
agagctcgggccgaggcagaaaccggttcaccagataaacaaatggcagtgcttcctaga
 R  A  R  A̲ ̲E̲ ̲A̲ ̲E̲ ̲T̲ ̲G̲  S  P  D  K  Q  M  A  V  L  P  R
agagagcggaatcggcaggctgcagctgccaacccagagaattccagaggaaaaggtcgg
 R  E  R  N  R  Q  A  A  A  A  N  P  E  N  S  R  G  K  G  R
agaggccagaggggcaaaaaccggggttgtgtcttaactgcaatacatttaaatgtcact
 R  G  Q  R  G  K  N  R  G  C  V  L  T  A  I  H  L  N  V  T
gacttgggtctgggctatgaaaccaaggaggaactgattttttaggtactgcagcggctct
 D  L  G  L  G  Y  E  T  K  E  E  L  I  F  R  Y  C  S  G  S
tgcgatgcagctgagacaacgtacgacaaaatattgaaaaacttatccagaaatagaagg
 C  D  A  A  E  T  T  Y  D  K  I  L  K  N  L  S  R  N  R  R
ctggtgagtgacaaagtagggcaggcatgttgcagacccatcgcctttgatgatgacctg
 L  V  S  D  K  V  G  Q  A  C  C  R  P  I  A  F  D  D  D  L
tcgtttttagatgataacctggtttaccatattctaagaaagcattccgctaaaaggtgt
 S  F  L  D  D  N  L  V  Y  H  I  L  R  K  H  S  A  K  R  C
ggatgtatctgatctaga
 G  C  I  -
```

Linker peptide is underlined.

Figure 6. Characterization of the RAP-GAA fusion.
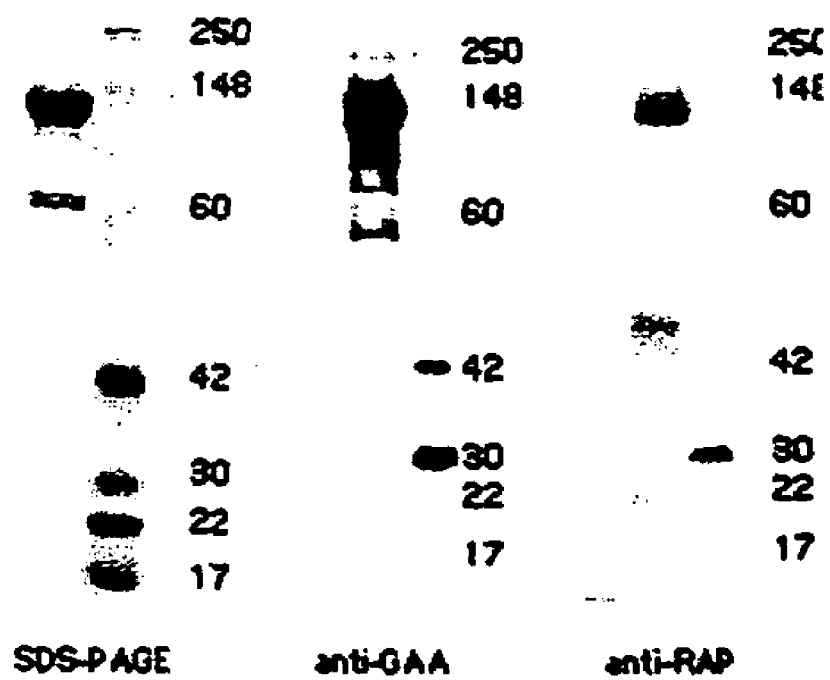

Figure 7. Assay for complex oligosaccharides on RAP-GAA
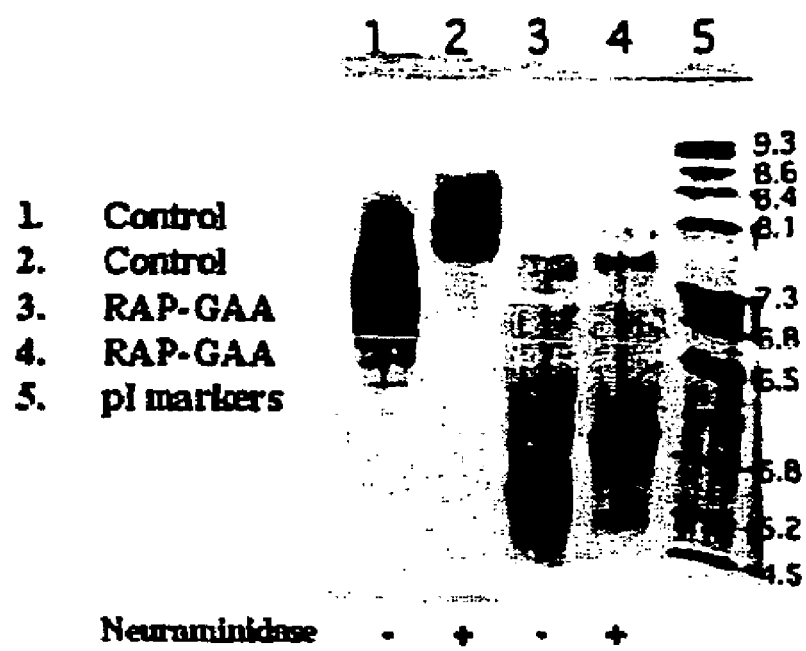
1. Control
2. Control
3. RAP-GAA
4. RAP-GAA
5. pI markers

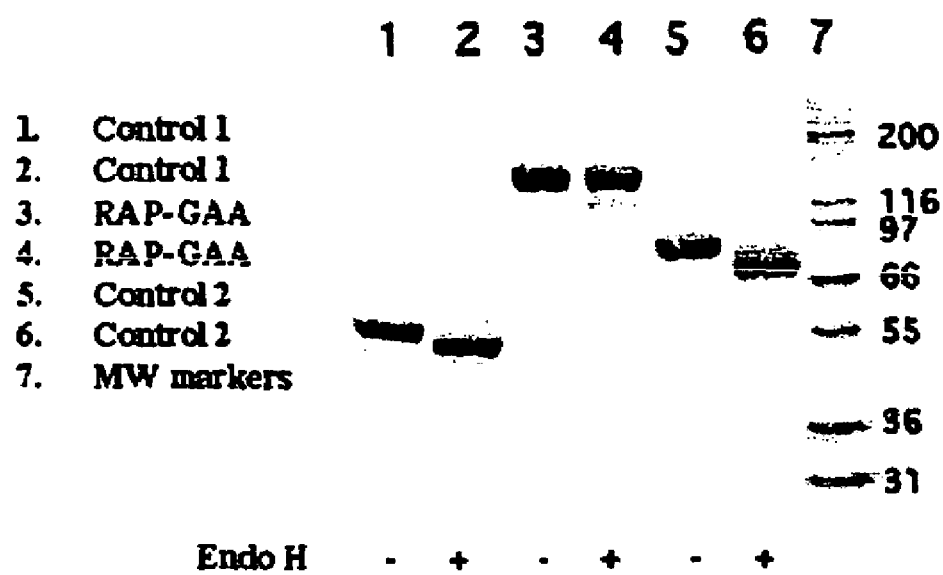
Figure 8. Assay for high-mannose oligosaccharides on RAP-GAA

Figure 9. Characterization of RAP-IDU fusion
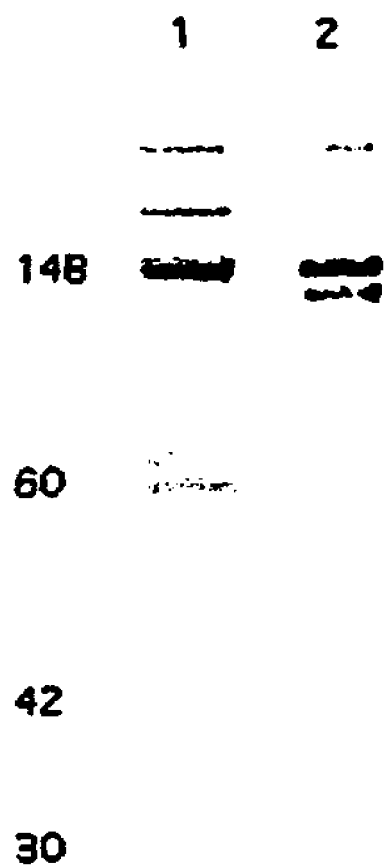
1. SDS-PAGE
2. Anti-Iduronidase Western Binding of RAP and RAP-lysosomal enzyme fusion to LRP.

| | None | RAP | RAP-Idu (Purified) | RAP-Idu (Medium) |
|---|---|---|---|---|
| Anti-RAP | | ● | ■ | ● |
| Anti-Idu | | | ● | ● |

FIGURE 10

Corrected $V_d$ vs. Perfusion time.

Distribution of RAP between brain capillary endothelium and brain parenchyma.

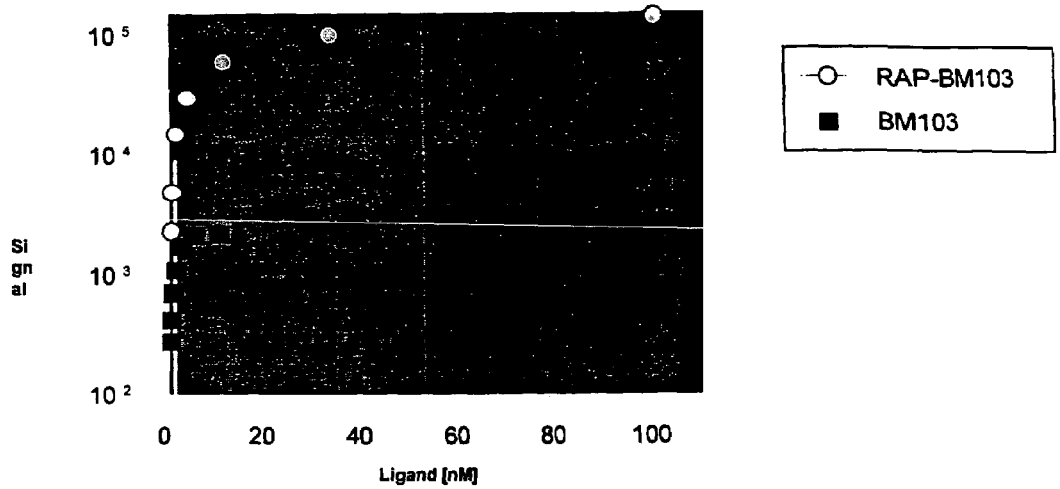
| RAP-BM103 | | | BM103 | | |
|---|---|---|---|---|---|
| Parameter | Value | Std. Error | Parameter | Value | Std. Error |
| Vmax | 160806 .4864 | 5540 .7619 | Vmax | 2691 .6376 | 112 .1342 |
| Km | 18 .6316 | 1 .8955 | Km | 1 .6615 | 0 .2002 |
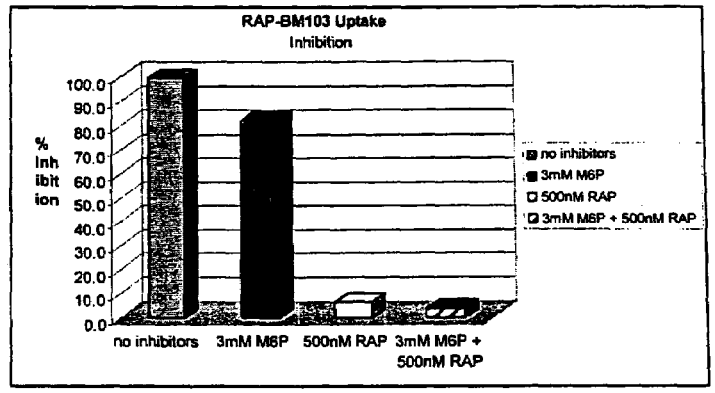
FIGURE 13

FIGURE 14. Multiple alignment of amino acid sequences of RAP from different species.

```
human       1  ---------------------MAPRRVRSFLRGLPA L ILLF GPWPAAS GGKYSR K
mouse       1  MGGPTRPSPVSLLALQRKMAPRRERVS LPRLQLLV LL P MI VPQPIAG GGKYSR K
rat         1  ---------------------LRDRVS LPRLQLLV LL P  I VPQPIAG GGKYSR K
chicken     1  ------------------------MGATRT  A V AAFLAVST A S   R A
zebrafish   1  -------------------------------------------------M GKYS  M
fruit fly   1  -----------------------MVR ALVVAAIA SV IA QGVDADKKQS  YS  A
mosquito    1  -------------ELCPIARRKGIKH LTMPLFTR C  VFT LVCNHVVQSE AHSKY
flatworm    1  -----------------------------------------------MRN    FLL
consensus   1                             t        l  ll lml        hggkysre human      40  ---------- PKPSP RES GE EFRMEKLNQ WEKAQRL H PPVRLAELH DLKIQE DE
mouse      61  ---------N PEMAA  ES GE EFRMEKLNQ WEKA RL HL PVRLAELHSDLKIQE DE
rat        40  ---------N PEMAA  ES GE EFRMEKLNQ WEKA RL HL PVRLAELHSDLKIQE DE
chicken    29  ---------N GLADA PR AG FR V LNQVWEKAQRL L A  LAELHSDLKIQEKDE
zebrafish  10  ---------N KNASD  SNNQV FR  A LNQVWEKAI    APVRL ELHSDLKIQEKDE
fruit fly  37  NDPHFQQVK    KYDPDF SIQRP FRMA KLN VW KAQNR L EP  KS YM LKIHD   
mosquito   48  SKHANALPDS  IYEPDF NIQRP FRMA KLN VW KAQ R L EP  KS Y  L  HD   
flatworm   10  ---------FLLVIGSA HNKKT Q   RI F  YEKA LQHVTDRQN  R  EK  SGY AIY
consensus  61             ne     kr   g efRmeklNqvweKAqrl lspvrLaeLhsdLkiqekde human      91  AWKKLK L GLD DGEKEA L IRNLNVILAKYGLDGK KDARQ  TSN-----S  SGTQ ---
mouse     112  LNWKKLK VEGLD KDGEKEAKLI HNLNVILA YGLDGRKDAQM  HSN-----A NEDT ---
rat        91  LNWKKLK VEGLD GDGEKEAKIV HNLNVILA YGLDGR KD TQT V HSN-----A NEDT ---
chicken    80  LS KKLKAEGL GEDGEKEAKLRRN NVI TKYG NGKK  SHLTD      ---- Y KRGT S-
zebrafish  61   Q KKLKAEGM EDGER EAKLRRNF   ILAKYGMDG KKL TRT DSNR---LKDH VKIG-
fruit fly  96  TA K  NS HK  KD L ADELRR  IG MSS D LEHF DTQDTEKLPYKKFH AE R-
mosquito  107   T  Q  N--EK KD L KEAE LFNK VS MST GI LEHF DTQDPEKYLAKSSDGAPKKD
flatworm   61  AS SN --QGTQGTKEID  DDK GK I EYGI EKAVLAFKEKYKHKNLFQQT DN P-
consensus 121  l wKklk egld dgekeaklrrnlnvIlakYgldgkkd    v sn     l e  e human     144  ----- GLD DPRLEKLW  KAKTSGKFS GEELDKLWREF LHHKEK  EYN LL TLS----
mouse     165  ----- ELG DPRLEKLW HKAKTSGKFS SEELDKLWREF LH YKEKI QEYN LI TLS----
rat       144  ----- ELG DPRLEKLW HKAKTSGKFS SEELDKLWREF LH YKEKI EYN LI TLS----
chicken   134  ----- TLD DPRLEKLW SKAKTSGKFS DEELDKLWRE  KHHKEKI EYN LL T  ----
zebrafish 117  ----- TFD    LDKLW NKA TSGKFS DEEL QT  HREF QHH  KI  EYN VM T  ----
fruit fly 155  -HRNKSLFK  K  LN LW EKA EI  G-   AEEL KS  KQ    DHH QD  VDV YSL  N G----
mosquito  165  TYKNKSLFK  K  LN KLW DKAE A  - K EELLA REE DH HQAK DV YSL  R  GDDDD
flatworm  118  --LPSGKFT  QN  KLW SQ  QNGK- Q  K  N  HG  LKEVE  MRV  EDQ  DFK----
consensus 181       d  DprLekLW kAktsgkFs eELdkLwrEf hhkeKiheYnvlletls human     195  ---------- TE  IHEN ISPSL S----------------D  KGSV HS  H ELKEKL
mouse     216  ---------- A  GYEN  SPSI MA---------------HI KSDT IS HSELKDR
rat       195  ---------- A  GYEN  SPSL T---------------HI KSDT ASK HSELKDR
chicken   185  ---------- TE I KK  INPSEEN--------------PV EEV HN HRELKEK
zebrafish 168  ---------- TE I K  VIS LEG---------------D  KENV HQK H D L QRM
fruit fly 209  --------TVDT  KHENA INTE  DTYNLISNDVNENDIKTHAQNVKSFENDLNT  GHH
mosquito  224  GGAAGQGSR DD ALL AVNDEE HDRYNEVDRAEETDRSQPGAN QHAYLH SN   R  H
flatworm  171  ---------    --VP HEN S  QHDIES----------------IG----D TKK  AAN
consensus 241              r ee henvispsdl               ik   l  khteLkekl
```

```
human      229 RSINQGLDRLRKVSHQGYSTEAEFEEPRVIDLWDLAQSA--LTKELERREELKHFEAK
mouse      250 RSINQGLDRLRKVSHQGYGTTEFEEPRVIDLWDLAQSA-NFTEKELESFREELKHFEAK
rat        229 RSINQGLDRLRKVSHQGYGPATEFEEPRVIDLWDLAQSA-NFTEKELESFREELKHFEAK
chicken    219 RSINQGFERLRKVSHQGYDATSEFEEPRVIDLWLMKSA-NFTEKELESFREELKHFEAK
zebrafish  201 SDLNQGFERLRKITHEGYTDDSEFRSPRVIELWEM-KRS-LSFDELDLKEELRHFFT
fruit fly  261 TGIKDHYDRLERIVSSPHIQ-DIEIKIQGLVRVACAS-NFTVKELESIKTELHHFESR
mosquito   284 EIRDNFDRIDRIASKIPKIQ-DFVEEKIQGLVRVLAS-DFSADEIASLKVEILEYESR
flatworm   197 EENDHLDEVHRKVTSEEFIP--FNEPRVKRLWKLAGENEKLIPHEISVLKDELSHFESQ
consensus  301 rsinqgldrlrrvshqgy s teFeEPrVidLWdlAqsa nftekELesfreELkHfEak human      288 IEKHNHYQKQLEISHEKLRHAES-----VGDGERVSRSREKHALLEGSTKELGYTVKKHL
mouse      309 IEKHNHYQKQLEISHQKLKHVES-----IGIPEHISRNKEKYVLLEEKTKELGYKVKKHL
rat        288 IEKHNHYQKQLEISHQKLKHVES-----IGIPEHISRNKEKYVLLEEKTKELGYKVKKHL
chicken    278 IEKHHHYQKQLEISHEKLKHIEG-----TGIKEHLNRKREKYAMLEEKTKELGYKVKKHL
zebrafish  260 VEKHEHYQEQLEISHQKLKHVEA-----IGLEDHIMRNKEKYNTLAEKAREMGYKMKKHI
fruit fly  319 ILKLRELHAEHALQKEKYKGEK------------VKDKSSREEMEQLAKQTRAVENLQ
mosquito   342 ILKLRHMHABHALSLEKHKHS--------------DAKAETHKIMEDNIAKQTRAVEMMQ
flatworm   255 IKKIEFHKVFFFVNSCPNRGKNEEVSRLQEDAEERGKDKSQVYENLELSIKHERINRKA
consensus  361 ieKhnhyqkqleisheklkhve        vgd ehv rnreky lleektkelgykvkkhl human      343 QDLSGRISR--ARHNEL
mouse      364 QDLSSRVSR--ARHNEL
rat        343 QDLSSRVSR--ARHNEL
chicken    333 QDLSSRISQG-LQHNEL
zebrafish  315 QDLINKISKNGLQHNEL
fruit fly  367 ENIEKTIFK----HTEL
mosquito   388 EEVERRIFK----HSEL
flatworm   315 RKLEKYIEEKIIIIREL
consensus  421 qdls risr     HnEL
```

FIGURE 14 (CONT)

Figure 15: Amino Acid Sequence Of Human RAP (SEQ ID NO:1)

TyrSerArgGluLysAsnGlnProLysProSerProLysArgGluSer
GlyGluGluPheArgMetGluLysLeuAsnGlnLeuTrpGluLysAla
GlnArgLeuHisLeuProProValArgLeuAlaGluLeuHisAlaAsp
LeuLysIleGlnGluArgAspGluLeuAlaTrpLysLysLeuLysLeu
AspGlyLeuAspGluAspGlyGluLysGluAlaArgLeuIleArgAsn
LeuAsnValIleLeuAlaLysTyrGlyLeuAspGlyLysLysAspAla
ArgGlnValThrSerAsnSerLeuSerGlyThrGlnGluAspGlyLeu
AspAspProArgLeuGluLysLeuTrpHisLysAlaLysThrSerGly
LysPheSerGlyGluGluLeuAspLysLeuTrpArgGluPheLeuHis
HisLysGluLysValHisGluTyrAsnValLeuLeuGluThrLeuSer
ArgThrGluGluIleHisGluAsnValIleSerProSerAspLeuSer
AspIleLysGlySerValLeuHisSerArgHisThrGluLeuLysGlu
LysLeuArgSerIleAsnGlnGlyLeuAspArgLeuArgArgValSer
HisGlnGlyTyrSerThrGluAlaGluPheGluGluProArgValIle
AspLeuTrpAspLeuAlaGlnSerAlaAsnLeuThrAspLysGluLeu
GluAlaPheArgGluGluLeuLysHisPheGluAlaLysIleGluLys
HisAsnHisTyrGlnLysGlnLeuGluIleAlaHisGluLysLeuArg
HisAlaGluSerValGlyAspGlyGluArgValSerArgSerArgGlu
LysHisAlaLeuLeuGluGlyArgThrLysGluLeuGlyTyrThrVal
LysLysHisLeuGlnAspLeuSerGlyArgIleSerArgAlaArgHis
AsnGluLeu

Figure 16: Amino Acid Sequence of the 28 kD RAP polypeptide (SEQ ID NO:2)

```
ProArgLeuGluLysLeuTrpHisLysAlaLysThrSerGlyLysPhe
SerGlyGluGluLeuAspLysLeuTrpArgGluPheLeuHisHisLys
GluLysValHisGluTyrAsnValLeuLeuGluThrLeuSerArgThr
GluGluIleHisGluAsnValIleSerProSerAspLeuSerAspIle
LysGlySerValLeuHisSerArgHisThrGluLeuLysGluLysLeu
ArgSerIleAsnGlnGlyLeuAspArgLeuArgArgValSerHisGln
GlyTyrSerThrGluAlaGluPheGluGluProArgValIleAspLeu
TrpAspLeuAlaGlnSerAlaAsnLeuThrAspLysGluLeuGluAla
PheArgGluGluLeuLysHisPheGluAlaLysIleGluLysHisAsn
HisTyrGlnLysGlnLeuGluIleAlaHisGluLysLeuArgHisAla
GluSerValGlyAspGlyGluArgValSerArgSerArgGluLysHis
AlaLeuLeuGluGlyArgThrLysGluLeuGlyTyrThrValLysLys
HisLeuGlnAspLeuSerGlyArgIleSerArgAlaArgHisAsnGlu
Leu
```

METHODS OF INCREASING DELIVERY OF ACTIVE AGENTS TO BRAIN COMPRISING ADMINISTERING RECEPTOR ASSOCIATED PROTEIN (RAP) FRAGMENTS CONJUGATED TO ACTIVE AGENTS

CROSS-REFERENCE TO RELATED APPLICATIONS

This application is a divisional of U.S. application Ser. No. 10/600,862. The contents of these and all other U.S. patents cited herein are each hereby incorporated by reference in their entirety.

FIELD OF THE INVENTION

The present invention is related to compositions comprising Receptor-Associated Protein (RAP) linked to a therapeutic and/or diagnostic/investigational agent, and methods of using such compounds.

BACKGROUND OF THE INVENTION

The brain is shielded against potentially harmful substances by the blood-brain barrier (BBB). The microvascular barrier between blood and brain is made up of a capillary endothelial layer surrounded by a basement membrane and tightly associated accessory cells (pericytes, astrocytes). The brain capillary endothelium is much less permeable to low-molecular weight solutes than other capillary endothelia due to an apical band of tight association between the membranes of adjoining cells, referred to as tight junctions. In addition to diminished passive diffusion, brain capillary endothelia also exhibit less fluid-phase pinocytosis than other endothelial cells. Brain capillaries possess few fenestrae and few endocytic vesicles, compared to the capillaries of other organs (see Pardridge, *J. Neurovirol.* 5: 556-569 (1999)). There is little transit across the BBB of large, hydrophilic molecules aside from some specific proteins such as transferrin, lactoferrin and low-density lipoproteins, which are taken up by receptor-mediated endocytosis (see Pardridge, 1999); Tsuji and Tamai, *Adv. Drug Deliv. Rev.* 36: 277-290 (1999); Kusuhara and Sugiyama, *Drug Discov. Today* 6:150-156 (2001); Dehouck, et al. *J. Cell. Biol.* 138: 877-889(1997); Fillebeen, et al. *J. Biol. Chem.* 274: 7011-7017 (1999)).

The blood-brain barrier (BBB) also impedes access of beneficial active agents (e.g., therapeutic drugs and diagnostic agents) to central nervous system (CNS) tissues, necessitating the use of carriers for their transit. Blood-brain barrier permeability is frequently a rate-limiting factor for the penetration of drugs or peptides into the CNS (see Pardridge, 1999); Bickel, et al., *Adv. Drug Deliv. Rev.* 46: 247-279 (2001)). For example, management of the neurological manifestations of lysosomal storage diseases (LSDs) is significantly impeded by the inability of therapeutic enzymes to gain access to brain cell lysosomes. LSDs are characterized by the absence or reduced activity of specific enzymes within cellular lysosomes, resulting in the accumulation of undegraded "storage material" within the intracellular lysosome, swelling and malfunction of the lysosomes, and ultimately cellular and tissue damage. Intravenous enzyme replacement therapy (ERT) is beneficial for LSDs (e.g. MPS I, MPS II). However, the BBB blocks the free transfer of many agents from blood to brain, and LSDs that present with significant neurological sequelae (e.g. MPS III, MLD, GM1) are not expected to be as responsive to intravenous ERT. For such diseases, a method of delivering the replacement enzyme across the BBB and into the lysosomes of the affected cells would be highly desirable.

Three ways of circumventing the BBB to enhance brain delivery of an administered active agent include direct intracranial injection, transient permeabilization of the BBB, and modification of the active agent to alter tissue distribution. Direct injection of an active agent into brain tissue bypasses the vasculature completely, but suffers primarily from the risk of complications (infection, tissue damage) incurred by intracranial injections and poor diffusion of the active agent from the site of administration. Permeabilization of the BBB entails non-specifically compromising the BBB concomitant with injection of intravenous active agent and is accomplished through loosening tight junctions by hyperosmotic shock (e.g. intravenous mannitol). High plasma osmolarity leads to dehydration of the capillary endothelium with partial collapse of tight junctions, little selectivity in the types of blood-borne substances that gain access to the brain under these conditions, and damage over the course of a life-long regimen of treatment.

The distribution of an active agent into the brain may also be increased by transcytosis, the active transport of certain proteins from the luminal space (blood-side) to the abluminal space (brain-side) of the BBB. Transcytosis pathways are distinct from other vesicular traffic within the capillary endothelial cell and transit can occur without alteration of the transported materials. Transcytosis is a cell-type specific process mediated by receptors on the BBB endothelial surface. Attachment of an active agent to a transcytosed protein (vector or carrier) is expected to increase distribution of the active substance to the brain. In transcytosis, the vector is presumed to have a dominant effect on the distribution of the joined pair. Vector proteins include antibodies directed at receptors on the brain capillary endothelium (Pardridge, 1999) and ligands to such receptors (Fukuta, et al, 1994; Broadwell, et al., 1996),). Antibody vectors are transported through the capillary endothelium by a process of adsorptive endocytosis (non-specific, membrane-phase endocytosis) and are far less efficiently transported than actual receptor ligands, which cross the BBB by a saturable, energy-dependent mechanism (Broadwell, et al. 1996).

The lipoprotein receptor-related protein (LRP) receptor family comprises a group of membrane-spanning, endocytic proteins with homology to the LDL receptor. Characterized as playing a key role in lipoprotein metabolism, LRP have subsequently been shown to bind a variety of ligands present in the blood. (Herz and Strickland, 2001). LRP ligandsinclude the lipoprotein-associated proteins ApoE, ApoJ and lipoprotein lipase; proteinases tPA, uPA, Factor IX and MMP-9; proteinase inhibitors PAI-1, antithrombin III, alpha-2-macroglobulin and alpha-antitrypsin; the antibacterial protein lactoferrin; the chaperone receptor-associated protein (RAP), the hormone thyrotropin, the cofactor cobalamin and the lysosomal proteins saposin and sphingolipid activator protein. Four of these ligands, ApoJ (Zlokovic, et al., 1996), thyrotropin (Marino, et al., 2000), lipoprotein lipase (Obunike, et al. 2001) and cobalamin (Ramanujam, et al., 1994) have been shown to be transcytosed across capillary endothelial cells in vitro and in vivo by LRP family members.

Taken together, the LRP receptor family comprises a pool of compositionally and functionally related receptors expressed at different levels in different tissues, including capillary endothelium, neurons and astrocytes. LRP family members are professional endocytic receptors that have also been shown to transcytose ligands across polarized epithelia.

A unique LRP ligand is the receptor-associated protein, RAP, a 39 kD chaperone localized to the endoplasmic reticulum and Golgi (Bu and Schwartz, *Trends Cell. Biol.* 8(7): 272-6 (1998)). RAP binds tightly to LRP in these compartments preventing premature association of the receptor with co-expressed ligands (Herz and Wilinow, *Atherosclerosis* 118 Suppl:S37-41 (1995)). RAP serves as an attractive targeting sequence for LRP due to its high affinity for all members of the LRP receptor family (~2 nM) and ability to out-compete all known LRP ligands. Since RAP is not secreted, endogenous levels in the blood are low. Endocytosis of RAP by LRP results in localization to the lysosome and complete degradation of the protein. Structure-function studies have been performed on RAP, providing some guidance on minimization of the sequence required to fulfill the targeting function (Melman, et al., *J. Biol. Chem.* 276(31): 29338-46 (2001)). It is not known whether RAP is transcytosed, but Megalin-RAP complexes have been shown to remain intact as far as the late endosome (Czekay, et al., *Mol. Biol. Cell.* 8(3):517-32 (1997)). The integrity of the Megalin-RAP complex through the Compartment of Uncoupling Ligand from Receptor (CURL) and into this late endosomal compartment is in contrast to the observed instability of other LRP-ligand complexes in the early endosome. The LRP-RAP complex thus appears to have enhanced resistance to acid-dependent dissociation, a potential indicator of transcytotic competence. RAP could be engineered to be more specific for particular members of the LRP family. Such modifications would allow more selective targeting of RAP fusions to particular tissues, as dictated by the expression of different LRP family members on those tissues.

Futhermore, RAP may be a suitable substitute for the mannose 6-phosphate targeting signal on lysosomal enzymes. The LRP-RAP system shares many features with the mannose-6-phosphate receptor (MPR)-mannose 6-phosphate (M6P) system: Both receptor-ligand complexes, LRP-RAP and MPR-M6P, exhibit dissociation constants in the 1-2 nM range and are stable in the CURL. Both LRP and MPR are widely expressed on a variety of tissues and efficiently transport bound ligand to the lysosome. Both types of ligands are degraded upon reaching the lysosome. The advantage of RAP targeting over M6P targeting is that it depends on a protein sequence rather than a modified carbohydrate. Biosynthetic throughput and quality control are much higher for an amino acid sequence than for a modified oligosaccharide, allowing for better drug yield, potency and safety. The LRP-RAP system may also provide a method of efficiently targeting other tissues. For example, the high density of the Very Low Density Lipoprotein Receptor (VLDLR), a member of the LRP family), as well as LRP1 on muscle cells implies that RAP fusions could be taken up to a significant extent by muscle through LRP receptor-dependent endocytosis (Takahashi, et al., *Proc. Natl. Acad. Sci. U.S.A.* 89(19):9252-6 (1992)).

There is a need for novel compounds, pharmaceutical compositions, and methods of administration of such compounds and compositions that can more effectively deliver active agents to the brain and other biological compartments. In particular, there is a need for such novel compounds, pharmaceutical compositions, and methods of administration which deliver active agents to the brain and tissues or organs that are set off from the blood compartment by capillary endothelial cells that are closely sealed by tight junctions. In particular, there is a need for such novel compounds, pharmaceutical compositions, and methods of administration, which efficiently target the delivery of an active agent to a wide variety of tissues. In particular, there is a need for such novel compounds, pharmaceutical compositions, and methods of administration, which target the delivery of an active agent to the lysosomal compartment of a cell within those tissues. This invention provides such compounds, pharmaceutical compositions and methods for their use.

BRIEF SUMMARY OF THE INVENTION

The present invention relates to the discovery that RAP and RAP polypeptides selectively bind to LRP receptors and, as carriers or vectors, RAP serves to increase the transport of therapeutic and/or diagnostic/investigational agents across the blood brain barrier and/or deliver agents to lysosomes of cells within and without the CNS.

In one aspect, the invention provides compounds comprising RAP or a RAP polypeptide conjugated to a therapeutic and/or diagnostic/investigational agent and pharmaceutical compositions of such compounds. In some embodiments, the RAP or RAP polypeptide conjugate according to the invention may be modified as desired to enhance its stability or pharmacokinetic properties (e.g., PEGylation of the RAP moiety of the conjugate, mutagenesis of the RAP moiety of the conjugate). In some preferred embodiments, the agent is a bioactive protein or peptide covalently linked to the RAP or RAP polypeptide moiety of the compound. Such conjugates may be formed by synthetic chemical reactions or joined by linker groups. In preferred embodiments, when the active agent is a protein or enzyme, the protein or enzyme is the human enzyme, a fragment of the human protein or enzyme having a biological activity of a native protein or enzyme, or a polypeptide that has substantial amino acid sequence homology with the human protein or enzyme. In some embodiments, the agent is a protein of human or mammalian sequence, origin or derivation. In some embodiments, the compound is a fusion protein of RAP or a RAP polypeptide portion and an active agent protein or polypeptide portion. The agent polypeptide portion of the fusion protein may be a substance having therapeutic activity such as a growth factor, lymphokine or peptide drug. The agent may be an enzyme or other bioactive protein or polypeptide. In other embodiments, the agent is an enzyme or protein whose deficiency causes a human disease such as Pompe's disease (e.g. alpha-glucosidase). In other embodiments, the enzyme is selected for its beneficial effect. In other embodiments, the conjugate is formed by non-covalent bonds between the carrier and an antibody to which the active agent is attached.

The RAP or RAP polypeptide can also be of human or mammalian sequenceorigin or derivation. In yet other embodiments of the invention, in each of its aspects, the RAP or RAP polypeptide is identical in amino acid sequence to the corresponding portion of a human or mammalian RAP polypeptide amino acid sequence. In other embodiments, the RAP or RAP polypeptide moiety is the native protein from the human or mammal. In other embodiments, the RAP or RAP polypeptide is substantially homologous (i.e., at least 80%, 85%, 90%, 95%, 98%, or 99% identical in amino acid sequence) over a length of at least 25, 50, 100, 150, or 200 amino acids, or the entire length of the RAP polypeptide, to the native RAP sequence of human or mammalian RAP. In other embodiments, the subject to which the conjugate is to be administered is human.

In preferred embodiments of the invention, when the active agent conjugated to RAP or RAP polypeptide is a protein or enzyme, or fragment thereof possessing a biological activity of the protein or enzyme, the active agent has an amino acid sequence identical to the amino acid sequence to the corresponding portion of the human or mammalian protein or enzyme. In other embodiments, the active agent moiety of the conjugate is a protein or enzyme native to the species of the human or mammal. In other embodiments, the protein or enzyme, or fragment thereof, is substantially homologous (i.e., at least 80%, 85%, 90%, 95%, more preferably 98%, or most preferably 99% identical in amino acid sequence over a length of at least 10, 25, 50, 100, 150, or 200 amino acids, or the entire length of the active agent) to a native sequence of the corresponding human or mammal protein or enzyme. In other embodiments, the subject to which the conjugate is to be administered is human.

In a second aspect, the invention provides a method for delivering therapeutic and/or diagnostic/investigational agents to the central nervous system using the RAP/LRP carrier system to transport such agents across the BBB formed by the capillary endothelial cells which are closely sealed by tight junctions. The invention thereby provides a novel route of administering agents with a site of action within the central nervous system. In a further embodiment, a modulator of LRP is co-administered to modulate the therapeutic or adverse effects of such a conjugate.

In some embodiments, the RAP or RAP polypeptide conjugates with an active agent comprise more than one therapeutic active agent useful in treating the same condition or disorder linked to a single RAP polypeptide. In some embodiments, from about 1 to about 5 or from 2 to 10 molecules of the active agent is attached to one RAP or RAP polypeptide molecule to be administered to a patient having the disease, condition or disorder.

In a third aspect, the invention provides methods for using the RAP carrier system in the treatment of diseases, disorders, or conditions. In one group of embodiments, the RAP conjugates may be used to treat a CNS condition or disorder. In one group of particularly preferred embodiments to be treated, the CNS condition or disorder to be treated is a brain tumor or other neoplasia (e.g., a CNS tumor such as a glioblastoma). Such tumors or neoplasia may be primary tumors or may be metastases. In these embodiments, the compounds according to the invention may comprise RAP or a RAP polypeptide conjugated to a cancer chemotherapeutic agent. Preferred compounds have from about 1 to about 20 molecules of the chemotherapeutic agent covalently linked to each RAP or RAP polypeptide moiety. Such compounds are excellent vehicles for enhanced delivery of chemotherapeutic agents to brain tumors and other neoplasia localized in or around the brain, and for improved treatment of such tumors and neoplasia. In some embodiments, the cancer chemotherapeutic agents conjugated to a RAP polypeptide may be the same or different. For instance, from 1 to 3 different chemotherapeutic agents may be attached in the same or a different mole RAP polypeptide per mole active agent ratio (e.g., 1:1; 1:2; 1:3; 1:4; and 1:5 to 1:10) with respect to the RAP or RAP polypeptide moiety of the compound. Preferred chemotherapeutic agents for such conjugates include, but are not limited to adriamycin, cisplatin, 5-fluorouracil, camptothecin, and paclitaxel. In another embodiment, the present invention provides a method of treating a patient with a brain or CNS tumor or glioblastoma by administering to the patient a therapeutically effective amount of RAP or a RAP polypeptide conjugated to the chemotherapeutic agent. In another embodiment, the present invention provides for a method for delivering a compound of interest through the blood-brain barrier of a subject into the brain parenchyma where the compound is a chemotherapeutic able to interfere with the division of the tumor cells and are toxic for dividing cells. These compounds are liberated in the lysosomes following degradation of the vector and can diffuse thru the lysosomal membrane and enter the nucleus.

In another group of embodiments, the present invention provides compounds, pharmaceutical compositions, and methods for treating neurologic and psychiatric diseases and CNS diseases, disorders and conditions, including, but not limited to, Alzheimere's Disease, Parkinson's Disease, Multiple Sclerosis, and Amylotrophic Lateral Sclerosis. In some embodiments, the compounds of the invention comprise RAP or a RAP polypeptide conjugated to a therapeutic agent for treating such diseases, disorders and conditions. In a preferred group of embodiments, the therapeutic agent is a peptide including, but not limited to, Nerve Growth Factor, other peptide hormones or growth factors, and peptide neurotransmitters. In another embodiment, the present invention provides for a method for delivering an active agent through the blood-brain barrier of a subject into the brain parenchyma where the active agent is a neurotrophic factors including, but not limited to, Nerve Growth Factor, Brain-Derived Neurotrophic Factor, Neurotrophin-3, Neurotrophin-4/5, aFGF, bFGF, CNTF, Leukaemia Inhibitory Factor, Cardiotrophin-1, TGFb, BMPs, GDFs, Neurturin, Artemin, Persephin, EGF, TGFa, Neuregulins, IGF-1, IGF-2, ADNF and PDGFs. Other factors such as caspase inhibitors can also be conjugated as the active agent member of the compound. In other embodiments, the active agent is a therapeutic antibody directed toward a constituent of the CNS. In other embodiments, the active agent is an antimicrobial agent for treating or preventing a CNS infection or an immunomodulator such as lymphokine.

In some embodiments, the RAP polypeptide active agent conjugate is administered to treat a disease or condition selected from the group consisting of neurological diseases including, but not limited to, conditions such as Alzheimer's Disease, Parkinson's Disease, schizophrenia, and epilepsy; neurological cancers, such as primary brain tumors including glioma, meningioma, neurinoma, pituitary adenoma, medulloblastoma, craniopharyngioma, hemangioma, epidermoid, sarcoma and intracranial metastasis from other tumor sources, and neurological infections or neurological inflammatory conditions.

In still other aspects, the RAP conjugates of the invention can be used to treat non-CNS (i.e., non-BBB delimited diseases, such as cancers, diseases and conditions of non-CNS organs). For example, conjugated agents can be used to treat conditions affecting a patient's muscles.

In other aspects, the invention provides methods of treating tissues or organs having proportionately greater, preferably more than two-fold, amounts of LRP receptors on their cells than other tissues or organs. The selective biodistribution of RAP or RAP-polypeptide conjugated active agents can enhance the selective targeting of such conjugated agents to specific organs.

In a fourth aspect, the invention provides a method for using the RAP/LRP carrier system in the diagnosis of diseases, disorders, or conditions. The present invention provides screening assays for identifying RAP or RAP polypeptide active agent conjugates that can prevent, amelioriate, or treat a CNS disease or disorder by measuring the transcytosis of such agents in in vitro models or by measuring the ability of such conjugates to reach or bind to the brain parenchyma in vivo. Transcytosis or delivery can be assessed by labeling the conjugate and then monitoring or detecting the location or transport of the label in the test chamber for an in vitro method or in a tissue compartment(s) in an in vivo method. In addition, a therapeutic effect or other biological effect of the conjugate can be used to monitor for passage of the RAP active agent conjugate into the parenchyma of the central nervous system. In preferred embodiments, the CNS condition is a brain tumor.

In a fifth aspect, the invention provides a method of delivering a therapeutic enzyme to a lysosome in a brain cell of a subject, comprising: (i) administering a compound comprising RAP conjugated to the therapeutic enzyme, (ii) transporting such compound across the capillary endothelium; (iii) contact of such compound with an LRP receptor on the cell, thereby facilitating entry of such compound into such cell by endocytosis; and (iv) delivery to lysosomes within the cell. In certain other aspects, the invention provides compounds, compositions, and methods for delivering a therapeutic agent or diagnostic agent to the lysosome of a cell.

In a sixth aspect, the invention provides a method of treating lysosomal storage diseases by administering RAP fused with a therapeutic enzyme, wherein the RAP-enzyme complex binds to an LRP receptor and is transported across the cell membrane, enters the cell and is delivered to the lysosomes within the cell. In some embodiments, the invention also provides a method of treating a lysosomal storage disease in a patient by administering RAP or a RAP polypeptide conjugated to a therapeutic agent which is a protein or enzyme deficient in the lysosomes of a subject having such a disease (e.g., enzyme replacement therapy). Such RAP or RAP polypeptide active agent conjugates are particularly useful, for example, in the treatment of lysosomal storage diseases such as MPS I, MPS II, MPS III A, MPS III B, Metachromatic Leukodystrophy, Gaucher, Krabbe, Pompe, CLN2, Niemann-Pick and Tay-Sachs disease wherein a lysosomal protein deficiency contributes to the disease state. In yet other embodiments, the invention also provides a pharmaceutical composition comprising RAP or RAP polypeptide covalently linked to a protein or enzyme deficient in a lysosomal storage disease.

In some embodiments, the compounds, compositions, and methods of the invention can be used to treat such lysosomal storage diseases as Aspartylglucosaminuria, Cholesterol ester storage disease/Wolmanr disease, Cystinosis, Danon disease, Fabry disease, Farber Lipogranulomatosis/Farber disease, Fucosidosis, Galactosialidosis types I/II, Gaucher disease types I/IIIII Gaucher disease, Globoid cell leukodystrophy/Krabbe disease, Glycogen storage disease II/Pompe disease, GM1-Gangliosidosis types I/II/III, GM2-Gangliosidosis type I/Tay-Sachs disease, GM2-Gangliosidosis type II Sandhoff disease, GM2-Gangliosidosis, alpha-Mannosidosis types I/II, alpha-Mannosidosis, Metachromatic leukodystrophy, Mucolipidosis type I/Sialidosis types I/II Mucolipidosis types II/III I-cell disease, Mucolipidosis type IIIC pseudo-Hurler polydystrophy, Mucopolysaccharidosis type I, Mucopolysaccharidosis type II Hunter syndrome, Mucopolysaccharidosis type IIIA Sanfilippo syndrome, Mucopolysaccharidosis type IIIB Sanfilippo syndrome, Mucopolysaccharidosis type IIIC Sanfilippo syndrome, Mucopolysaccharidosis type IIID Sanfilippo syndrome, Mucopolysaccharidosis type IV A Morquio syndrome, Mucopolysaccharidosis type IVB Morquio syndrome, Mucopolysaccharidosis type VI, Mucopolysaccharidosis type VII Sly syndrome, Mucopolysaccharidosis type IX, Multiple sulfatase deficiency, Pompe, Neuronal Ceroid Lipofuscinosis, CLN1 Batten disease, Neuronal Ceroid Lipofuscinosis, CLN2 Batten disease, Niemann-Pick disease types A/B Niemann-Pick disease, Niemann-Pick disease type C1 Niemann-Pick disease, Niemann-Pick disease type C2 Niemann-Pick disease, Pycnodysostosis, Schindler disease types I/II Schindler disease, and Sialic acid storage disease. In particularly preferred embodiments, the lysosomal storage disease is MPS III, MLD, or GM1.

In still another embodiment, the present invention provides for a method of enzyme replacement therapy by administering a therapeutically effective amount of a conjugate to a subject in need of the enzyme replacement therapy, wherein the conjugate comprises RAP or a RAP polypeptide linked to an enzyme via a linker, wherein the cells of the patient have lysosomes which contain insufficient amounts of the enzyme to prevent or reduce damage to the cells, whereby sufficient amounts of the enzyme enter the lysosomes to prevent or reduce damage to the cells. The cells may be within or without the CNS or need not be set off from the blood by capillary walls whose endothelial cells are closely sealed to diffusion of an active agent by tight junctions.

In some embodiments, the RAP or RAP polypeptide conjugates with an active agent comprising more than one active agent for treating a lysosomal storage disease linked to a single RAP polypeptide. In some embodiments, from about 1 to about 5 or from 2 to 10 molecules of the active agent of interest bound to a single RAP or RAP polypeptide molecule.

In a particular embodiment, the invention provides compounds comprising RAP or a RAP polypeptide bound to an active agent having a biological activity which is reduced, deficient, or absent in the target lysosome of the subject to which the compound is administered. In preferred embodiments, the RAP or a RAP polypeptide is covalently bound to the active agent. Preferred active agents include, but are not limited to aspartylglucosaminidase, acid lipase, cysteine transporter, Lamp-2, alpha-galactosidase A, acid ceramidase, alpha-L-fucosidase, beta-hexosaminidase A, GM2-activator deficiency, alpha-D-mannosidase, beta-D-mannosidase, arylsulfatase A, saposin B, neuraminidase, alpha-N-acetyl-glucosaminidase phosphotransferase, phosphotransferase γ-subunit, alpha-L-iduronidase, iduronate-2-sulfatase, heparan-N-sulfatase, alpha-N-aceiylglucosaminidase, acetyl-CoA:N-acetyltransferase, N-acetylglucosamine 6-sulfatase, galactose 6-sulfatase, alpha-galactosidase , N-acetylgalactosamine 4-sulfatase, hyaluronoglucosam inidase, palmitoyl protein thioesterase, tripeptidyl peptidase I, acid sphingomyelinase, cholesterol trafficking, cathepsin K, beta-galactosidase B, α-glucosidase, and sialic acid transporter. In a preferred embodiment, alpha-L-iduronidase, α-glucosidase or N-acetylgalactosamine 4-sulfatase is the enzyme.

In a seventh aspect, the invention provides screening assays for identifying RAP or RAP polypeptide active agent conjugates that can prevent, amelioriate, or treat a lysosomal storage disease by contacting a cell containing a lysosome with the conjugate and determining whether the conjugate delivers the agent to the lysosome. The delivery can be assessed by labeling the conjugate and then monitoring or detecting the location of the label in the cell or by determining the effect of the conjugate on the amount of the storage material found in the lysosome. In a preferred embodiment, the agent is a protein or enzyme deficient in the lysosomal storage disease. In another embodiment, the cell is deficient in the agent conjugated to the RAP or RAP polypeptide.

In another embodiment, the present invention provides for a method for identifying an agent that can prevent, ameliorate or treat a lysosomal storage disease, by administering RAP or a RAP polypeptide conjugated enzyme to a cell, wherein absence of the enzyme causes the lysosomal storage disease; and determining whether the agent reduces damage to the cell compared to damage to the cell if the conjugated agent was not administered to the cell. In certain embodiments, the method is a high throughput assay.

BRIEF DESCRIPTION OF THE DRAWINGS

FIG. 2. Preparation of expression constructs endcoding fusions between human RAP and human glucosidase (GAA), alpha-L-iduronidase (IDU) and glial-derived neurotrophic factor (GDNF).

FIG. 3. Nucleotide and protein sequences of the RAP-GAA fusion.

FIG. 4. Nucleotide and protein sequence of RAP-IDU fusion

FIG. 5. Nucleotide and protein sequence of RAP-GDNF fusion.

FIG. 6. Characterization of the RAP-GAA fusion.

FIG. 7. Assay for complex oligosaccharides on RAP-GAA.

FIG. 8. Assay for high-mannose oligosaccharides on RAP-GAA.

FIG. 9. Characterization of RAP-IDU fusion.

FIG. 10. Binding of RAP and RAP-lysosomal enzyme fusion to LRP.

FIG. 13. RAP-alpha-glucosidase uptake by human Pompe fibroblasts.

FIG. 14. Multiple alignment of amino acid sequences of RAP from different species.

FIG. 15. SEQ ID NO:1, amino acid sequence of human RAP.

FIG. 16. SEQ ID NO:2, amino acid sequence of the 28 kD RAP polypeptide.

DETAILED DESCRIPTION OF THE INVENTION

Figure 1:
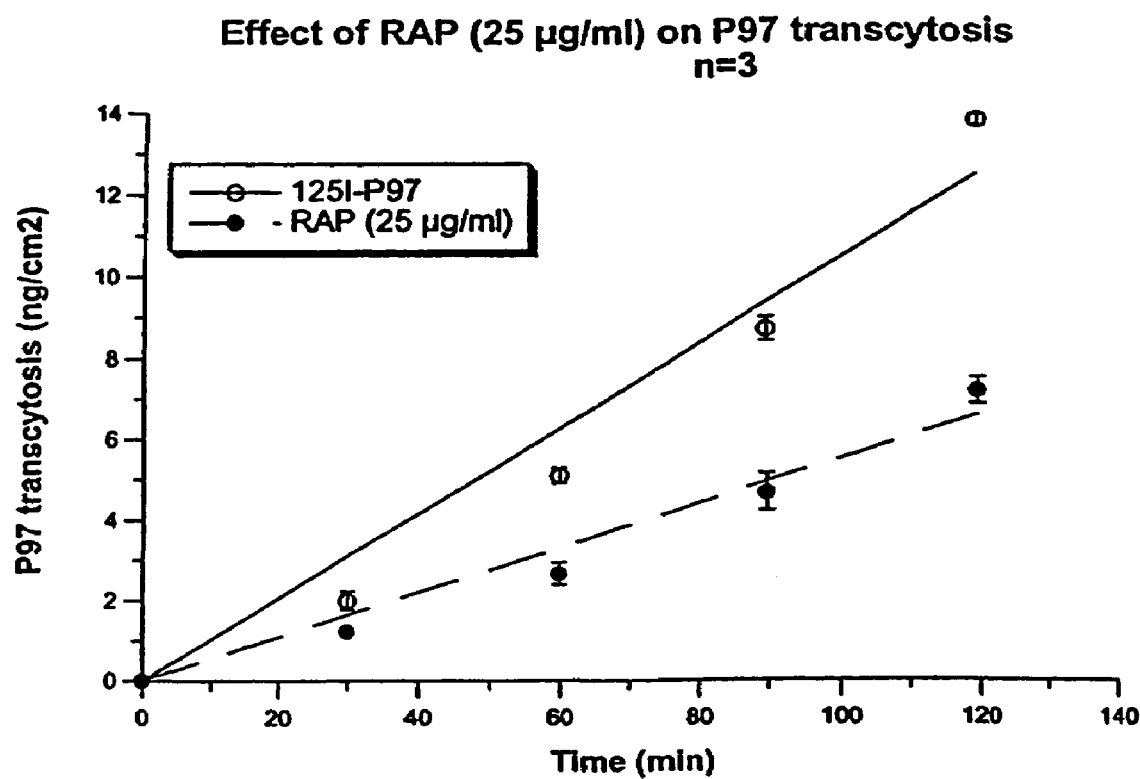
FIG. 1. Effect of RAP on [$^{125}$I]-p97 transcytosis across BBCEC monolayers.

The present invention relates to the discovery that RAP and RAP polypeptides selectively bind to LRP receptors. RAP is a particularly effective carrier for delivering active agents conjugated to it across the blood brain barrier, to the lysosomes within a cell, and to the intracellular compartment of cells bearing LRP receptors. Compounds comprising RAP polypeptide conjugated to an active agent are useful in the diagnosis and treatment of a variety of CNS and non-CNS diseases, conditions, and disorders, including but not limited to, in particular, cancer and lysosomal storage diseases.

I. Definitions

Unless otherwise defined, all technical and scientific terms used herein have the same meaning as commonly understood by one of ordinary skill in the art to which this invention belongs. The following references provide one of skill with a general definition of many of the terms used in this invention. Singleton, et al., DICTIONARY OF MICROBIOLOGY AND MOLECULAR BIOLOGY (2d ed. 1994); THE CAMBRIDGE DICTIONARY OF SCIENCE AND TECHNOLOGY (Walker ed., 1988); THE GLOSSARY OF GENETICS, 5TH ED., R. Rieger, et al. (eds.), Springer Verlag (1991); and Hale & Marham, THE HARPER COLLINS DICTIONARY OF BIOLOGY (1991).

Each publication, patent application, patent, and other reference cited herein is incorporated by reference in its entirety to the extent that it is not inconsistent with the present disclosure.

It is noted here that as used in this specification and the appended claims, the singular forms "a," "an," and "the" include plural reference unless the context clearly dictates otherwise.

As used herein, the following terms have the meanings ascribed to them unless specified otherwise.

"Brain tumors and other neoplasia in or around the brain" as used herein includes both primary tumors and/or metastases that develop in or around the brain. It may also mean metastases of brain tumors that migrate elsewhere in the body, but remain responsive to RAP or RAP polypeptide conjugates with chemotherapeutic agents. Many types of such tumors and neoplasia are known. Primary brain tumors include glioma, meningioma, neurinoma, pituitary adenoma, medulloblastoma, craniopharyngioma, hemangioma, epidermoid, sarcoma and others. Fifty percent of all intracranial tumors are intracranial metastasis. As used herein, tumors and neoplasia may be associated with the brain and neural tissue, or they may be associated with the meninges, skull, vasculature or any other tissue of the head or neck. Such tumors are generally solid tumors, or they are diffuse tumors with accumulations localized to the head. Tumors or neoplasia for treatment according to the invention may be malignant or benign, and may have been treated previously with chemotherapy, radiation and/or other treatments.

The term "effective amount" means a dosage sufficient to produce a desired result on a health condition, pathology, and disease of a subject or for a diagnostic purpose. The desired result may comprise a subjective or objective improvement in the recipient of the dosage. "Therapeutically effective amount" refers to that amount of an agent effective to produce the intended beneficial effect on health.

"Small organic molecule" refers to organic molecules of a size comparable to those organic molecules generally used in pharmaceuticals. The term excludes organic biopolymers (e.g., proteins, nucleic acids, etc.). Preferred small organic molecules range in size up to about 5000 Da, up to about 2000 Da, or up to about 1000 Da.

A "subject" of diagnosis or treatment is a human or non-human animal, including a mammal or a primate.

"Treatment" refers to prophylactic treatment or therapeutic treatment or diagnostic treatment.

A "prophylactic" treatment is a treatment administered to a subject who does not exhibit signs of a disease or exhibits only early signs for the purpose of decreasing the risk of developing pathology. The conjugate compounds of the invention may be given as a prophylactic treatment to reduce the likelihood of developing a pathology or to minimize the severity of the pathology, if developed.

A "therapeutic" treatment is a treatment administered to a subject who exhibits signs or symptoms of pathology for the purpose of diminishing or eliminating those signs or symptoms. The signs or symptoms may be biochemical, cellular, histological, functional, subjective or objective. The conjugate compounds of the invention may be given as a therapeutic treatment or for diagnosis.

"Diagnostic" means identifying the presence or nature of a pathologic condition. Diagnostic methods differ in their specificity and selectivity. While a particular diagnostic method may not provide a definitive diagnosis of a condition, it suffices if the method provides a positive indication that aids in diagnosis.

"Pharmaceutical composition" refers to a composition suitable for pharmaceutical use in subject animal, including humans and mammals. A pharmaceutical composition comprises a pharmacologically effective amount of a RAP polypeptide conjugated to an active agent and also comprises a pharmaceutically acceptable carrier. A pharmaceutical composition encompasses a composition comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a conjugate compound of the present invention and a pharmaceutically acceptable carrier.

"Pharmaceutically acceptable carrier" refers to any of the standard pharmaceutical carriers, buffers, and excipients, such as a phosphate buffered saline solution, 5% aqueous solution of dextrose, and emulsions, such as an oil/water or water/oil emulsion, and various types of wetting agents and/or adjuvants. Suitable pharmaceutical carriers and formulations are described in Remington's Pharmaceutical Sciences, 19th Ed. (Mack Publishing Co., Easton, 1995). Preferred pharmaceutical carriers depend upon the intended mode of administration of the active agent. Typical modes of administration include enteral (e.g., oral) or parenteral (e.g., subcutaneous, intramuscular, intravenous or intraperitoneal injection; or topical, transdermal, or transmucosal administration). A "pharmaceutically acceptable salt" is a salt that can be formulated into a compound for pharmaceutical use including, e.g., metal salts (sodium, potassium, magnesium, calcium, etc.) and salts of ammonia or organic amines.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular conjugate employed and the effect to be achieved, and the pharnacodynamics associated with each compound in the host.

"Modulate," as used herein, refers to the ability to alter, by increase or decrease (e.g., to act as an, antagonist or agonist).

"Increasing relative delivery" as used herein refers to the effect whereby the accumulation at the intended delivery site (e.g., brain, lysosome) of a RAP-conjugated active agent is increased relative to the accumulation of the unconjugated active agent.

"Therapeutic index" refers to the dose range (amount and/or timing) above the minimum therapeutic amount and below an unacceptably toxic amount.

"Equivalent dose" refers to a dose, which contains the same amount of active agent.

"Polynucleotide" refers to a polymer composed of nucleotide units. Polynucleotides include naturally occurring nucleic acids, such as deoxyribonucleic acid ("DNA") and ribonucleic acid ("RNA") as well as nucleic acid analogs. Nucleic acid analogs include those which include non-naturally occurring bases, nucleotides that engage in linkages with other nucleotides other than the naturally occurring phosphodiester bond or which include bases attached through linkages other than phosphodiester bonds. Thus, nucleotide analogs include, for example and without limitation, phosphorothioates, phosphorodithioates, phosphorotriesters, phosphoramidates, boranophosphates, methylphosphonates, chiral-methyl phosphonates, 2-O-methyl ribonucleotides, peptide-nucleic acids (PNAs), and the like. Such polynucleotides can be synthesized, for example, using an automated DNA synthesizer. The term "nucleic acid" typically refers to large polynucleotides. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

"cDNA" refers to a DNA that is complementary or identical to an mRNA, in either single stranded or double stranded form.

Conventional notation is used herein to describe polynucleotide sequences: the left-hand end of a single-stranded polynucleotide sequence is the 5'-end; the left-hand direction of a double-stranded polynucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand"; sequences on the DNA strand having the same sequence as an mRNA transcribed from that DNA and which are located 5' to the 5'-end of the RNA transcript are referred to as "upstream sequences"; sequences on the DNA strand having the same sequence as the RNA and which are 3' to the 3' end of the coding RNA transcript are referred to as "downstream sequences."

"Complementary" refers to the topological compatibility or matching together of interacting surfaces of two polynucleotides. Thus, the two molecules can be described as complementary, and furthermore, the contact surface characteristics are complementary to each other. A first polynucleotide is complementary to a second polynucleotide if the nucleotide sequence of the first polynucleotide is identical to the nucleotide sequence of the polynucleotide binding partner of the second polynucleotide. Thus, the polynucleotide whose sequence 5'-TATAC-3' is complementary to a polynucleotide whose sequence is 5'-GTATA-3'.

A nucleotide sequence is "substantially complementary" to a reference nucleotide sequence if the sequence complementary to the subject nucleotide sequence is substantially identical to the reference nucleotide sequence.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Recombinant polynucleotide" refers to a polynucleotide having sequences that are not naturally joined together. An amplified or assembled recombinant polynucleotide may be included in a suitable vector, and the vector can be used to transform a suitable host cell. A host cell that comprises the recombinant polynucleotide is referred to as a "recombinant host cell." The gene is then expressed in the recombinant host cell to produce, e.g., a "recombinant polypeptide." A recombinant polynucleotide may serve a non-coding function (e.g., promoter, origin of replication, ribosome-binding site, etc.) as well.

"Expression control sequence" refers to a nucleotide sequence in a polynucleotide that regulates the expression (transcription and/or translation) of a nucleotide sequence operatively linked thereto. "Operatively linked" refers to a functional relationship between two parts in which the activity of one part (e.g., the ability to regulate transcription) results in an action on the other part (e.g., transcription of the sequence). Expression control sequences can include, for example and without limitation, sequences of promoters (e.g., inducible or constitutive), enhancers, transcription terminators, a start codon (i.e., ATG), splicing signals for introns, and stop codons.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in vitro expression system. Expression vectors include all those known in the art, such as cosmids, plasmids (e.g., naked or contained in liposomes) and viruses that incorporate the recombinant polynucleotide.

"Amplification" refers to any means by which a polynucleotide sequence is copied and thus expanded into a larger number of polynucleotide molecules, e.g., by reverse transcription, polymerase chain reaction, and ligase chain reaction.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

"Probe," when used in reference to a polynucleotide, refers to a polynucleotide that is capable of specifically hybridizing to a designated sequence of another polynucleotide. A probe specifically hybridizes to a target complementary polynucleotide, but need not reflect the exact complementary sequence of the template. In such a case, specific hybridization of the probe to the target depends on the stringency of the hybridization conditions. Probes can be labeled with, e.g., chromogenic, radioactive, or fluorescent moieties and used as detectable moieties.

A first sequence is an "antisense sequence" with respect to a second sequence if a polynucleotide whose sequence is the first sequence specifically hybridizes with a polynucleotide whose sequence is the second sequence.

"Hybridizing specifically to" or "specific hybridization" or "selectively hybridize to", refers to the binding, duplexing, or hybridizing of a nucleic acid molecule preferentially to a particular nucleotide sequence under stringent conditions when that sequence is present in a complex mixture (e.g., total cellular) DNA or RNA.

The term "stringent conditions" refers to conditions under which a probe will hybridize preferentially to its target subsequence, and to a lesser extent to, or not at all to, other sequences. "Stringent hybridization" and "stringent hybridization wash conditions" in the context of nucleic acid hybridization experiments such as Southern and Northern hybridizations are sequence dependent, and are different under different environmental parameters. An extensive guide to the hybridization of nucleic acids is found in Tijssen (1993) Laboratory Techniques in Biochemistry and Molecular Biology—Hybridization with Nucleic Acid Probes part I chapter 2 "Overview of principles of hybridization and the strategy of nucleic acid probe assays", Elsevier, N.Y. Generally, highly stringent hybridization and wash conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Very stringent conditions are selected to be equal to the Tm for a particular probe.

An example of stringent hybridization conditions for hybridization of complementary nucleic acids which have more than 100 complementary residues on a filter in a Southern or northern blot is 50% formalin with 1 mg of heparin at 42° C., with the hybridization being carried out overnight. An example of highly stringent wash conditions is 0.15 M NaCl at 72° C. for about 15 minutes. An example of stringent wash conditions is a 0.2×SSC wash at 65° C. for 15 minutes (see, Sambrook, et al. for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. In general, a signal to noise ratio of 2× (or higher) than that observed for an unrelated probe in the particular hybridization assay indicates detection of a specific hybridization.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer. The term "protein" typically refers to large polypeptides. The term "peptide" typically refers to short polypeptides.

Conventional notation is used herein to portray polypeptide sequences: the left-hand end of a polypeptide sequence is the amino-terminus; the right-hand end of a polypeptide sequence is the carboxyl-terminus.

"Conservative substitution" refers to the substitution in a polypeptide of an amino acid with a functionally similar amino acid. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

"Allelic variant" refers to any of two or more polymorphic forms of a gene occupying the same genetic locus. Allelic variations arise naturally through mutation, and may result in phenotypic polymorphism within populations. Gene mutations can be silent (no change in the encoded polypeptide) or may encode polypeptides having altered amino acid sequences. "Allelic variants" also refer to cDNAs derived from mRNA transcripts of genetic allelic variants, as well as the proteins encoded by them.

The terms "identical" or percent "identity," in the context of two or more polynucleotide or polypeptide sequences, refer to two or more sequences or subsequences that are the same or have a specified percentage of nucleotides or amino acid residues that are the same, when compared and aligned for maximum correspondence, as measured using one of the following sequence comparison algorithms or by visual inspection.

The phrase "substantially homologous" or "substantially identical" in the context of two nucleic acids or polypeptides, generally refers to two or more sequences or subsequences that have at least 40%, 60%, 80%, 90%, 95%, 98% nucleotide or amino acid residue identity, when compared and aligned for maximum correspondence, as measured using one of the following sequence comparison algorithms or by visual inspection. Preferably, the substantial identity exists over a region of the sequences that is at least about 50 residues in length, more preferably over a region of at least about 100 residues, and most preferably the sequences are substantially identical over at least about 150 residues. In a most preferred embodiment, the sequences are substantially identical over the entire length of either or both comparison biopolymers.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Natl. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel, et al., supra).

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, J. Mol. Evol. 35:351-360 (1987). The method used is similar to the method described by Higgins & Sharp, CABIOS 5:151-153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps. Another algorithm that is useful for generating multiple alignments of sequences is Clustal W (Thompson, et al. CLUSTAL W: improving the sensitivity of progressive multiple sequence alignment through sequence weighting, positions-specific gap penalties and weight matrix choice, *Nucleic Acids Research* 22: 4673-4680 (1994)).

Another example of algorithm that is suitable for determining percent sequence identity and sequence similarity is the BLAST algorithm, which is described in Altschul, et al., *J. Mol. Biol.* 215:403-410 (1990). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, Proc. Natl. Acad. Sci. USA 89:10915 (1989)).

In addition to calculating percent sequence identity, the BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described herein.

"Substantially pure" or "isolated" means an object species is the predominant species present (i.e., on a molar basis, more abundant than any other individual macromolecular species in the composition), and a substantially purified fraction is a composition wherein the object species comprises at least about 50% (on a molar basis) of all macromolecular species present. Generally, a substantially pure composition means that about 80% to 90% or more of the macromolecular species present in the composition is the purified species of interest. The object species is purified to essential homogeneity (contaminant species cannot be detected in the composition by conventional detection methods) if the composition consists essentially of a single macromolecular species. Solvent species, small molecules (<500 Daltons), stabilizers (e.g., BSA), and elemental ion species are not considered macromolecular species for purposes of this definition. In some embodiments, the conjugates of the invention are substantially pure or isolated. In some embodiments, the conjugates of the invention are substantially pure or isolated with respect to the macromolecular starting materials used in their synthesis. In some embodiments, the pharmaceutical composition of the invention comprises a substantially purified or isolated conjugate of a RAP polypeptide and the active agent admixed with one or more pharmaceutically acceptable excipient.

"Naturally-occurring" as applied to an object refers to the fact that the object can be found in nature. For example, a polypeptide or polynucleotide sequence that is present in an organism (including viruses) that can be isolated from a source in nature and which has not been intentionally modified by man in the laboratory is naturally-occurring.

"Detecting" refers to determining the presence, absence, or amount of an analyte in a sample, and can include quantifying the amount of the analyte in a sample or per cell in a sample.

"Detectable moiety" or a "label" refers to a composition detectable by spectroscopic, photochemical, biochemical, immunochemical, or chemical means. For example, useful labels include $^{32}$P, $^{35}$S, fluorescent dyes, electron-dense reagents, enzymes (e.g., as commonly used in an ELISA), biotin-streptavadin, dioxigenin, haptens and proteins for which antisera or monoclonal antibodies are available, or nucleic acid molecules with a sequence complementary to a target. The detectable moiety often generates a measurable signal, such as a radioactive, chromogenic, or fluorescent signal, that can be used to quantitate the amount of bound detectable moiety in a sample. The detectable moiety can be incorporated in or attached to a primer or probe either covalently, or through ionic, van der Waals or hydrogen bonds, e.g., incorporation of radioactive nucleotides, or biotinylated nucleotides that are recognized by streptavadin. The detectable moiety may be directly or indirectly detectable. Indirect detection can involve the binding of a second directly or indirectly detectable moiety to the detectable moiety. For example, the detectable moiety can be the ligand of a binding partner, such as biotin, which is a binding partner for streptavadin, or a nucleotide sequence, which is the binding partner for a complementary sequence, to which it can specifically hybridize. The binding partner may itself be directly detectable, for example, an antibody may be itself labeled with a fluorescent molecule. The binding partner also may be indirectly detectable, for example, a nucleic acid having a complementary nucleotide sequence can be a part of a branched DNA molecule that is in turn detectable through hybridization with other labeled nucleic acid molecules. (See, e.g., PD. Fahrlander and A. Klausner, Bio/Technology (1988) 6:1165.) Quantitation of the signal is achieved by, e.g., scintillation counting, densitometry, or flow cytometry.

"Linker" refers to a molecule that joins two other molecules, either covalently, or through ionic, van der Waals or hydrogen bonds, e.g., a nucleic acid molecule that hybridizes to one complementary sequence at the 5' end and to another complementary sequence at the 3' end, thus joining two non-complementary sequences.

II. LRP

"LRP" refers to members of the low-density lipoprotein receptor family including the low-density lipoprotein receptor-related protein 1 (LRP1). LRP1 is a large protein of 4525 amino acids (600 kDa), which is cleaved by furin to produce two subunits of 515-(alpha) kDand 85-(β) kDa that remain non-covalently bound. LRP is expressed on most tissue types. Other members of the low-density lipoprotein (LDL) receptor family include LDL-R (132 kDa); LRP/LRP1 and LRP1B (600 kDa); Megalin ((LRP2), 600 kDa); VLDL-R (130 kDa); ER-2 (LRP-8, 130 kDa); Mosaic LDL-R (LR11, 250 KDa); and other members such as LRP3, LRP6, and LRP-7. Characteristic features of the family include cell-surface expression; extracellular ligand binding domain repeats (DxSDE); requirement of Ca++ for ligand binding; recognition of RAP and ApoE; EGF precursor homology domain repeats (YWTD); single membrane spanning region; internalization signals in the cytoplasmic domain (FDNPXY); and receptor mediated endocytosis of various ligands. Some members of the family, including LRP1 and VLDLR, participate in signal transduction pathways.

LRP ligands refer to a number of molecules that are known to bind LRP. These molecules include, for instance, lactoferrin, RAP, lipoprotein lipase, ApoE, Factor VIII, beta-amyloid precursor, alpha-2-macroglobulin, thrombospondin 2 MMP-2 (matrix metalloproteinase-2), MPP-TIMP-1 (tissue inhibitor of matrix metalloproteinase-1); uPA (urokinase plasminogen activator):PAI-I (plasminogen activator inhibitor-1):uPAR (uPA receptor); and tPA (tissue plasminogen activator):PAI-1:uPAR.

LRP1 is believed to be a multifunctional receptor with clustering of cysteine-rich type repeats. A binding repeat, resembling those found in the LDL receptor, is the molecular principle for the ability to bind a variety of ligands that were previously thought to be unrelated. These include the ligands described in the previous paragraph in addition to: pseudomonas exotoxin A, human rhinovirus, lactoferrin and the so-called receptor associated protein (RAP). See, Meilinger, et al., *FEBS Lett*, 360:70-74 (1995). LRP1 is has the GenBank Accession No.: X 13916 and SwissProt Primary Accession No.: Q07954. Alternative names for the LRP1 gene/protein include: Low-density lipoprotein receptor-related protein 1 [precursor], LRP, Alpha-2-macroglobulin receptor, A2MR, Apolipoprotein E receptor, APOER, CD91, LRP1 or A2MR.

Members of the LRP family are well expressed on capillary endothelium and on CNS cell types including neurons and astrocytes (e.g., LDL receptor, Megalin, LRP). LRP receptors endocytose bound ligand and have been demonstrated to transcytose ligands across polarized epithelial cells in the kidney, thyroid and across capillary endothelial cells in the brain. LRP therefore comprises a pool of compositionally and functionally related receptors expressed at different levels in different tissues. In some embodiments, this invention uses RAP, which binds and thereby targets members of this pool of related receptors (and particularly cells, tissues, and organs expressing a member of this pool). Examples include the VLDLR on muscle tissue, LRP1B on neuronal tissue, Megalin on both kidney and neuronal tissue and LRP1 on vascular smooth muscle tissue.

III. RAP

"RAP" is a well-known protein of about 39 kDa and 323 amino acids and is a specialized chaperone for members of the LRP family. RAP inhibits the binding of ligand to members of the LDL-receptor family such as LRP (see Bu, G. & Rennke, S. J. Biol. Chem. 271: 22218-2224 (1996); Willnow, T. E, Goldstein, J. L., Orth, K., Brown, M. S. & Herz, J. J. Biol. Chem. 267: 26172-26180 (1992); Bu, G. & Schwartz, A. L. Trends Cell Biol. 8: 272-276 (1998); and Herz, J. & Strickland, D. K. J. Clin. Invest. 108: 779-784 (2001). See also, Bu and Schwartz, (1998). Further characterization of RAP, including the complete amino acid sequence of human RAP (FIG. 15), is found in U.S. Pat. No. 5,474,766 which is incorporated herein by reference in its entirety and also with particularity with respect to the RAP amino acid sequences and fragments disclosed therein. The 28 kDa human C-terminal fragment (FIG. 16) is an extremely active RAP polypeptide and in preferred embodiments of the invention, the conjugate comprises this fragment as the carrier for the active agent.

RAP polypeptides include, but are not limited to, RAP, soluble forms of RAP, cleaved RAP, RAP polypeptide fragments, homologues and analogs of RAP, and the like. RAP polypeptides that are functional equivalents of RAP with respect to modulation of LRP receptor binding, transcytosis, or endocytosis can be readily identified by screening for the ability of the RAP polypeptide to bind to LRP. In preferred embodiments, the RAP polypeptide is a homologue of RAP having, for instance, greater than 80%, 90% 95%, 98%, or 99% sequence identity with a naturally occurring, native or wild type mammalian RAP amino acid sequence of similar length or over a domain of at least 10 amino acids, 25 amino acids, 50 amino acids, 100 amino acids, or 200 amino acids, 300 amino acids, or the entire length of the RAP polypeptide. RAP polypeptides include allelic variants of RAP, paralogs and orthologs in human, mouse, rat, chicken, zebrafish, pig, fruit fly, mosquito, and flatworm native RAP, and derivatives, portions, or fragments thereof (Genbank accession numbers: P30533 (human), XP132029 (mouse), Q99068 (rat), CAA05085 (chicken), AAH49517 (zebrafish), AAM90301 (pig), NP649950 (fruit fly), XP313261 (mosquito), NP506187 (flatworm). A multiple alignment of amino acid sequences from mouse, rat, chicken zebrafish, fruitfly, mosquito, and flatworm and the consensus sequence is shown in FIG. 14.

The RAP polypeptide can be in the form of acidic or basic salts, or in its neutral form. In addition, individual amino acid residues can be modified, such as by oxidation or reduction. Moreover, various substitutions, deletions, or additions can be made to the amino acid or nucleic acid sequences, the net effect of which is to retain or improve upon the desired biological activity of RAP. Further characterization of RAP, including the complete amino acid sequence of RAP, is found in U.S. Pat. No. 5,474,766 which is incorporated herein by reference in its entirety and also with particularity with respect to the amino acid sequences of the various RAP polypeptides disclosed therein. Due to code degeneracy, for example, one of ordinary skill in the art would know of considerable variations of the nucleotide sequences encoding the same amino acid sequence.

Preferred RAP polypeptides share substantial homology with the native amino acid sequence of a receptor associated protein (RAP), particularly the native human sequence (SEQ ID NO:1). In preferred embodiments, the RAP polypeptide is a homologue of RAP having, for instance, greater than 80%, 90% 95%, 98%, or 99% sequence identity with a native or wild type mammalian RAP amino acid sequence of similar length or over a domain or comparison window of at least 10, amino acids, 25 amino acids, 50 amino acids, 100 amino acids, or 200 amino acids, or 300 amino acids or more.

An especially preferred human or mammalian RAP is isolated RAP or a fragment thereof, such as a soluble polypeptide fragment of RAP, which contains at least one of the RAP binding sites for LRP. Substantial guidance exists in the art to which portions of RAP are important to its LRP binding and modulatory activity and which portions may be mutated, altered, or deleted without loss of binding activity (see, Nielsen et al. *Proc. Nat. Acad. Sci. USA* 94:7521 (1997); and Rall et al. *J. Biol. Chem.* 273(37):24152(1998)). For instance, RAP's LRP binding function has been mapped by performing direct binding studies on fusion proteins representing overlapping domains of RAP (see Willnow et al., *J. Biol. Chem.* 267(36):26172-80 (1992). The RAP binding motifs have also been characterized by use of truncated and site-directed RAP mutants (see Melman et al. *J. Biol. Chem.* 276(31):29338-29346 (2001). Particular RAP polypeptide fragments, suitable for use according to the invention, include fragments (defined from RAP N terminus amino acid to RAP C-terminus amino acid position) 1-323 (RAP); 1-319; 1-250; 1-110; 91-210; 191-323; 221-323; 1-190; 1-200; and 1-210. Preferred RAP polypeptides include fragments 1-323 (RAP); 1-319; 191-323; and 1-210. A modified RAP polypeptide having the C-terminal four amino acid sequence substituted by the sequence KDEL is also suitable. A modified RAP polypeptide in which the C-terminal-four amino acid sequence (HNEL) is deleted is also suitable. Also preferred are RAP polypeptides fragments that comprise the native sequence of RAP from amino acid 201 to 210.

Other preferred embodiments, comprise a human or mammalian RAP polypeptide in which the polypeptide comprises the native amino acid sequence of RAP over positions 282-289, 201-210, and 311-319. Mutated and N-terminus or C-terminus truncated variants of RAP which bind to the LRP receptor are disclosed in Melman et al., 2001) which is incorporated herein by reference in its entirety and with particularity to these RAP mutated and truncated variants. Other preferred RAP polypeptides comprise a native sequence of RAP between amino acids 85-148 and 178-248. (see Farquhar, et al., *Proc. Nat. Acad Sci. USA* 91:3161-3162 (1994).

Thus, many references disclose the binding sites and structure activity relationships for binding of RAP and RAP fragments to the LRP receptor. The skilled artisan can readily adapt a variety of well known techniques in the art in order to obtain RAP polypeptides that contain a LRP binding site and are suitable for use as RAP polypeptides according to the invention. The preferred fragments of RAP are soluble under physiological conditions. The N-terminus or C-terminus of these polypeptides can be shortened as desired, provided that the binding capacity for the LRP particle remains intact. The preferred amino acid sequence of RAP corresponds to the human protein. Suitable sequences for a RAP polypeptide can also be derived from the amino acid sequences of RAP isolated from other mammals or members of the kingdom Animalia.

In order to generate fragments of RAP which contains the LRP binding site, isolated native protein may be converted by enzymatic and/or chemical cleavage to generate fragments of the whole protein, for example by reacting RAP with an enzyme such as papain or trypsin or a chemical such as cyanogen bromide. Proteolytically active enzymes or chemicals are preferably selected in order to release the extracellular receptor region. Fragments that contain the LRP binding site, especially fragments that are soluble under physiological conditions, can then be isolated using known methods.

Alternatively, RAP or a fragment of RAP may be expressed in a recombinant bacteria, as described, for example, in Williams et al., *J. Biol. Chem.* 267:9035-9040 (1992); Wurshawsky et al., *J. Biol. Chem.* 269:3325-3330 (1994); Melman et al. *J. Biol. Chem.* 276(31): 29338-46 (2001).

RAP can be in the form of acidic or basic salts, or in neutral forms. In addition, individual amino acid residues can be modified, such as by oxidation or reduction. Moreover, various substitutions, deletions, or additions can be made to the amino acid or nucleic acid sequences, the net effect of which is to retain or improve upon the desired biological activity of RAP. Due to code degeneracy, for example, there may be considerable variation in nucleotide sequences encoding the same amino acid sequence.

A RAP fragment as used herein includes, but not limited to, any portion of RAP or its biologically equivalent analogs that contains a sufficient portion of the ligand to enable it to bind to LRP and to be transcytosed, transported across the blood-brain barrier; or that otherwise retains or improves upon the desired LRP mediated carrier activities of the ligand.

FIG. 15 shows the amino acid sequence of human RAP.

FIG. 16 shows the amino acid sequence of the 28 kd RAP polypeptide.

IV. RAP-conjugates

A "RAP-conjugate" or "RAP-polypeptide conjugate" each refers to a compound comprising RAP or a RAP polypeptide, or a fragment thereof, attached to an active agent. As used herein, the term "conjugated" means that the therapeutic agent(s) and RAP or the RAP polypeptide are physically linked by, for example, by covalent chemical bonds, physical forces such van der Waals or hydrophobic interactions, encapsulation, embedding, or combinations thereof. In preferred embodiments, the therapeutic agent(s) and the RAP polypeptide are physically linked by covalent chemical bonds. As such, preferred chemotherapeutic agents contain a functional group such as an alcohol, acid, carbonyl, thiol or amine group to be used in the conjugation to RAP or the RAP polypeptide. Adriamycin is in the amine class and there is also the possibility to link through the carbonyl as well. Paclitaxel is in the alcohol class. Chemotherapeutic agents without suitable conjugation groups may be further modified to add such a group. All these compounds are contemplated in this invention. In the case of multiple therapeutic agents, a combination of various conjugations can be used.

In some embodiments, a covalent chemical bond that may be either direct (no intervening atoms) or indirect (through a linker e.g., a chain of covalently linked atoms) joins the RAP polypeptide and the active agent. In preferred embodiments, the RAP or RAP polypeptide moiety and the active agent moiety of the conjugate are directly linked by covalent bonds between an atom of the RAP polypeptide and an atom of the active agent. In some preferred embodiments, the RAP moiety is connected to the active agent moiety of the compound according to the invention by a linker which comprises a covalent bond or a peptide of virtually any amino acid sequence or any molecule or atoms capable of connecting RAP or the RAP polypeptide to the active agent.

In some embodiments, the linker comprises a chain of atoms from 1 to about 30 atoms or longer, 2 to 5 atoms, 2 to 10 atoms, 5 to 10 atoms, or 10 to 20 atoms long. In some embodiments, the chain atoms are all carbon atoms. In some embodiments, the chain atoms are selected from the group consisting of C, O, N, and S. Chain atoms and linkers may be selected according to their expected solubility (hydrophilicity) so as to provide a more soluble conjugate. In some embodiments, the linker provides a functional group that is subject to enzymatic attack in a lysosome. In some embodiments, the linker provides a functional group which is subject to attack by an enzyme found in the target tissue or organ and which upon attack or hydrolysis severs the link between the active agent and the RAP polypeptide. In some embodiments, the linker provides a functional group that is subject to hydrolysis under the conditions found at the target site (e.g., low pH of a lysosome). A linker may contain one or more such functional groups. In some embodiments, the length of the linker is long enough to reduce the potential for steric hindrance (when an active agent is large) between one or both of the RAP polypeptide binding site and the active agent active binding site.

If the linker is a covalent bond or a peptide and the active agent is a polypeptide, then the entire conjugate can be a fusion protein. Such fusion proteins may be produced by recombinant genetic engineering methods known to one of ordinary skill in the art. In some embodiments, the RAP fragment degrades quickly to release the active compound. In other embodiments, the linker is subject to cleavage under intracellular, or more preferably, lysosomal environmental conditions to release or separate the active agent portion from the RAP polypeptide portion.

The conjugate can comprise one or more active agents linked to the same RAP polypeptide. For example, conjugation reactions may conjugate from 1 to 5, about 5, about 1 to 10, about 5 to 10, about 10 to 20, about 20 to 30, or 30 or more molecules of an active agent to the RAP polypeptide. These formulations can be employed as mixtures, or they may be purified into specific stoichiometric formulations. Those skilled in the art are able to determine which format and which stoichiometric ratio is preferred. Further, more than one type of active agent may be linked to the RAP polypeptide where delivery of more than one type of an agent to a target site or compartment is desired. A plurality of active agent species may be attached to the same RAP polypeptide e.g., adriamycin-cisplatinum RAP polypeptide conjugates. Thus, the conjugates may consist of a range of stoichiometric ratios and incorporate more than one type of active agent. These, too, may be separated into purified mixtures or they may be employed in aggregate.

The RAP or RAP polypeptide conjugate according to the invention may be modified as desired to enhance its stability or pharmacokinetic properties (e.g., PEGylation). Suitable linkers and their functional groups for conjugating RAP polypeptides and an active agent, and the synthetic chemical methods readily adaptable for preparing such, are described in U.S. Patent Application No. 60/395,762 which is assigned to the same assignee as the present application and herein incorporated by reference in its entirety.

The synthesis of these conjugates is efficient and convenient, producing high yields and drugs with enhanced aqueous solubility.

V. Active Agents

Active agents according to the invention include agents that can affect a biological process. Particularly preferred active agents for use in the compounds compositions and methods of the invention are therapeutic agents, including drugs and diagnostic agents. The term "drug" or "therapeutic agent" refers to an active agent that has a pharmacological activity or benefits health when administered in a therapeutically effective amount. Particularly preferred agents are naturally occurring biological agents (e.g., enzymes, proteins, polynucleotdies, antibodies, poiypeptides). In some embodiments, the active agent conjugated to RAP or RAP polypeptide is a molecule, as well as any binding portion or fragment thereof, that is capable of modulating a biological process in a living host. Examples of drugs or therapeutic agents include substances that are used in the prevention, diagnosis, alleviation, treatment or cure of a disease or condition.

A. Protein Active Agents

The active agent can be a non-protein or a protein. The active agent can be a protein or enzyme or any fragment of such that still retains some, substantially all, or all of the therapeutic or biological activity of the protein or enzyme. In some embodiments, the protein or enzyme is one that, if not expressed or produced or if substantially reduced in expression or production, would give rise to a disease, including but not limited to, lysosomal storage diseases. Preferably, the protein or enzyme is derived or obtained from a human or mouse.

If the compound is a protein, the compound can be an enzyme, or any fragment of an enzyme that still retains some, substantially all, or all of the activity of the enzyme. Preferably, in the treatment of lysosomal storage diseases, the enzyme is an enzyme that is found in a cell that if not expressed or produced or is substantially reduced in expression or production would give rise to a lysosomal storage disease. Preferably, the enzyme is derived or obtained from a human or mouse. Preferably, the enzyme is a lysosomal storage enzyme, such as α-L-iduronidase, iduronate-2-sulfatase, heparan N-sulfatase, α-N-acetylglucosaminidase, arylsulfatase A, galactosylceramidase, acid-alpha-glucosidase, tripeptidyl peptidase, hexosaminidase alpha, acid sphingomyelinase, α-galactosidase, or any other lysosomal storage enzyme.

In some embodiments, therefore, in the treatment of human Lysosomal Storage Diseases (LSDs), the RAP polypeptide-active agent conjugate comprises an active agent protein or enzyme that is deficient in the lysosomes of a subject or patient to be treated. Such enzymes, include for example, alpha-L-iduronidase, iduronate-2-sulfatase, heparan N-sulfatase, alpha-N-acetylglucosaminidase, Arylsulfatase A, Galactosylceramidase, acid-alpha-glucosidase, thioesterase, hexosaminidase A, Acid Spingomyelinase, alpha-galactosidase, or any other lysosomal storage enzyme. A table of lysosomal storage diseases and the proteins deficient therein, which are useful as active agents, follows:

| Lysosomal Storage Disease | Protein deficiency |
| --- | --- |
| Mucopolysaccharidosis type I | L-Iduronidase |
| Mucopolysaccharidosis type II Hunter syndrome | Iduronate-2-sulfatase |
| Mucopolysaccharidosis type IIIA Sanfilippo syndrome | Heparan-N-sulfatase |
| Mucopolysaccharidosis type IIIB Sanfilippo syndrome | α-N-Acetylglucosaminidase |
| Mucopolysaccharidosis type IIIC Sanfilippo syndrome | AcetylCoA:N-acetyltransferase |
| Mucopolysaccharidosis type IIID Sanfilippo syndrome | N-Acetylglucosamine 6-sulfatase |
| Mucopolysaccharidosis type IVA Morquio syndrome | Galactose 6-sulfatase |
| Mucopolysaccharidosis type IVB Morquio syndrome | β-Galactosidase |
| Mucopolysaccharidosis type VI | N-Acetylgalactosamine 4-sulfatase |
| Mucopolysaccharidosis type VII Sly syndrome | β-Glucuronidase |
| Mucopolysaccharidosis type IX | hyaluronoglucosaminidase |
| Aspartylglucosaminuria | Aspartylglucosaminidase |
| Cholesterol ester storage disease/Wolman disease | Acid lipase |
| Cystinosis | Cystine transporter |
| Danon disease | Lamp-2 |
| Fabry disease | α-Galactosidase A |
| Farber Lipogranulomatosis/Farber disease | Acid ceramidase |
| Fucosidosis | α-L-Fucosidase |
| Galactosialidosis types I/II | Protective protein |
| Gaucher disease types I/IIIII Gaucher disease | Glucocerebrosidase (β-glucosidase) |
| Globoid cell leukodystrophy/Krabbe disease | Galactocerebrosidase |
| Glycogen storage disease II/Pompe disease | α-Glucosidase |
| GM1-Gangliosidosis types I/II/III | β-Galactosidase |
| GM2-Gangliosidosis type I/Tay Sachs disease | β-Hexosaminidase A |
| GM2-Gangliosidosis type II Sandhoff disease | β-Hexosaminidase A |
| GM2-Gangliosidosis | GM2-activator deficiency |
| α-Mannosidosis types I/II | α-D-Mannosidase |
| β-Mannosidosis | β-D-Mannosidase |
| Metachromatic leukodystrophy | Arylsulfatase A |
| Metachromatic leukodystrophy | Saposin B |
| Mucolipidosis type I/Sialidosis types I/II | Neuraminidase |
| Mucolipidosis types II/III I-cell disease | Phosphotransferase |
| Mucolipidosis type IIIC pseudo-Hurler polydystrophy | Phosphotransferase γ-subunit |
| Multiple sulfatase deficiency | Multiple sulfatases |
| Neuronal Ceroid Lipofuscinosis, CLN1 Batten disease | Palmitoyl protein thioesterase |
| Neuronal Ceroid Lipofuscinosis, CLN2 Batten disease | Tripeptidyl peptidase I |
| Niemann-Pick disease types A/B Niemann-Pick disease | Acid sphingomyelinase |
| Niemann-Pick disease type C1 Niemann-Pick disease | Cholesterol trafficking |
| Niemann-Pick disease type C2 Niemann-Pick disease | Cholesterol trafficking |
| Pycnodysostosis | Cathepsin K |
| Schindler disease types I/II Schindler disease | α-Galactosidase B |
| Sialic acid storage disease | sialic acid transporter |

Thus, the lysosomal storage diseases that can be treated or prevented using the methods of the present invention include, but are not limited to, Mucopolysaccharidosis I (MPS I), MPS II, MPS IIIA, MPS IIIB, Metachromatic Leukodystrophy (MLD), Krabbe, Pompe, Ceroid Lipofuscinosis, Tay-Sachs, Niemann-Pick A and B, and other lysosomal diseases.

Thus, per the above table, for each disease the conjugated agent would preferably comprise a specific active agent enzyme deficient in the disease. For instance, for methods involving MPS I, the preferred compound or enzyme is α-L-iduronidase. For methods involving MPS II, the preferred compound or enzyme is iduronate-2-sulfatase. For methods involving MPS IIIA, the preferred compound or enzyme is heparan N-sulfatase. For methods involving MPS IIIB, the preferred compound or enzyme is α-N-acetylglucosaminidase. For methods involving Metachromatic Leukodystropy (MLD), the preferred compound or enzyme is arylsulfatase A. For methods involving Krabbe, the preferred compound or enzyme is galactosylceramidase. For methods involving Pompe, the preferred compound or enzyme is acid α-glucosidase. For methods involving CLN, the preferred compound or enzyme is tripeptidyl peptidase. For methods involving Tay-Sachs, the preferred compound or enzyme is hexosaminidase alpha. For methods involving Niemann-Pick A and B the preferred compound or enzyme is acid sphingomyelinase.

The RAP or RAP polypeptide active agent conjugate can comprise one or more agent moieties (e.g., 1 to 10 or 1 to 4 or 2 to 3 moieties) linked to RAP or a RAP polypeptide. For example, conjugation reactions may conjugate from 1 to 4 or more molecules of alpha-L-iduronidase to a single RAP polypeptide molecule. These formulations can be employed as mixtures, or they may be purified into specific RAP polypeptide-agent stoichiometric formulations. Those skilled in the art are able to determine which format and which stoichiometric ratio is preferred. Further, one or more different active agents may be linked to RAP or the RAP polypeptide to facilitate a more complete degradation of the stored substrates. These RAP or RAP polypeptide conjugated agents may consist of a range of stoichiometric ratios. These, too, may be separated into purified mixtures or they may be employed in aggregate.

The RAP or RAP polypeptide conjugated active agents can enter or be transported into or end up residing in the lysosomes of a cell within or without the CNS. The rate of passage of the conjugated agent can be modulated by any compound or protein that can modulate LRP binding activity. The cell can be from any tissue or organ system affected by the lysosomal storage disease. The cell can be, for instance, an endothelial, epithelial, muscle, heart, bone, lung, fat, kidney, or liver cell. In some embodiments, the cell is preferably a cell found within the BBB. In some embodiments, the cell is a neuron or a brain cell. In other embodiments, the cell is a cell of the periphery or one that is not isolated from the general circulation by an endothelium such as that of the BBB.

B. Drug Active Agents

Generally, the drug active agent may be of any size. Preferred drugs are small organic molecules that are capable of binding to the target of interest. A drug moiety of the conjugate, when a small molecule, generally has a molecular weight of at least about 50 D, usually at least about 100 D, where the molecular weight may be as high as 500 D or higher, but will usually not exceed about 2000 D.

The drug moiety is capable of interacting with a target in the host into which the conjugate is administered during practice of the subject methods. The target may be a number of different types of naturally occurring structures, where targets of interest include both intracellular and extracellular targets, where such targets may be proteins, phospholipids, nucleic acids and the like, where proteins are of particular interest. Specific proteinaceous targets of interest include, without limitation, enzymes, e.g., kinases, phosphatases, reductases, cyclooxygenases, proteases and the like, targets comprising domains involved in protein-protein interactions, such as the SH2, SH3, PTB and PDZ domains, structural proteins, e.g., actin, tubulin, etc., membrane receptors, immunoglobulins, e.g., IgE, cell adhesion receptors, such as integrins, etc, ion channels, transmembrane pumps, transcription factors, signaling proteins, and the like.

In some embodiments, the active agent or drug has a hydroxyl or an amino group for reacting with the isocyanate reagent or the active agent is chemically modified to introduce a hydroxyl or an amino group for reacting with the isocyanate reagent.

In some embodiments, the active agent or drug comprises a region that may be modified and/or participate in covalent linkage, preferably, without loss of the desired biological activity of the active agent. The drug moieties often comprise cyclical carbon or heterocyclic structures and/or aromatic or polyaromatic structures substituted with one or more of the above functional groups. Also of interest as drug moieties are structures found among biomolecules, proteins, enzymes, polysaccharides, and polynucleic acids, including peptides, saccharides, fatty acids, steroids, purines, pyrimidines, derivatives, structural analogs or combinations thereof.

Suitable active agents include, but are not limited to, psychopharmacological agents, such as (1) central nervous system depressants, e.g., general anesthetics (barbiturates, benzodiazepines, steroids, cyclohexanone derivatives, and miscellaneous agents), sedative-hypnotics (benzodiazepines, barbiturates, piperidinediones and triones, quinazoline derivatives, carbamates, aldehydes and derivatives, amides, acyclic ureides, benzazepines and related drugs, phenothiazines, etc.), central voluntary muscle tone modifying drugs (anticonvulsants, such as hydantoins, barbiturates, oxazolidinediones, succinimides, acylureides, glutarimides, benzodiazepines, secondary and tertiary alcohols, dibenzazepine derivatives, valproic acid and derivatives, GABA analogs, etc.), analgesics (morphine and derivatives, oripavine derivatives, morphinan derivatives, phenylpiperidines, 2,6-methane-3-benzazocaine derivatives, diphenylpropylamines and isosteres, salicylates, p-aminophenol derivatives, 5-pyrazolone derivatives, arylacetic acid derivatives, fenamates and isosteres, etc.) and antiemetics (anticholinergics, antihistamines, antidopaminergics, etc.), (2) central nervous system stimulants, e.g., analeptics (respiratory stimulants, convulsant stimulants, psychomotor stimulants), narcotic antagonists (morphine derivatives, oripavine derivatives, 2,6-methane-3-benzoxacine derivatives, morphinan derivatives) nootropics, (3) psychopharmacologicals, e.g., anxiolytic sedatives (benzodiazepines, propanediol carbamates) antipsychotics (phenothiazine derivatives, thioxanthine derivatives, other tricyclic compounds, butyrophenone derivatives and isosteres, diphenylbutylamine derivatives, substituted benzamides, arylpiperazine derivatives, indole derivatives, etc.), antidepressants (tricyclic compounds, MAO inhibitors, etc.), (4) respiratory tract drugs, e.g., central antitussives (opium alkaloids and their derivatives); pharmacodynamic agents, such as (1) peripheral nervous system drugs, e.g., local anesthetics (ester derivatives, amide derivatives), (2) drugs acting at synaptic or neuroeffector junctional sites, e.g., cholinergic agents, cholinergic blocking agents, neuromuscular blocking agents, adrenergic agents, antiadrenergic agents, (3) smooth muscle active drugs, e.g., spasmolytics (anticholinergics, musculotropic spasmolytics), vasodilators, smooth muscle stimulants, (4) histamines and antihistamines, e.g., histamine and derivative thereof (betazole), antihistamines ($H_1$-antagonists, $H_2$-antagonists), histamine metabolism drugs, (5) cardiovascular drugs, e.g., cardiotonics (plant extracts, butenolides, pentadienolids, alkaloids from erythrophleum species, ionophores, adrenoceptor stimulants, etc), antiarrhythmic drugs, antihypertensive agents, antilipidemic agents (clofibric acid derivatives, nicotinic acid derivatives, hormones and analogs, antibiotics, salicylic acid and derivatives), antivaricose drugs, hemostyptics, (6) blood and hemopoietic system drugs, e.g., antianemia drugs, blood coagulation drugs (hemostatics, anticoagulants, antithrombotics, thrombolytics, blood proteins and their fractions), (7) gastrointestinal tract drugs, e.g., digestants (stomachics, choleretics), antiulcer drugs, antidiarrheal agents, (8) locally acting drugs; chemotherapeutic agents, such as (1) anti-infective agents, e.g., ectoparasiticides (chlorinated hydrocarbons, pyrethins, sulfurated compounds), anthelmintics, antiprotozoal agents, antimalarial agents, antiamebic agents, antileiscmanial drugs, antitrichomonal agents, antitrypanosomal agents, sulfonamides, antimycobacterial drugs, antiviral chemotherapeutics, etc., and (2) cytostatics, i.e., antineoplastic agents or cytotoxic drugs, such as alkylating agents, e.g., Mechlorethamine hydrochloride (Nitrogen Mustard, Mustargen, HN2), Cyclophosphamide (Cytovan, Endoxana), Ifosfamide (IFEX), Chlorambucil (Leukeran), Melphalan (Phenylalanine Mustard, L-sarcolysin, Alkeran, L-PAM), Busulfan (Myleran), Thiotepa (Triethylenethiophosphoramide), Carmustine (BiCNU, BCNU), Lomustine (CeeNU, CCNU), Streptozocin (Zanosar) and the like; plant alkaloids, e.g., Vincristine (Oncovin), Vinblastine (Velban, Velbe), Paclitaxel (Taxol), and the like; antimetabolites, e.g., Methotrexate (MTX), Mercaptopurine (Purinethol, 6-MP), Thioguanine (6-TG), Fluorouracil (5-FU), Cytarabine (Cytosar-U, Ara-C), Azacitidine (Mylosar, 5-AZA) and the like; antibiotics, e.g., Dactinomycin (Actinomycin D, Cosmegen), Doxorubicin (Adriamycin), Daunorubicin (duanomycin, Cerubidine), Idarubicin (Idamycin), Bleomycin (Blenoxane), Picamycin (Mithramycin, Mithracin), Mitomycin (Mutamycin) and the like, and other anticellular proliferative agents, e.g., Hydroxyurea (Hydrea), Procarbazine (Mutalane), Dacarbazine (DTIC-Dome), Cisplatin (Platinol) Carboplatin (Paraplatin), Asparaginase (Elspar) Etoposide (VePesid, VP-16-213), Amsarcrine (AMSA, m-AMSA), Mitotane (Lysodren), Mitoxantrone (Novatrone), and the like. Preferred chemotherapeutic agents are those, which in the free form, demonstrate unacceptable systemic toxicity at desired doses. The general systemic toxicity associated with therapeutic levels of such agents may be reduced by their linkage to RAP or a RAP polypeptide. Particularly preferred are cardiotoxic compounds that are useful therapeutics but are dose limited by cardiotoxicity. A classic example is adriamycin (also known as doxorubicin) and its analogs, such as daunorubicin. Linking RAP or a RAP polypeptide to such drugs may prevent accumulation and associated cardiotoxicity at the heart.;

Suitable active agents include, but are not limited to: Antibiotics, such as: aminoglycosides, e.g., amikacin, apramycin, arbekacin, bambermycins, butirosin, dibekacin, dihydrostreptomycin, fortimicin, gentamicin, isepamicin, kanamycin, micronomcin, neomycin, netilmicin, paromycin, ribostamycin, sisomicin, spectinomycin, streptomycin, tobramycin, trospectomycin; amphenicols, e.g., azidamfenicol, chloramphenicol, florfenicol, and theimaphenicol; ansamycins, e.g., rifamide, rifampin, rifamycin, rifapentine, rifaximin; beta-lactams, e.g., carbacephems, carbapenems, cephalosporins, cehpamycins, monobactams, oxaphems, penicillins; lincosamides, e.g., clinamycin, lincomycin; macrolides, e.g., clarithromycin, dirthromycin, erythromycin, etc.; polypeptides, e.g., amphomycin, bacitracin, capreomycin, etc.; tetracyclines, e.g., apicycline, chlortetracycline, clomocycline, etc.; synthetic antibacterial agents, such as 2,4-diaminopyrimidines, nitrofurans, quinolones and analogs thereof, sulfonamides, sulfones;

Suitable active agents include, but are not limited to: Antifungal agents, such as: polyenes, e.g., amphotericin B, candicidin, dermostatin, filipin, fungichromin, hachimycin, hamycin, lucensomycin, mepartricin, natamycin, nystatin, pecilocin, perimycin; synthetic antifungals, such as allylamines, e.g., butenafine, naftifine, terbinafine; imidazoles, e.g., bifonazole, butoconazole, chlordantoin, chlormidazole, etc., thiocarbamates, e.g., tolciclate, triazoles, e.g., fluconazole, itraconazole, terconazole;

Suitable active agents include, but are not limited to: Antihelmintics, such as: arecoline, aspidin, aspidinol, dichlorophene, embelin, kosin, napthalene, niclosamide, pelletierine, quinacrine, alantolactone, amocarzine, amoscanate, ascaridole, bephenium, bitoscanate, carbon tetrachloride, carvacrol, cyclobendazole, diethylcarbamazine, etc.;

Suitable active agents include, but are not limited to: Antimalarials, such as: acedapsone, amodiaquin, arteether, artemether, artemisinin, artesunate, atovaquone, bebeerine, berberine, chirata, chlorguanide, chloroquine, chlorprogaunil, cinchona, cinchonidine, cinchonine, cycloguanil, gentiopicrin, halofantrine, hydroxychloroquine, mefloquine hydrochloride, 3-methylarsacetin, pamaquine, plasmocid, primaquine, pyrimethamine, quinacrine, quinidine, quinine, quinocide, quinoline, dibasic sodium arsenate;

Suitable active agents include, but are not limited to: Antiprotozoan agents, such as: acranil, tinidazole, ipronidazole, ethylstibamine, pentamidine, acetarsone, aminitrozole, anisomycin, nifuratel, tinidazole, benzidazole, suramin, and the like.

Suitable drugs for use as active agents are also listed in: Goodman & Gilman's, The Pharmacological Basis of Therapeutics (9th Ed) (Goodman et al. eds) (McGraw-Hill) (1996); and 1999 Physician's Desk Reference (1998).

Suitable active agents include, but are not limited to: antineoplastic agents, as disclosed in U.S. Pat. Nos. 5,880,161, 5,877,206, 5,786,344, 5,760,041, 5,753,668, 5,698,529, 5,684,004, 5,665,715, 5,654,484, 5,624,924, 5,618,813, 5,610,292, 5,597,831, 5,530,026, 5,525,633, 5,525,606, 5,512,678, 5,508,277, 5,463,181, 5,409,893, 5,358,952, 5,318,965, 5,223,503, 5,214,068, 5,196,424, 5,109,024, 5,106,996, 5,101,072, 5,077,404, 5,071,848, 5,066,493, 5,019,390, 4,996,229, 4,996,206, 4,970,318, 4,968,800, 4,962,114, 4,927,828, 4,892,887, 4,889,859, 4,886,790, 4,882,334, 4,882,333, 4,871,746, 4,863,955, 4,849,563, 4,845,216, 4,833,145, 4,824,955, 4,785,085, 4,684,747, 4,618,685, 4,611,066, 4,550,187, 4,550,186, 4,544,501, 4,541,956, 4,532,327, 4,490,540, 4,399,283, 4,391,982, 4,383,994, 4,294,763, 4,283,394, 4,246,411, 4,214,089, 4,150,231, 4,147,798, 4,056,673, 4,029,661, 4,012,448;

psychopharmacological/psychotropic agents, as disclosed in U.S. Pat. Nos. 5,192,799, 5,036,070, 4,778,800, 4,753,951, 4,590,180, 4,690,930, 4,645,773, 4,427,694, 4,424,202, 4,440,781, 5,686,482, 5,478,828, 5,461,062, 5,387,593, 5,387,586, 5,256,664, 5,192,799, 5,120,733, 5,036,070, 4,977,167, 4,904,663, 4,788,188, 4,778,800, 4,753,951, 4,690,930, 4,645,773, 4,631,285, 4,617,314, 4,613,600, 4,590,180, 4,560,684, 4,548,938, 4,529,727, 4,459,306, 4,443,451, 4,440,781, 4,427,694, 4,424,202, 4,397,853, 4,358,451, 4,324,787, 4,314,081, 4,313,896, 4,294,828, 4,277,476, 4,267,328, 4,264,499, 4,231,930, 4,194,009, 4,188,388, 4,148,796, 4,128,717, 4,062,858, 4,031,226, 4,020,072, 4,018,895, 4,018,779, 4,013,672, 3,994,898, 3,968,125, 3,939,152, 3,928,356, 3,880,834, 3,668,210;

cardiovascular agents, as disclosed in U.S. Pat. Nos. 4,966,967, 5,661,129, 5,552,411, 5,332,737, 5,389,675, 5,198,449, 5,079,247, 4,966,967, 4,874,760, 4,954,526, 5,051,423, 4,888,335, 4,853,391, 4,906,634, 4,775,757, 4,727,072, 4,542,160, 4,522,949, 4,524,151, 4,525,479, 4,474,804, 4,520,026, 4,520,026, 5,869,478, 5,859,239, 5,837,702, 5,807,889, 5,731,322, 5,726,171, 5,723,457, 5,705,523, 5,696,111, 5,691,332, 5,679,672, 5,661,129, 5,654,294, 5,646,276, 5,637,586, 5,631,251, 5,612,370, 5,612,323, 5,574,037, 5,563,170, 5,552,411, 5,552,397, 5,547,966, 5,482,925, 5,457,118, 5,414,017, 5,414,013, 5,401,758, 5,393,771, 5,362,902, 5,332,737, 5,310,731, 5,260,444, 5,223,516, 5,217,958, 5,208,245, 5,202,330, 5,198,449, 5,189,036, 5,185,362, 5,140,031, 5,128,349, 5,116,861, 5,079,247, 5,070,099, 5,061,813, 5,055,466, 5,051,423, 5,036,065, 5,026,712, 5,011,931, 5,006,542, 4,981,843, 4,977,144, 4,971,984, 4,966,967, 4,959,383, 4,954,526, 4,952,692, 4,939,137, 4,906,634, 4,889,866, 4,888,335, 4,883,872, 4,883,811, 4,847,379, 4,835,157, 4,824,831, 4,780,538, 4,775,757, 4,774,239, 4,771,047, 4,769,371, 4,767,756, 4,762,837, 4,753,946, 4,752,616, 4,749,715, 4,738,978, 4,735,962, 4,734,426, 4,734,425, 4,734,424, 4,730,052, 4,727,072, 4,721,796, 4,707,550, 4,704,382, 4,703,120, 4,681,970, 4,681,882, 4,670,560, 4,670,453, 4,668,787, 4,663,337, 4,663,336, 4,661,506, 4,656,267, 4,656,185, 4,654,357, 4,654,356, 4,654,355, 4,654,335, 4,652,578, 4,652,576, 4,650,874, 4,650,797, 4,649,139, 4,647,585, 4,647,573, 4,647,565, 4,647,561, 4,645,836, 4,639,461, 4,638,012, 4,638,011, 4,632,931, 4,631,283, 4,628,095, 4,626,548, 4,614,825, 4,611,007, 4,611,006, 4,611,005, 4,609,671, 4,608,386, 4,607,049, 4,607,048, 4,595,692, 4,593,042, 4,593,029, 4,591,603, 4,588,743, 4,588,742, 4,588,741, 4,582,854, 4,575,512, 4,568,762, 4,560,698, 4,556,739, 4,556,675, 4,555,571, 4,555,570, 4,555,523, 4,550,120, 4,542,160, 4,542,157, 4,542,156, 4,542,155, 4,542,151, 4,537,981, 4,537,904, 4,536,514, 4,536,513, 4,533,673, 4,526,901, 4,526,900, 4,525,479, 4,524,151, 4,522,949, 4,521,539, 4,520,026, 4,517,188, 4,482,562, 4,474,804, 4,474,803, 4,472,411, 4,466,979, 4,463,015, 4,456,617, 4,456,616, 4,456,615, 4,418,076, 4,416,896, 4,252,815, 4,220,594, 4,190,587, 4,177,280, 4,164,586, 4,151,297, 4,145,443, 4,143,054, 4,123,550, 4,083,968, 4,076,834, 4,064,259, 4,064,258, 4,064,257, 4,058,620, 4,001,421, 3,993,639, 3,991,057, 3,982,010, 3,980,652, 3,968,117, 3,959,296, 3,951,950, 3,933,834, 3,925,369, 3,923,818, 3,898,210, 3,897,442, 3,897,441, 3,886,157, 3,883,540, 3,873,715, 3,867,383, 3,873,715, 3,867,383, 3,691,216, 3,624,126;

antimicrobial agents as disclosed in U.S. Pat. Nos. 5,902,594, 5,874,476, 5,874,436, 5,859,027, 5,856,320, 5,854,242, 5,811,091, 5,786,350, 5,783,177, 5,773,469, 5,762,919, 5,753,715, 5,741,526, 5,709,870, 5,707,990, 5,696,117, 5,684,042, 5,683,709, 5,656,591, 5,643,971, 5,643,950, 5,610,196, 5,608,056, 5,604,262, 5,595,742, 5,576,341, 5,554,373, 5,541,233, 5,534,546, 5,534,508, 5,514,715, 5,508,417, 5,464,832, 5,428,073, 5,428,016, 5,424,396, 5,399,553, 5,391,544, 5,385,902, 5,359,066, 5,356,803, 5,354,862, 5,346,913, 5,302,592, 5,288,693, 5,266,567, 5,254,685, 5,252,745, 5,209,930, 5,196,441, 5,190,961, 5,175,160, 5,157,051, 5,096,700, 5,093,342, 5,089,251, 5,073,570, 5,061,702, 5,037,809, 5,036,077, 5,010,109, 4,970,226, 4,916,156, 4,888,434, 4,870,093, 4,855,318, 4,784,991, 4,746,504, 4,686,221, 4,599,228, 4,552,882, 4,492,700, 4,489,098, 4,489,085, 4,487,776, 4,479,953, 4,477,448, 4,474,807, 4,470,994, 4,370,484, 4,337,199, 4,311,709, 4,308,283, 4,304,910, 4,260,634, 4,233,311, 4,215,131, 4,166,122, 4,141,981, 4,130,664, 4,089,977, 4,089,900, 4,069,341, 4,055,655, 4,049,665, 4,044,139, 4,002,775, 3,991,201, 3,966,968, 3,954,868, 3,936,393, 3,917,476, 3,915,889, 3,867,548, 3,865,748, 3,867,548, 3,865,748, 3,783,160, 3,764,676, 3,764,677;

anti-inflammatory agents as disclosed in U.S. Pat. Nos. 5,872,109, 5,837,735, 5,827,837, 5,821,250, 5,814,648, 5,780,026, 5,776,946, 5,760,002, 5,750,543, 5,741,798, 5,739,279, 5,733,939, 5,723,481, 5,716,967, 5,688,949, 5,686,488, 5,686,471, 5,686,434, 5,684,204, 5,684,041, 5,684,031, 5,684,002, 5,677,318, 5,674,891, 5,672,626, 5,665,752, 5,656,661, 5,635,516, 5,631,283, 5,622,948, 5,618,835, 5,607,959, 5,593,980, 5,593,960, 5,580,888, 5,552,424, 5,552,422, 5,516,764, 5,510,361, 5,508,026, 5,500,417, 5,498,405, 5,494,927, 5,476,876, 5,472,973, 5,470,885, 5,470,842, 5,464,856, 5,464,849, 5,462,952, 5,459,151, 5,451,686, 5,444,043, 5,436,265, 5,432,181, RE034,918, 5,393,756, 5,380,738, 5,376,670, 5,360,811, 5,354,768, 5,348,957, 5,347,029, 5,340,815, 5,338,753, 5,324,648, 5,319,099, 5,318,971, 5,312,821, 5,302,597, 5,298,633, 5,298,522, 5,298,498, 5,290,800, 5,290,788, 5,284,949, 5,280,045, 5,270,319, 5,266,562, 5,256,680, 5,250,700, 5,250,552, 5,248,682, 5,244,917, 5,240,929, 5,234,939, 5,234,937, 5,232,939, 5,225,571, 5,225,418, 5,220,025, 5,212,189, 5,212,172, 5,208,250, 5,204,365, 5,202,350, 5,196,431, 5,191,084, 5,187,175, 5,185,326, 5,183,906, 5,177,079, 5,171,864, 5,169,963, 5,155,122, 5,143,929, 5,143,928, 5,143,927, 5,124,455, 5,124,347, 5,114,958, 5,112,846, 5,104,656, 5,098,613, 5,095,037, 5,095,019, 5,086,064, 5,081,261, 5,081,147, 5,081,126, 5,075,330, 5,066,668, 5,059,602, 5,043,457, 5,037,835, 5,037,811, 5,036,088, 5,013,850, 5,013,751, 5,013,736, 5,006,542, 4,992,448, 4,992,447, 4,988,733, 4,988,728, 4,981,865, 4,962,119, 4,959,378, 4,954,519, 4,945,099, 4,942,236, 4,931,457, 4,927,835, 4,912,248, 4,910,192, 4,904,786, 4,904,685, 4,904,674, 4,904,671, 4,897,397, 4,895,953, 4,891,370, 4,870,210, 4,859,686, 4,857,644, 4,853,392, 4,851,412, 4,847,303, 4,847,290, 4,845,242, 4,835,166, 4,826,990, 4,803,216, 4,801,598, 4,791,129, 4,788,205, 4,778,818, 4,775,679, 4,772,703, 4,767,776, 4,764,525, 4,760,051, 4,748,153, 4,725,616, 4,721,712, 4,713,393, 4,708,966, 4,695,571, 4,686,235, 4,686,224, 4,680,298, 4,678,802, 4,652,564, 4,644,005, 4,632,923, 4,629,793, 4,614,741, 4,599,360, 4,596,828, 4,595,694, 4,595,686, 4,594,357, 4,585,755, 4,579,866, 4,578,390, 4,569,942, 4,567,201, 4,563,476, 4,559,348, 4,558,067, 4,556,672, 4,556,669, 4,539,326, 4,537,903, 4,536,503, 4,518,608, 4,514,415, 4,512,990, 4,501,755, 4,495,197, 4,493,839, 4,465,687, 4,440,779, 4,440,763, 4,435,420, 4,412,995, 4,400,534, 4,355,034, 4,335,141, 4,322,420, 4,275,064, 4,244,963, 4,235,908, 4,234,593, 4,226,887, 4,201,778, 4,181,720, 4,173,650, 4,173,634, 4,145,444, 4,128,664, 4,125,612, 4,124,726, 4,124,707, 4,117,135, 4,027,031, 4,024,284, 4,021,553, 4,021,550, 4,018,923, 4,012,527, 4,011,326, 3,998,970, 3,998,954, 3,993,763, 3,991,212, 3,984,405, 3,978,227, 3,978,219, 3,978,202, 3,975,543, 3,968,224, 3,959,368, 3,949,082, 3,949,081, 3,947,475, 3,936,450, 3,934,018, 3,930,005, 3,857,955, 3,856,962, 3,821,377, 3,821,401, 3,789,121, 3,789,123, 3,726,978, 3,694,471, 3,691,214, 3,678,169, 3,624,216;

immunosuppressive agents, as disclosed in U.S. Pat. Nos. 4,450,159, 4,450,159, 5,905,085, 5,883,119, 5,880,280, 5,877,184, 5,874,594, 5,843,452, 5,817,672, 5,817,661, 5,817,660, 5,801,193, 5,776,974, 5,763,478, 5,739,169, 5,723,466, 5,719,176, 5,696,156, 5,695,753, 5,693,648, 5,693,645, 5,691,346, 5,686,469, 5,686,424, 5,679,705, 5,679,640, 5,670,504, 5,665,774, 5,665,772, 5,648,376, 5,639,455, 5,633,277, 5,624,930, 5,622,970, 5,605,903, 5,604,229, 5,574,041, 5,565,560, 5,550,233, 5,545,734, 5,540,931, 5,532,248, 5,527,820, 5,516,797, 5,514,688, 5,512,687, 5,506,233, 5,506,228, 5,494,895, 5,484,788, 5,470,857, 5,464,615, 5,432,183, 5,431,896, 5,385,918, 5,349,061, 5,344,925, 5,330,993, 5,308,837, 5,290,783, 5,290,772, 5,284,877, 5,284,840, 5,273,979, 5,262,533, 5,260,300, 5,252,732, 5,250,678, 5,247,076, 5,244,896, 5,238,689, 5,219,884, 5,208,241, 5,208,228, 5,202,332, 5,192,773, 5,189,042, 5,169,851, 5,162,334, 5,151,413, 5,149,701, 5,147,877, 5,143,918, 5,138,051, 5,093,338, 5,091,389, 5,068,323, 5,068,247, 5,064,835, 5,061,728, 5,055,290, 4,981,792, 4,810,692, 4,410,696, 4,346,096, 4,342,769, 4,317,825, 4,256,766, 4,180,588, 4,000,275, 3,759,921;

immunomodulatory agents, as disclosed in U.S. Pat. Nos. 4,446,128, 4,524,147, 4,720,484, 4,722,899, 4,748,018, 4,877,619, 4,998,931, 5,049,387, 5,118,509, 5,152,980, 5,256,416, 5,468,729, 5,583,139, 5,604,234, 5,612,060, 5,612,350, 5,658,564, 5,672,605, 5,681,571, 5,708,002, 5,723,718, 5,736,143, 5,744,495, 5,753,687, 5,770,201, 5,869,057, 5,891,653, 5,939,455, 5,948,407, 6,006,752, 6,024,957, 6,030,624, 6,037,372, 6,037,373, 6,043,247, 6,060,049, 6,087,096, 6,096,315, 6,099,838, 6,103,235, 6,124,495, 6,153,203, 6,169,087, 6,255,278, 6,262,044, 6,290,950, 6,306,651, 6,322,796, 6,329,153, 6,344,476, 6,352,698, 6,365,163, 6,379,668, 6,391,303, 6,395,767, 6,403,555, 6,410,556, 6,412,492, 6,468,537, 6,489,330, 6,521,232, 6,525,035, 6,525,242, 6,558,663, 6,572,860;

analgesic agents, as disclosed in U.S. Pat. Nos. 5,292,736, 5,688,825, 5,554,789, 5,455,230, 5,292,736, 5,298,522, 5,216,165, 5,438,064, 5,204,365, 5,017,578, 4,906,655, 4,906,655, 4,994,450, 4,749,792, 4,980,365, 4,794,110, 4,670,541, 4,737,493, 4,622,326, 4,536,512, 4,719,231, 4,533,671, 4,552,866, 4,539,312, 4,569,942, 4,681,879, 4,511,724, 4,556,672, 4,721,712, 4,474,806, 4,595,686, 4,440,779, 4,434,175, 4,608,374, 4,395,402, 4,400,534, 4,374,139, 4,361,583, 4,252,816, 4,251,530, 5,874,459, 5,688,825, 5,554,789, 5,455,230, 5,438,064, 5,298,522, 5,216,165, 5,204,365, 5,030,639, 5,017,578, 5,008,264, 4,994,450, 4,980,365, 4,906,655, 4,847,290, 4,844,907, 4,794,110, 4,791,129, 4,774,256, 4,749,792, 4,737,493, 4,721,712, 4,719,231, 4,681,879, 4,670,541, 4,667,039, 4,658,037, 4,634,708, 4,623,648, 4,622,326, 4,608,374, 4,595,686, 4,594,188, 4,569,942, 4,556,672, 4,552,866, 4,539,312, 4,536,512, 4,533,671, 4,511,724, 4,440,779, 4,434,175, 4,400,534, 4,395,402, 4,391,827, 4,374,139, 4,361,583, 4,322,420, 4,306,097, 4,252,816, 4,251,530, 4,244,955, 4,232,018, 4,209,520, 4,164,514, 4,147,872, 4,133,819, 4,124,713, 4,117,012, 4,064,272, 4,022,836, 3,966,944;

cholinergic agents, as disclosed in U.S. Pat. Nos. 5,219,872, 5,219,873, 5,073,560, 5,073,560, 5,346,911, 5,424,301, 5,073,560, 5,219,872, 4,900,748, 4,786,648, 4,798,841, 4,782,071, 4,710,508, 5,482,938, 5,464,842, 5,378,723, 5,346,911, 5,318,978, 5,219,873, 5,219,872, 5,084,281, 5,073,560, 5,002,955, 4,988,710, 4,900,748, 4,798,841, 4,786,648, 4,782,071, 4,745,123, 4,710,508;

adrenergic agents, as disclosed in U.S. Pat. Nos. 5,091,528, 5,091,528, 4,835,157, 5,708,015, 5,594,027, 5,580,892, 5,576,332, 5,510,376, 5,482,961, 5,334,601, 5,202,347, 5,135,926, 5,116,867, 5,091,528, 5,017,618, 4,835,157, 4,829,086, 4,579,867, 4,568,679, 4,469,690, 4,395,559, 4,381,309, 4,363,808, 4,343,800, 4,329,289, 4,314,943, 4,311,708, 4,304,721, 4,296,117, 4,285,873, 4,281,189, 4,278,608, 4,247,710, 4,145,550, 4,145,425, 4,139,535, 4,082,843, 4,011,321, 4,001,421, 3,982,010, 3,940,407, 3,852,468, 3,832,470;

antihistamine agents, as disclosed in U.S. Pat. Nos. 5,874,479, 5,863,938, 5,856,364, 5,770,612, 5,702,688, 5,674,912, 5,663,208, 5,658,957, 5,652,274, 5,648,380, 5,646,190, 5,641,814, 5,633,285, 5,614,561, 5,602,183, 4,923,892, 4,782,058, 4,393,210, 4,180,583, 3,965,257, 3,946,022, 3,931,197;

steroidal agents, as disclosed in U.S. Pat. Nos. 5,863,538, 5,855,907, 5,855,866, 5,780,592, 5,776,427, 5,651,987, 5,346,887, 5,256,408, 5,252,319, 5,209,926, 4,996,335, 4,927,807, 4,910,192, 4,710,495, 4,049,805, 4,004,005, 3,670,079, 3,608,076, 5,892,028, 5,888,995, 5,883,087, 5,880,115, 5,869,475, 5,866,558, 5,861,390, 5,861,388, 5,854,235, 5,837,698, 5,834,452, 5,830,886, 5,792,758, 5,792,757, 5,763,361, 5,744,462, 5,741,787, 5,741,786, 5,733,899, 5,731,345, 5,723,638, 5,721,226, 5,712,264, 5,712,263, 5,710,144, 5,707,984, 5,705,494, 5,700,793, 5,698,720, 5,698,545, 5,696,106, 5,677,293, 5,674,861, 5,661,141, 5,656,621, 5,646,136, 5,637,691, 5,616,574, 5,614,514, 5,604,215, 5,604,213, 5,599,807, 5,585,482, 5,565,588, 5,563,259, 5,563,131, 5,561,124, 5,556,845, 5,547,949, 5,536,714, 5,527,806, 5,506,354, 5,506,221, 5,494,907, 5,491,136, 5,478,956, 5,426,179, 5,422,262, 5,391,776, 5,382,661, 5,380,841, 5,380,840, 5,380,839, 5,373,095, 5,371,078, 5,352,809, 5,344,827, 5,344,826, 5,338,837, 5,336,686, 5,292,906, 5,292,878, 5,281,587, 5,272,140, 5,244,886, 5,236,912, 5,232,915, 5,219,879, 5,218,109, 5,215,972, 5,212,166, 5,206,415, 5,194,602, 5,166,201, 5,166,055, 5,126,488, 5,116,829, 5,108,996, 5,099,037, 5,096,892, 5,093,502, 5,086,047, 5,084,450, 5,082,835, 5,081,114, 5,053,404, 5,041,433, 5,041,432, 5,034,548, 5,032,586, 5,026,882, 4,996,335, 4,975,537, 4,970,205, 4,954,446, 4,950,428, 4,946,834, 4,937,237, 4,921,846, 4,920,099, 4,910,226, 4,900,725, 4,892,867, 4,888,336, 4,885,280, 4,882,322, 4,882,319, 4,882,315, 4,874,855, 4,868,167, 4,865,767, 4,861,875, 4,861,765, 4,861,763, 4,847,014, 4,774,236, 4,753,932, 4,711,856, 4,710,495, 4,701,450, 4,701,449, 4,689,410, 4,680,290, 4,670,551, 4,664,850, 4,659,516, 4,647,410, 4,634,695, 4,634,693, 4,588,530, 4,567,000, 4,560,557, 4,558,041, 4,552,871, 4,552,868, 4,541,956, 4,519,946, 4,515,787, 4,512,986, 4,502,989, 4,495,102;

the disclosures of all the above of which are herein incorporated by reference.

The drug moiety of the conjugate may be the whole drug or a binding fragment or portion thereof that retains its affinity and specificity for the target of interest while having a linkage site for covalent bonding to the vector protein ligand or linker. The conjugates of such drugs may be used for the same disorders, diseases, and indications as the drugs themselves.

C. Preferred Cancer Chemotherapeutic Active Agents

Preferred cancer chemotherapeutic agents for use in the RAP or RAP polypeptide conjugates of the invention include all drugs which may be useful for treating brain tumors or other neoplasia in or around the brain, either in the free form, or, if not so useful for such tumors in the free form, then useful when linked to RAP or a RAP polypeptide. Such chemotherapeutic agents include adriamycin (also known as doxorubicin), cisplatin, paclitaxel, analogs thereof, and other chemotherapeutic agents demonstrate activity against tumours ex vivo and in vivo. Such chemotherapeutic agents also include alkylating agents, antimetabolites, natural products (such as vinca alkaloids, epidophyllotoxins, antibiotics, enzymes and biological response modifiers), topoisomerase inhibitors, microtubule inhibitors, spindle poisons, hormones and antagonists, and miscellaneous agents such as platinum coordination complexes, anthracendiones, substituted ureas, etc. hose of skill in the art will know of other chemotherapeutic agents.

Preferred chemotherapeutic agents are those, which in the free form, demonstrate unacceptable systemic toxicity at desired doses. The general systemic toxicity associated with therapeutic levels of such agents is reduced by their linkage to RAP or a RAP polypeptide. Particularly preferred are cardiotoxic compounds that are useful therapeutics but are dose limited by cardiotoxicity. A classic example is adriamycin (also known as doxorubicin) and its analogs, such as daunorubicin. Linking RAP or a RAP polypeptide to such drugs accumulation and associated cardiotoxicity at the heart.

VI. Methods for Making RAP-active Agent Conjugates

The present invention generally provides methods and compositions comprising RAP or a RAP polypeptide linked to an active agent.

In general, RAP-active agent conjugates can be prepared using techniques known in the art. There are numerous approaches for the conjugation or chemical crosslinking of compounds to proteins and one skilled in the art can determine which method is appropriate for the active agent to be conjugated. The method employed must be capable of joining the active agent to RAP or the RAP polypeptide without interfering with the ability of the RAP/RAP polypeptide to bind to its receptor, preferably without altering the desired activity of the compound once delivered. Preferred methods of conjugating RAP to various compounds are set out in the example section, below. Particularly preferred for linking complex molecules to RAP is the SATA/sulfo-SMCC crosslinking reaction (Pierce (Rockford, Ill.)). For linking metals to RAP, preferred reactions include, but are not limited to, binding to tyrosine residues through Chloramine T methods, or use of Iodo beads (Pierce) for iodination reactions.

Methods for conjugating the RAP with the representative labels set forth above may be readily accomplished by one of ordinary skill in the art (see, Trichothecene Antibody Conjugate, U.S. Pat. No. 4,744,981; Antibody Conjugate, U.S. Pat. No. 5,106,951; Fluorogenic Materials and Labeling Techniques, U.S. Pat. No. 4,018,884; Metal Radionuclide Labeled Proteins for Diagnosis and Therapy, U.S. Pat. No. 4,897,255; and Metal Radionuclide Chelating Compounds for Improved Chelation Kinetics, U.S. Pat. No. 4,988,496; see also Inman, Methods In Enzymology, Vol. 34, Affinity Techniques, Enzyme Purification: Part B, Jakoby and Wichek (eds.), Academic Press, New York, p. 30, 1974; see also Wilchek and Bayer, "The Avidin-Biotin Complex in Bioanalytical Applications," Anal. Biochem. 171:1-32, 1988; all incorporated herein by reference in their entirety for all purposes).

If the active agent is a protein or a peptide, there are many crosslinkers available in order to conjugate the active agent with the RAP or a substance that binds RAP. (See for example, Chemistry of Protein Conjugation and Crosslinking. 1991, Shans Wong, CRC Press, Ann Arbor). The crosslinker is generally chosen based on the reactive functional groups available or inserted on the therapeutic compound. In addition, if there are no reactive groups a photoactivatible crosslinker can be used. In certain instances, it may be desirable to include a spacer between RAP and the active agent. In one example, RAP and protein therapeutic compounds can be conjugated by the introduction of a sulfhydryl group on the RAP and the introduction of a cross-linker containing a reactive thiol group on to the protein compound through carboxyl groups (see, Wawizynczak, E. J. and Thorpe, P. E. in Immunoconjugates: Antibody Conjugates in Radioimaging and Therapy of Cancer, C. W. Vogel (Ed.) Oxford University Press, 1987, pp. 28-55.; and Blair, A. H. and T. I. Ghose, *J. Immunol. Methods* 59:129, 1983).

RAP-chemotherapeutic agents can comprise one or more compound moieties linked to RAP. For example, conjugation reactions may conjugate from 1 to 10 or more molecules of adriamycin to a single RAP molecule. Several atoms of gold or iodine can be conjugated to a single RAP polypeptide. These formulations can be employed as mixtures, or they may be purified into specific RAP-compound stoichiometric formulations. Those skilled in the art are able to determine which format and which stoichiometric ratio is preferred. Further, mixtures of compounds may be linked to RAP, such as the RAP adriamycin-cisplatinum composition set out in the examples. These RAP-active agent conjugates may consist of a range of stoichiometric ratios of RAP to an active agent (e.g., RAP:active agent ratios of 1:1 to 1:4; 1:5 to 1:10; or 1:10 to 1:20). Optionally, a plurality of different active agents (e.g. 2, 3, or 4 such agents) may be each conjugated to the RAP or RAP polypeptide in its own stoichiometric ratio such that RAP to the total ratio of such additional active agents is not fewer than 1 RAP per 20 active agents. These, too, may be separated into purified mixtures or they may be employed in aggregate.

The linker is preferably an organic moiety constructed to contain an alkyl, aryl and/or amino acid backbone and which will contain an amide, ether, ester, hydrazone, disulphide linkage or any combination thereof. Linkages containing amino acid, ether and amide bound components will be stable under conditions of physiological pH, normally 7.4 in serum and 4-5 on uptake into cells (endosomes). Preferred linkages are linkages containing esters or hydrazones that are stable at serum pH but hydrolyse to release the drug when exposed to intracellular pH. Disulphide linkages are preferred because they are sensitive to reductive cleavage; amino acid linkers can be designed to be sensitive to cleavage by specific enzymes in the desired target organ. Exemplary linkers are set out in Blattler et al. *Biochem.* 24:1517-1524, 1985; King et al. *Biochem.* 25:5774-5779, 1986; Srinivasachar and Nevill, *Biochem.* 28:2501-2509, 1989.

Drug-Linker intermediates are similar to what has been described above but with either an active ester to react with free amine groups on the RAP or a maleimide to react with the free thiols that have been created on RAP through other groups where persons skilled in the art can attach them to RAP.

Methods of crosslinking proteins and peptides are well known to those of skill in the art. Several hundred crosslinkers are available for conjugating a compound of interest with RAP or with a substance which binds RAP (see, e.g., *Chemistry of Protein Conjugation and Crosslinking*, Shans Wong, CRC Press, Ann Arbor (1991) and U.S. Pat. No. 5,981,194 and PCT Patent Publication Nos. WO 02/13843 and WO 01/59459 which are incorporated herein by reference in their entirety). Many reagents and cross-linkers can be used to prepare conjugates of an active agent and a RAP moleculeee, for instance, Hermanson, et al. *Bioconjugate Techniques*, Academic Press, (1996). The crosslinker is generally chosen based on the reactive functional groups available or inserted on the therapeutic agent. In addition, if there are no reactive groups, a photoactivatible crosslinker can be used. In certain instances, it may be desirable to include a spacer between RAP and the agent. In one embodiment, RAP and the protein therapeutic agents may be conjugated by the introduction of a sulfhydryl group on RAP and by the introduction of a crosslinker containing a reactive thiol group on to the protein compound through carboxyl groups (Wawizynczak and Thorpe in *Immunoconjugates: Antibody Conjugates in Radioimaging and Therapy of Cancer*, Vogel (Ed.) Oxford University Press, pp. 28-55 (1987); and Blair and Ghose (1983) *J. Immunol. Methods* 59:129). In some embodiments, the linker is vulnerable to hydrolysis at the acidic pH of the lysosome so as to free the agent from the and/or linker.

When a linker is used, the linker is preferably an organic moiety constructed to contain an alkyl, aryl and/or amino acid backbone, and containing an amide, ether, ester, hydrazone, disulphide linkage or any combination thereof. Linkages containing amino acid, ether and amide bound components are stable under conditions of physiological pH, normally 7.4 in serum. Preferred linkages are those containing esters or hydrazones that are stable at serum pH, but that hydrolyze to release the drug when exposed to lysosomal pH. Disulphide linkages are preferred because they are sensitive to reductive cleavage. In addition, amino acid linkers may be designed to be sensitive to cleavage by specific enzymes in the desired target organ or more preferably, the lysosome itself. Exemplary linkers are described in Blattler et al. (1985) *Biochem.* 24:1517-1524; King et al. (1986) *Biochem.* 25:5774-5779; Srinivasachar and Nevill (1989) *Biochem.* 28:2501-2509.

In some embodiments, the linker is a polyethylene glycol or polypropylene glycol. In other embodiments, the linker is from 4 to 20 atoms long. In other embodiments, the linker is from 1 to 30 atoms long with carbon chain atoms that may be substituted by heteroatoms independently selected from the group consisting of O, N, or S. In some embodiments, from 1 to 4 or up to one-third of the C atoms are substituted with a heteroatom independently selected from O, N, S. In other embodiments, the linker contains a moiety subject to hydrolysis upon delivery to the lysosomal environment (e.g., susceptible to hydrolysis at the lysosomal pH or upon contact to a lysosomal enzyme). In some embodiments, the linker group is preferably hydrophilic to enhance the solubility of the conjugate in body fluids. In some embodiments, the linker contains or is attached to the RAP molecule or the protein agent by a functional group subject to attack by other lysosomal enzymes (e.g., enzymes not deficient in the target lysosome or a lysosomal enzyme not conjugated to the RAP carrier). In some embodiments, the RAP and agent are joined by a linker comprising amino acids or peptides, lipids, or sugar residues. In some embodiments, the RAP and agent are joined at groups introduced synthetically or by post-translational modifications.

In some embodiments, agent-linker intermediates are similar to what has been described previously, but comprise, for example, either an active ester that can react with free amine groups on RAP or a maleimide that can react with the free thiols created on RAP via a SATA reaction or through other groups where persons skilled in the art can attach them to.

A. Methods for Conjugating a RAP Polypeptide to a Protein or Enzyme.

One of ordinary skill in the art would know how to conjugate an active agent to a protein or peptide. Methods of conjugating active agents and labels to proteins are well known in the art. See, for instance, U.S. Pat. No. 5,981,194. Many reagents and cross linkers can be used to prepare bioconjugates of an active agent and a biopolymer. See, for instance, Hermanson, et al. Bioconjugate Techniques, Academic Press, (1996).

Production of Chimeric Proteins

In some embodiments of the present invention, the RAP polypeptide active-agent conjugate is a RAP polypeptide-fusion protein. Fusion proteins may be prepared using standard techniques known in the art. Typically, a DNA molecule encoding RAP or a portion thereof is linked to a DNA molecule encoding the protein compound. The chimeric DNA construct, along with suitable regulatory elements can be cloned into an expression vector and expressed in a suitable host. The resultant fusion proteins contain RAP or a portion thereof used to the selected protein compound. RAP-LSD enzyme proteins, RAP-human alpha glucosidase and RAP-iduronidase, are described in Example VII and FIGS. 3 and 4 and were prepared using standard techniques known in the art.

The chimeric protein of the present invention can be produced using host cells expressing a single nucleic acid encoding the entire chimeric protein or more than one nucleic acid sequence, each encoding a domain of the chimeric protein and, optionally, an amino acid or amino acids which will serve to link the domains. The chimeric proteins can also be produced by chemical synthesis.

Host Cells

Host cells used to produce chimeric proteins are bacterial, yeast, insect, non-mammalian vertebrate, or mammalian cells; the mammalian cells include, but are not limited to, hamster, monkey, chimpanzee, dog, cat, bovine, porcine, mouse, rat, rabbit, sheep and human cells. The host cells can be immortalized cells (a cell line) or non-immortalized (primary or secondary) cells and can be any of a wide variety of cell types, such as, but not limited to, fibroblasts, keratinocytes, epithelial cells (e.g., mammary epithelial cells, intestinal epithelial cells), ovary cells (e.g., Chinese hamster ovary or CHO cells), endothelial cells, glial cells, neural cells, formed elements of the blood (e.g., lymphocytes, bone marrow cells), muscle cells, hepatocytes and precursors of these somatic cell types. Host cells can include mutants of CHO cells that do not express LRP such as CHO13-5-1 (FitzGerald, et al. *J. Cell Biol.* 129(6):1533-41 (1995)).

Cells that contain and express DNA or RNA encoding the chimeric protein are referred to herein as genetically modified cells. Mammalian cells that contain and express DNA or RNA encoding the chimeric protein are referred to as genetically modified mammalian cells. Introduction of the DNA or RNA into cells is by a known transfection method, such as electroporation, microinjection, microprojectile bombardment, calcium phosphate precipitation, modified calcium phosphate precipitation, cationic lipid treatment, photoporation, fusion methodologies, receptor mediated transfer, or polybrene precipitation. Alternatively, the DNA or RNA can be introduced by infection with a viral vector. Methods of producing cells, including mammalian cells, which express DNA or RNA encoding a chimeric protein are described in co-pending patent applications U.S. Ser. No. 08/334,797, entitled "In Vivo Protein Production and Delivery System for Gene Therapy", by Richard F Selden, Douglas A. Treco and Michael W. Heartlein (filed Nov. 4, 1994); U.S. Ser. No. 08/334,455, entitled "In Vivo Production and Delivery of Erythropoietin or Insulinotropin for Gene Therapy", by Richard F Selden, Douglas A. Treco and Michael W. Heartlein (filed Nov. 4, 1994) and U.S. Ser. No. 08/231,439, entitled "Targeted Introduction of DNA Into Primary or Secondary Cells and Their Use for Gene Therapy", by Douglas A. Treco, Michael W. Heartlein and Richard F Selden (filed Apr. 20, 1994). The teachings of each of these applications are expressly incorporated herein by reference in their entirety.

Nucleic Acid Constructs

A nucleic acid construct used to express the chimeric protein can be one which is expressed extrachromosomally (episomally) in the transfected mammalian cell or one which integrates, either randomly or at a pre-selected targeted site through homologous recombination, into the recipient cell's genome. A construct which is expressed extrachromosomally comprises, in addition to chimeric protein-encoding sequences, sequences sufficient for expression of the protein in the cells and, optionally, for replication of the construct. It typically includes a promoter, chimeric protein-encoding DNA and a polyadenylation site. The DNA encoding the chimeric protein is positioned in the construct in such a manner that its expression is under the control of the promoter. Optionally, the construct may contain additional components such as one or more of the following: a splice site, an enhancer sequence, a selectable marker gene under the control of an appropriate promoter, and an amplifiable marker gene under the control of an appropriate promoter.

In those embodiments in which the DNA construct integrates into the cell's genome, it need include only the chimeric protein-encoding nucleic acid sequences. Optionally, it can include a promoter and an enhancer sequence, a polyadenylation site or sites, a splice site or sites, nucleic acid sequences which encode a selectable marker or markers, nucleic acid sequences which encode an amplifiable marker and/or DNA homologous to genomic DNA in the recipient cell to target integration of the DNA to a selected site in the genome (targeting DNA or DNA sequences).

Cell Culture Methods

Mammalian cells containing the chimeric protein-encoding DNA or RNA are cultured under conditions appropriate for growth of the cells and expression of the DNA or RNA. Those cells which express the chimeric protein can be identified, using known methods and methods described herein, and the chimeric protein isolated and purified, using known methods and methods also described herein; either with or without amplification of chimeric protein production. Identification can be carried out, for example, through screening genetically modified mammalian cells displaying a phenotype indicative of the presence of DNA or RNA encoding the chimeric protein, such as PCR screening, screening by Southern blot analysis, or screening for the expression of the chimeric protein. Selection of cells having incorporated chimeric protein-encoding DNA may be accomplished by including a selectable marker in the DNA construct and culturing transfected or infected cells containing a selectable marker gene under conditions appropriate for survival of only those cells that express the selectable marker gene. Further amplification of the introduced DNA construct can be affected by culturing genetically modified mammalian cells under conditions appropriate for amplification (e.g., culturing genetically modified mammalian cells containing an amplifiable marker gene in the presence of a concentration of a drug at which only cells containing multiple copies of the amplifiable marker gene can survive).

Genetically modified mammalian cells expressing the chimeric protein can be identified, as described herein, by detection of the expression product. For example, mammalian cells expressing chimeric protein in which the carrier is RAP can be identified by a sandwich enzyme immunoassay. The antibodies can be directed toward the LRP portion or the active agent portion.

VII. Labels

In some embodiments, the RAP polypeptide active agent conjugate is labeled to facilitate its detection. A "label" or a "detectable moiety" is a composition detectable by spectroscopic, photochemical, biochemical, immunochemical, chemical, or other physical means. For example, labels suitable for use in the present invention include, radioactive labels (e.g., $^{32}P$), fluorophores (e.g., fluorescein), electron-dense reagents, enzymes (e.g., as commonly used in an ELISA), biotin, digoxigenin, or haptens and proteins which can be made detectable, e.g., by incorporating a radiolabel into the hapten or peptide, or used to detect antibodies specifically reactive with the hapten or peptide.

As noted above, depending on the screening assay employed, the active agent, the linker or the RAP polypeptide portion of a conjugate may be labeled. The particular label or detectable group used is not a critical aspect of the invention, as long as it does not significantly interfere with the biological activity of the conjugate. The detectable group can be any material having a detectable physical or chemical property. Thus, a label is any composition detectable by spectroscopic, photochemical, biochemical, immunochemical, electrical, optical or chemical means.

Examples of labels suitable for use in the present invention include, but are not limited to, fluorescent dyes (e.g., fluorescein isothiocyanate, Texas red, rhodamine, and the like), radiolabels (e.g., $^3H$, $^{125}I$, $^{35}S$, $^{14}C$, or $^{32}P$), enzymes (e.g., horse radish peroxidase, alkaline phosphatase and others commonly used in an ELISA), and colorimetric labels such as colloidal gold or colored glass or plastic beads (e.g., polystyrene, polypropylene, latex, etc.).

The label may be coupled directly or indirectly to the desired component of the assay according to methods well known in the art. Preferably, the label in one embodiment is covalently bound to the biopolymer using an isocyanate reagent for conjugating an active agent according to the invention. In one aspect of the invention, the bifunctional isocyanate reagents of the invention can be used to conjugate a label to a biopolymer to form a label biopolymer conjugate without an active agent attached thereto. The label biopolymer conjugate may be used as an intermediate for the synthesis of a labeled conjugate according to the invention or may be used to detect the biopolymer conjugate. As indicated above, a wide variety of labels can be used, with the choice of label depending on sensitivity required, ease of conjugation with the desired component of the assay, stability requirements, available instrumentation, and disposal provisions. Non-radioactive labels are often attached by indirect means. Generally, a ligand molecule (e.g., biotin) is covalently bound to the molecule. The ligand then binds to another molecules (e.g., streptavidin) molecule, which is either inherently detectable or covalently bound to a signal system, such as a detectable enzyme, a fluorescent compound, or a chemiluminescent compound.

The conjugates can also be conjugated directly to signal generating compounds, e.g., by conjugation with an enzyme or fluorophore. Enzymes suitable for use as labels include, but are not limited to, hydrolases, particularly phosphatases, esterases and glycosidases, or oxidotases, particularly peroxidases. Fluorescent compounds, ie., fluorophores, suitable for use as labels include, but are not limited to, fluorescein and its derivatives, rhodamine and its derivatives, dansyl, umbelliferone, etc. Further examples of suitable fluorophores include, but are not limited to, eosin, TRITC-amine, quinine, fluorescein W, acridine yellow, lissamine rhodamine, B sulfonyl chloride erythroscein, ruthenium (tris, bipyridinium), Texas Red, nicotinamide adenine dinucleotide, flavin adenine dinucleotide, etc. Chemiluminescent compounds suitable for use as labels include, but are not limited to, luciferin and 2,3-dihydrophthalazinediones, e.g., luminol. For a review of various labeling or signal producing systems that can be used in the methods of the present invention, see U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by the use of electronic detectors such as charge coupled devices (CCDs) or photomultipliers and the like. Similarly, enzymatic labels may be detected by providing the appropriate substrates for the enzyme and detecting the resulting reaction product. Colorimetric or chemiluminescent labels may be detected simply by observing the color associated with the label. Other labeling and detection systems suitable for use in the methods of the present invention will be readily apparent to those of skill in the art. Such labeled modulators and ligands may be used in the diagnosis of a disease or health condition.

VIII. Screening Assays for RAP Polypeptide Active Agent Conjugates and Modulators of Their Delivery via the LRP.

The present invention provides a screening assay for RAP polypeptide active agents conjugates, wherein the conjugates are tested for their ability to influence a measurable activity of the LRP receptor which can be situated in a whole cell, a cell extract, semi-purified, purified or any other format that allows for measurement of its activity. The activity can be any activity in the expression, function or degradation of LRP including, for example, the amount or timing of such activities. Such activities include, for example, transcription, transcript processing, translation or transcript stability of the LRP gene sequence or mRNA transcript. Such activities include, for example, the synthesis of new LRP, the sub-cellular localization of LRP and activation of LRP biological activity. Such activities include, for example, the ability of LRP to bind substances, adopt conformations, catalyze reactions, bind known ligands and the like. Such activities include, for example, the amount or stability of LRPl, the processing and removal or degradation of LRP and the like. In preferred embodiments, the LRP receptor for use in screening is LRP1.

The invention contemplates a variety of different screening formats. Some designs are considered low throughput and test only one or a few compounds in series or in parallel. High throughput screening assays are suitable for screening tens of thousands or hundreds of thousands of compounds in a matter of weeks or months. "In silico" screening formats employ computer-aided rational design techniques to identify potential modulators of LRP biological activity.

A. Modulating Uptake of RAP Conjugated Active Agents by Modulating LRP Activity

Those skilled in the art will appreciate that increasing RAP polypeptide active agent conjugate uptake and delivery to targets including, but not limited to, the brain or lysosomes is useful and desirable in situations such as, but not limited to, where the conjugate is being used to treat a neurological condition and/or a LSD arid increased amounts of delivery would provide therapeutic benefit. Those skilled in the art will appreciate that decreasing conjugate uptake and delivery across the blood-brain barrier is useful and desirable for a variety of reasons including, but not limited to, where the conjugate is being used for its potential cardio-protective effect or used in other (non-CNS) organs and side-effects of brain uptake are to be avoided.

Suitable RAP and RAP polypeptdes, active agent conjugates of RAP and RAP polypeptides, and modulators of LRP activity and modulators of RAP and RAP polypeptide conjugate delivery can also be readily identified using a modification of the Transwell apparatus set out in Example I below. In the modified form, a compound (e.g., RAP polypeptide, RAP polypeptide active agent conjugate, or modulator) is added to the luminal surface of the cells in the Transwell apparatus. The compound is then scored according to how well across the BBCECs to the abluminal side or as to how well (if a modulator) it increases or decreases the transport of a RAP conjugate or RAP polypeptide or another LRP ligand across the BBCECs to the abluminal side. A library of compounds can be readily screened or tested to identify pharmacologically superior modulators.

Other known ligands of the LRP receptor may be screened for use as modulators of the delivery of the conjugate, or as models for designing such modulators. These ligands include, but are not limited to, ApoE, Chylomicron remnants, $\beta$-VLDL, activated $\alpha$2-macroglobulin, tPA, Tissue factor inhibitor, Pro-uPA, PAI-1, Saposin, Gentamycin, Thyroglobulin, Polymixin B, Seminal Vesicle Secretory Protein A, Thrombospondin-1, Lactoferrin, and $\beta$-APP.

IX Methods of Using, Pharmaceutical Compositions, and Their Administration

The conjugates and modulators may be administered by a variety of routes. For oral preparations, the conjugates can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The conjugates,and modulators can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The conjugates, modulators, and LRP ligands can be utilized in aerosol formulation to be administered via inhalation. The compounds of the present invention can be formulated into pressurized acceptable propellants such as dichlorodifluoromethane, propane, nitrogen and the like.

Furthermore, the conjugates and modulators can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms of the conjugate, modulator, and LRP ligand for oral or rectal administration such as syrups, elixirs, and suspensions may be provided wherein each dosage unit, for example, teaspoonful, tablespoonful, tablet or suppository, contains a predetermined amount of the composition containing active agent. Similarly, unit dosage forms for injection or intravenous administration may comprise the conjugate in a composition as a solution in sterile water, normal saline or another pharmaceutically acceptable carrier.

In practical use, the conjugate, modulator, and LRP ligand according to the invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

With respect to transdermal routes of administration, methods for transdermal administration of drugs are disclosed in Remington's Pharmaceutical Sciences, 17th Edition, (Gennaro et al. Eds. Mack Publishing Co., 1985). Dermal or skin patches are a preferred means for transdermal delivery of the conjugates, modulators, and LRP ligands of the invention. Patches preferably provide an absorption enhancer such as DMSO to increase the absorption of the compounds. Other methods for transdermal drug delivery are disclosed in U.S. Pat. Nos. 5,962,012, 6,261,595, and 6,261,595. Each of which is incorporated by reference in its entirety.

Pharmaceutically acceptable excipients, such as vehicles, adjuvants, carriers or diluents, are commercially available. Moreover, pharmaceutically acceptable auxiliary substances, such as pH adjusting and buffering agents, tonicity adjusting agents, stabilizers, wetting agents and the like, are commercially available.

Those of skill will readily appreciate that dose levels can vary as a function of the specific compound, the severity of the symptoms and the susceptibility of the subject to side effects. Preferred dosages for a given compound are readily determinable by those of skill in the art by a variety of means, including, but not limited to dose response and pharmacokinetic assessments conducted in patients, test animals, and in vitro.

In each of these aspects, the compositions include, but are not limited to, compositions suitable for oral, rectal, topical, parenteral (including subcutaneous, intramuscular, and intravenous), pulmonary (nasal or buccal inhalation), or nasal administration, although the most suitable route in any given case will depend in part on the nature and severity of the conditions being treated and on the nature of the active ingredient. Exemplary routes of administration are the oral and intravenous routes. The compositions may be conveniently presented in unit dosage form and prepared by any of the methods well-known in the art of pharmacy.

In practical use, the modulators or according to the invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. The percentage of an active compound in these compositions may, of course, be varied and may conveniently be between about 2 percent to about 60 percent of the weight of the unit. The conjugates, modulators, and ligands of the invention are useful for therapeutic, prophylactic and diagnostic intervention in animals, and in particular in humans. As described herein, the conjugates show preferential accumulation and/or release of the active agent in any target organ, compartment, or site depending upon the biopolymer used.

Compositions of the present invention may be administered encapsulated in or attached to viral envelopes or vesicles, or incorporated into cells. Vesicles are micellular particles which are usually spherical and which are frequently lipidic. Liposomes are vesicles formed from a bilayer membrane. Suitable vesicles include, but are not limited to, unilamellar vesicles and multilamellar lipid vesicles or liposomes. Such vesicles and liposomes may be made from a wide range of lipid or phospholipid compounds, such as phosphatidylcholine, phosphatidic acid, phosphatidylserine, phosphatidylethanolamine, sphingomyelin, glycolipids, gangliosides, etc. using standard techniques, such as those described in, e.g., U.S. Pat. No. 4,394,448. Such vesicles or liposomes may be used to administer compounds intracellularly and to deliver compounds to the target organs. Controlled release of a p97-composition of interest may also be achieved using encapsulation (see, e.g., U.S. Pat. No. 5,186,941).

Any route of administration that dilutes the RAP polypeptide active agent conjugate or modulator composition into the blood stream, or preferably at least outside of the blood-brain barrier, may be used. Preferably, the composition is administered peripherally, most preferably intravenously or by cardiac catheter. Intrajugular and intracarotid injections are also useful. Compositions may be administered locally or regionally, such as intraperitoneally or subcutaneously on intramuscularly. In one aspect, compositions are administered with a suitable pharmaceutical diluent or carrier.

Dosages to be administered will depend on individual needs, on the desired effect, the active agent used, the biopolymer and on the chosen route of administration. Preferred dosages of a conjugate range from about 0.2 pmol/kg to about 25 nmol/kg, and particularly preferred dosages range from 2-250 pmol/kg; alternatively, preferred doses of the conjugate may be in the range of 0.02 to 2000 mg/kg. These dosages will be influenced by the number of active agent or drug moieties associated with the biopolymer. Alternatively, dosages may be calculated based on the active agent administered.

In preferred embodiments the conjugate comprises human RAP. For instance, doses of RAP-adriamycin comprising from 0.005 to 100 mg/kg of adriamycin are also useful in vivo. Particularly preferred is a dosage of RAP-adriamycin comprising from 0.05 mg/kg to 20 mg/kg of adriamycin. Those skilled in the art can determine suitable doses for compounds linked to RAP based in part on the recommended dosage used for the free form of the compound. RAP conjugation generally reduces the amount of drug needed to obtain the same effect.

The RAP polypeptide conjugates and modulators of the invention are useful for therapeutic, prophylactic and diagnostic intervention in animals, and in particular in humans. RAP compounds may show preferential accumulation in particular tissues. Preferred medical indications for diagnostic uses include, for example, any condition associated with a target organ of interest (e.g., lung, liver, kidney, spleen)

The subject methods find use in the treatment of a variety of different disease conditions. In certain embodiments, of particular interest is the use of the subject methods in disease conditions where an active agent or drug having desired activity has been previously identified, but in which the active agent or drug is not adequately delivered to the target site, area or compartment to produce a fully satisfactory therapeutic result. With such active agents or drugs, the subject methods of conjugating the active agent to RAP or a RAP polypeptide can be used to enhance the therapeutic efficacy and therapeutic index of active agent or drug.

The specific disease conditions treatable by with the subject conjugates are as varied as the types of drug moieties that can be present in the conjugate. Thus, disease conditions include cellular proliferative diseases, such as neoplastic diseases, autoimmune diseases, cardiovascular diseases, hormonal abnormality diseases, degenerative diseases, diseases of aging, diseases of the central nervous system (e.g., Alzheimer's disease, epilepsy, hyperlipidemias), psychiatric diseases and conditions (e.g., schizophrenia, mood disorders such as depression and anxiety), infectious diseases, enzyme deficiency diseases, lysosomal storage diseases such as those described above, and the like.

Treatment is meant to encompass any beneficial outcome to a subject associated with administration of a conjugate including a reduced likelihood of acquiring a disease, prevention of a disease, slowing, stopping or reversing, the progression of a disease or an amelioration of the symptoms associated with the disease condition afflicting the host, where amelioration or benefit is used in a broad sense to refer to at least a reduction in the magnitude of a parameter, e.g., symptom, associated with the pathological condition being treated, such as inflammation and pain associated therewith. As such, treatment also includes situations where the pathological condition, or at least symptoms associated therewith, are completely inhibited, e.g., prevented from happening, or stopped, e.g., terminated, such that the host no longer suffers from the pathological condition, or at least the symptoms that characterize the pathological condition.

A variety of hosts or subjects are treatable according to the subject methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the hosts will be humans.

X. Preparation of RAP and RAP Polypeptides.

RAP and RAP polypeptides for use according to the invention include those disclosed in U.S. Pat. No. 5,474,766 that is enclosed herein by reference in its entirety for the purposes of disclosing such peptides and how they may be obtained for use in the compounds and compositions of the present invention.

XI. Production of RAP Polypeptides

RAP, and RAP polypeptides, may be produced using any of the methods and techniques known to those skilled in the art. RAP can be purified from a naturally occurring source of the protein, can be isolated from a recombinant host expressing RAP or a RAP polypeptide, or can be synthesized using well known techniques in protein synthesis. A skilled artisan can readily adapt a variety of such techniques in order to obtain RAP or RAP polypeptides thatcontain the LRP binding site found on RAP. See, for instance, Melman et al., *J. Biol. Chem.* 276 (31): 29338-29346 (2001); Savonen, et al., *J Biol Chem.* 274(36); 25877-25882 (1999); Nielsen, et al. *Proc. Natl. Acad. Sci. USA* 94:7521-7525 (1997); Medved, et al., *J. Biol. Chem.* 274(2): 717-727 (1999); Rall, et al., *J. Biol. Chem.* 273(37): 24152-24157 (1998); Orlando, et al., *Proc. Natl. Acad. Sci. USA* 3161-3163 (1994).

The isolation of native RAP proteins has been described in Ashcom, et al., *J. Cell. Biol.* 110:1041-1048 (1990) and Jensen et al., *FEBS Lett.* 255:275-280 (1989). RAP fragments containing the LRP binding site may be generated from isolated native protein which is converted by enzymatic and/or chemical cleavage to generate fragments of the whole protein. Such methods are taught in U.S. Pat. No. 6,447,775 which is herein incorporated by reference with particular reference to such methods for obtaining RAP polypeptides.

In addition, RAP or a fragment of RAP can be expressed in a recombinant bacteria, as described, by Williams et al., *J. Biol. Chem.* 267:9035-9040 (1992) and Wurshawsky et al., *J. Biol. Chem.* 269:3325-3330 (1994).

Procedures for purifying the 39 kDa RAP protein from a recombinant *E.coli* strain has been previously described by Herz, et al., *J. Biol. Chem.* 266, 21232-21238 (1991). A modified version of that procedure can be used as described in U.S. Pat. No. 5,474,766 and below.

Cultures of *E. coli* strain DH5alpha carrying the expression plasmid pGEX-39 kDa can be grown to mid-log phase in LB medium with 100 μg/ml ampicillin at 37° C. Cultures can then be cooled to 30° C. and supplemented with 0.01% isopropylthio-beta-D-galactoside to induce expression of the glutathione-S-transferase-39 kDa fusion protein. Following a 4-6 hour induction at 30° C., cultures can be cooled with ice and recovered by centrifugation. All of the following steps are to be carried out at 4° C. Cell pellets are lysed in PBS with 1% Triton X-100, 1 μM pepstatin, 2.5 mu.g/ml leupeptin, 0.2 mM phenylmethylsulfonyl fluoride (PMSF), and 1 μM ethylenediaminetetraacetate (EDTA). Sonication of this lysate with a Branson Model 450 Sonifier with separation of the resulting membranes and other cellular debris by centrifugation at 15,000 g for 15 minutes is then followed by retrieval of the supernatant. The supernatant from this step is incubated overnight with agarose immobilized glutathione beads (Sigma Chemical Co.) in PBS and 0.1% sodium azide. The beads can then be washed, and elution of the fusion protein can be carried out by competition with 5 mM reduced glutathione (Sigma Chemical Co.). Following dialysis, the fusion protein can be cleaved by an overnight incubation with 100 ng of activated human thrombin per 50 μg of fusion protein. The glutathione-S-transferase epitope can subsequently be removed by further incubation with agarose immobilized glutathione beads.

The 28 kDa protein fragment of the 39 kDa protein ("28 kDa protein") of the present invention has the following amino acid sequence set forth in the Sequence Listing as SEQ ID NO:2 (FIG. 16).

The 28 kDa protein has a molecular weight of 28,000 daltons on SDS-PAGE, is relatively stabile to acid hydrolysis, is soluble in 1% Triton X-100, and has approximately the same inhibitory activity ($K_i$) on t-PA binding to the hepatic receptor as the 39 kDa protein. The 28 kDa protein may be cloned and purified as further exemplified in U.S. Pat. No. 5,474,766 which is expressly incorporated herein by reference for such methods of cloning.

The following examples further illustrate the present invention. These examples are intended merely to be illustrative of the present invention and are not to be construed as being limiting. The following examples provide exemplary protocols for assessing transcytosis in vitro and for characterizing the interaction of RAP and LRP receptor modulators or ligands with the RAP receptor or the blood-brain barrier.

EXAMPLES

Example I

Transcytosis of p97

Transport assays in BBCEC monolayers

A. Transcytosis

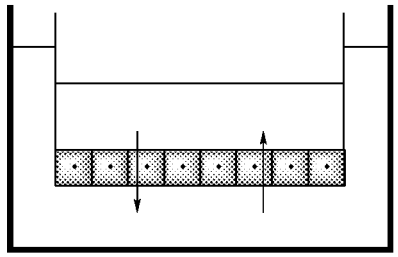

B. Uptake

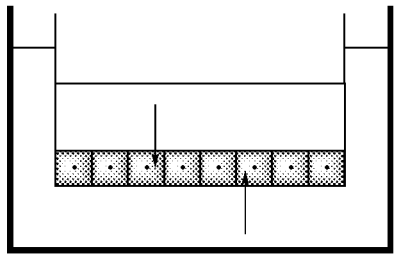

Transcytosis experiments were performed as follows. One insert covered with bovine brain capillary endothelial cells (BBCECs) was set into a Transwell apparatus containing a six-well microplate with 2 ml of Ringer/Hepes and pre-incubated for 2 h at 37° C. [$^{125}$I]-p97 (250 nM) was added to the upper side of the filter covered with cells. At various times, the insert was transferred to avoid re-endocytosis of p97 by the abluminal side of the BBCECs. At the end of experiment, [$^{125}$I]-p97 was measured after TCA precipitation.

The effect of RAP on transcytosis of $^{125}$I-p97 was assessed. In FIG. 1, RAP, a known polypeptide inhibitor of the LRP family was applied to the cells (25 micrograms/ml). RAP significantly inhibited the transcytosis of p97, thus directly implicating the LRP family in transcytosis.

Example II

Construction, Expression, Purification and Characterization of RAP Fusions

Expression constructs encoding fusions between the human receptor-associated protein (RAP) and human alpha-glucosidase (GAA), alpha-L-iduronidase (IDU) or glial cell-derived neurotrophic factor (GDNF) were prepared. For this purpose, a sequence that encodes RAP was fused to the 5'-end of sequences that encode the different fusion partners. All sequences were obtained by high-fidelity PCR amplification of human cDNA with the following primers shown in FIG. 2a. The GDNF fusion was designed for expression in bacteria. To this end, primer RAPBACF was substituted for RAPF in the RAP amplification or this construct (FIG. 2b).

The 5'-end of RAP was truncated to remove the signal peptide sequence. Instead, an in-frame BamHI site, which encodes the dipeptide GS, was added for the mammalian expression construct. Sequence encoding the tetrapeptide MGGS with an NcoI site at the 5'-end was added for the bacterial expression construct. The 3'-end of RAP was truncated to remove the tetrapeptide HNEL endoplasmic reticulum retention signal. Instead, the coding sequence for a six amino-acid spacer (AEAETG) was appended. The last two codons of the spacer specify an AgeI restriction site. The 5'-end of GAA was truncated to remove the signal peptide and pro-peptide sequences (Wisselaar, et al. *J. Biol. Chem.* 268 (3):2223-31 (1993)). Instead, an AgeI site was added to permit fusion to the RAP-spacer portion of the fusion. The 5'-end of IDU was similarly truncated to remove the signal peptide and introduce the restriction site. The 5'-end of GDNF was truncated to remove both the signal peptide and pro-peptide sequences (Lin, et al., *Science* 260(5111):1130-2 (1993)).

The open-reading frames encoding the GAA and IDU fusions were ligated into the expression vector pCINmt using flanking BamHI and XhoI sites. The vector contains the human melanotransferrin signal peptide with an in-frame BamHI site at the 3'-end. The sequences of the resulting fusion proteins are shown in FIGS. 3 and 4. The pCINmt (derived from Invitrogen vector pcDNA3.1) control sequences consist of the human CMV promoter followed by the rabbit IVS2 and the rat preproinsulin RNA leader sequence. A bovine growth hormone terminator sequence is positioned at the 3'-end of the expression cassette. The vector includes a selectable marker composed of an attenuated neomycin phosphotransferase gene driven by the weak HSV-tk promoter (Yenofsky, et al., *Proc. Natl. Acad. Sci. U.S.A.* 87(9):3435-9 (1990)). Expression constructs for RAP-GAA and RAP-IDU were transfected into an Lrp-deficient CHO cell line (CHO13-5-1) and recombinants selected with 800 µg/mL G418.

The RAPGDNF fusion (FIG. 5) was cloned into the bacterial expression vector pBADhisA (Invitrogen) using the flanking NcoI and XbaI sites. The resulting expression vector was transfected into BL21 cells and recombinants selected with carbenicillin. Expressed, purified RAP-GDNF fusion may be assayed for the ability to protect dopaminergic neurons or other activities as previously described (Kilic, et al., *Stroke* 34(5):1304-10 (2003)).

Expression of RAP Fusions:

Culture medium was JRH 302 supplemented with 2 mM L-glutamine, gentamycin, amphotericin, 800 µg/mL G418 and 2.5% fetal calf serum. Recombinant clones were grown in T225 flasks prior to seeding into 1 L Corning spinner flasks on Cytopore 1 beads (Amersham) in the presence of serum. Spinner flasks were maintained in a tissue culture incubator set at 37° C. and 5% CO$_2$. Medium was replaced every two days with serum-free medium until serum levels were undetectable. Subsequently, harvests were collected every two days and medium exchanged.

Purification of RAP-GAA for Uptake Assay:

RAP-GAA harvested in the medium from the spinner flasks was applied to a Blue-Sepharose column (Amersham) in low-salt buffer at neutral pH. Fusion was eluted with a linear salt gradient, and fractions containing fusion were loaded to a Heparin-Sepharose column (Amersham) and again eluted with a linear salt gradient. Eluted fractions containing activity were pooled and applied to a Phenyl-Sepharose column (Amersham). RAP-GAA was eluted from the Phenyl-Sepharose column with a decreasing salt step gradient. Eluted fractions were run on an SDS-PAGE gel and stained to determine relative percent purity. Based on gel analysis, peak activity fractions were about 70% pure. Fractions were pooled, concentrated using a 30 kD MWCO membrane (Millipore), and exchanged into phosphate-buffered saline at neutral pH.

The activity of the lysosomal enzyme in the fusion was determined to be unaffected by fusion to RAP. Purified human LRP (1 µg, recombinant, binding domain 2) was spotted onto PVDF filters in a 96-well dot-blot apparatus. Purified RAP-lysosomal enzyme fusion (RAP-LE) in Tris-buffered saline pH 7.5 with 5 mM $CaCl_2$ and 3% non-fat dry milk (TBS/Ca/BLOTTO) was overlayed on the immobilized LRP. Conditioned medium containing the RAP-LE, buffer alone and RAP alone were similarly incubated with immobilized LRP. Filters were washed three times to remove unbound protein. Duplicate filters were probed with anti-LE antibody or anti-RAP antibody. Blots were developed with chemiluminescent detection. The activity of the lysosomal enzyme was measured using fluorescent substrates. It was observed as shown in FIG. 10 that antibodies to either RAP or to the lysosomal enzyme detect LRP-bound RAP-LE, were found to bind to the fusion on Western blots, indicating that the fused proteins were intact and folded. Comparing signal intensity, it is further observed that the fusion is bound by the immobilized LRP to a similar extent as RAP alone.

Characterization of RAP-GAA Fusion:

Purified RAP-GAA was tested to determine identity, purity and carbohydrate content. For the identity test, fusion was resolved on SDS-PAGE, blotted to PVDF and probed with anti-GAA and anti-RAP antibodies. A single band of about 150 kD cross-reacted with both antibodies (FIG. 6). Fusion purity was determined by Coomassie Blue staining of the SDS-PAGE gel and was estimated to be >95%. Presence of complex oligosaccharides was measured by digestion with neuraminidase and comparison to undigested samples on an IEF gel. Neuraminidase digestion resulted in a quantitative shift in mobility to a more basic pI, consistent with the presence of complex oligosaccharides (FIG. 7). Endo H digestion was used to test for the presence of high-mannose oligosaccharides. Unlike control proteins, no change in molecular weight of the fusion was observed on SDS-PAGE gels after Endo H digestion. This suggests the absence of high-mannose oligosaccharides on the fusion (FIG. 8).

Purification of the RAP-IDU Fusion:

Blue sepharose 6 Fast Flow resin is used for the first purification step. The harvest fluid was adjusted to pH 7.0 and loaded onto a Blue-Sepharose column at a 70 mL/mL resin basis. The column was equilibrated with 75 mM NaCl, 20 mM $Na_2HPO_4$ pH 7.0. RAP-IDU eluted off the column at 1.2 M NaCl, 20 mM $Na_2HPO_4$ pH 7.0. The eluted fraction containing RAP-IDU (determined by iduronidase activity assay) was then exchanged into 75 mM NaCl, 20 mM $Na_2PO_4$ pH 7.0 and loaded onto a Heparin CL 6B resin. RAP-IDU was eluted from the Heparin column at 0.5 M NaCl pH 7.0. The eluted fusion was then adjusted to 2M NaCl, 20 mM $Na_2HPO_4$ pH 7.0 and loaded directly onto a Phenyl-Sepharose column. As a final step, RAP-IDU was eluted from this column at between 0.3 to 0.5M NaCl. Fusion purity was estimated by SDS-PAGE at >80% (FIG. 9).

Example III

Uptake and Distribution of Unconjugated RAP to the Brain

The distribution of RAP to brain was measured using a mouse in situ perfusion model. Volumes of distribution ($V_d$) for RAP, the positive control transferrin and the negative control albumin, were determined over a perfusion interval of 5 minutes. In addition, the relative quantities of the test proteins in the vascular and parenchymal fractions of the perfused brain were determined using the capillary depletion technique (Gutierrez, et al., J. Neuroimmunology 47(2):169-76 (1993)). The results shown in FIG. 11 include an observed, corrected $K_{influx}$ of 1 µL/g/min for transferrin. RAP had an observed, corrected $K_{influx}$ of 2.2 µL/g/min. RAP is taken up into brain.

Figure 11:
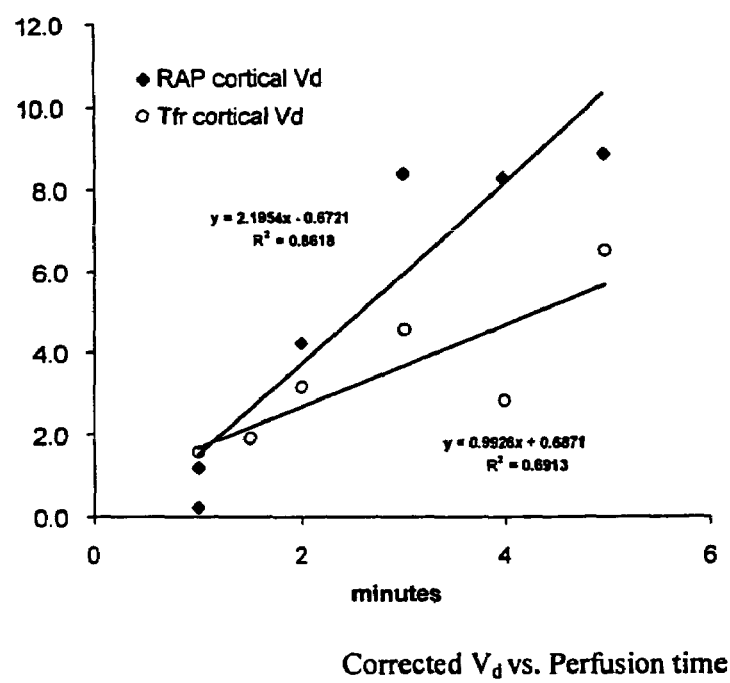
FIG. 11. Corrected $V_d$ vs. perfusion time for iodinated RAP and transferrin at 15 minutes.
Figure 12:
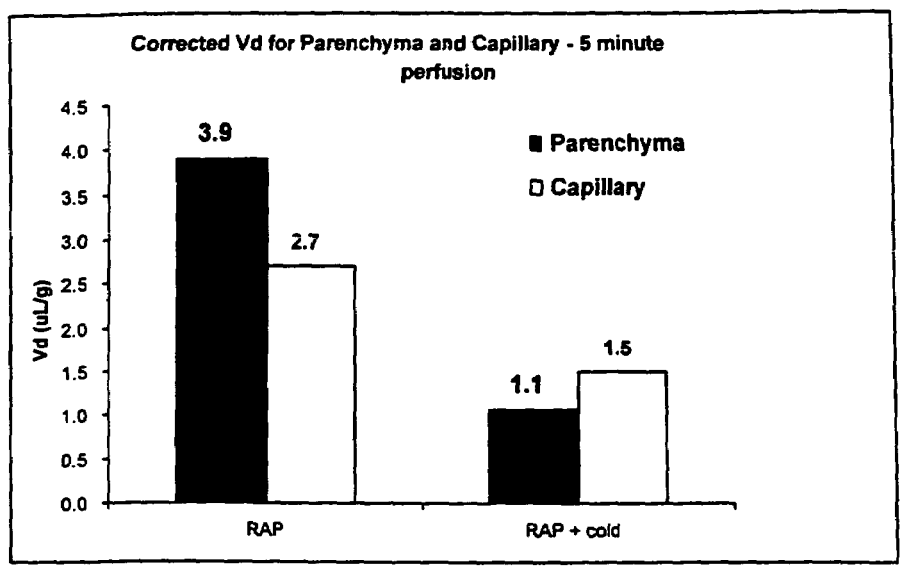
FIG. 12. Distribution of RAP between brain capillary endothelium and brain parenchyma.

A separate experiment was carried out at a single, 5-minute time-point to determine whether RAP is able to traverse the brain vasculature and enter the parenchyma. Brains were harvested as before, but were subjected to a capillary depletion procedure to determine the levels of RAP and albumin in the vascular and parenchymal spaces. Following harvest, the isolated cortex was weighed and placed in a Dounce homogenizer on ice. The cortex was immediately homogenized in 0.7 ml of capillary buffer (10 mM HEPES, 141 mM NaCl, 4 mM KCl, 2.8 mM $CaCl_2$, 1 mM $NaH_2PO_4$, 1 mM $MgSO_4$, 10 mM glucose, pH 7.4) for 10 strokes, after which 1.7 ml of 26% dextran was added and the mixture further homogenized with an additional 3 strokes on ice. To separate the different tissue fractions, 1.3 ml of the homogenate was loaded in an ultracentrifuge tube. The homogenate was centrifuged at 9000 rpm (5400×g) for 15 min at 4° C. in a Beckman TLV-100 swinging-bucket rotor. The parenchymal portion (supernatant) and the capillary portion (pellet) were than separately counted in a dual-channel gamma counter. A sample of post-CNS perfusate was also counted for the $V_d$ calculation. Unlabeled RAP was included as a competitor in some cases to determine whether uptake into brain tissue was saturable (5 µg of unlabeled RAP per mouse, about 80-fold excess over labeled RAP). Results were plotted as corrected $V_d$ (FIG. 11). Each data point is an average derived from 5-6 mice. FIG. 12 shows the distribution of RAP between brain capillary endothelium and brain parenchyma. These results indicate RAP crosses the blood-brain barrier to enter brain parenchyma and that the process of uptake is saturable.

Example IV

Measurement of Specific Uptake of RAP-GAA into Enzyme-deficient Patient Fibroblasts The uptake of RAGA into cells deficient in GAA was characterized. The cell line used was GM244 (Coriell Cell Repository), a primary cell line isolated from a patient with glycogen storage disorder type II (Pompe's disease). These fibroblasts take up phosphorylated, recombinant GAA via the mannose-6-phosphate receptor, but also have LRP1 receptors, which bind RAP. In order to identify the receptors involved in uptake of different test ligands, samples containing excess free RAP or mannose-6-phosphate were prepared.

Dilutions of RAP-GAA were made in the uptake medium (Dulbecco's Modified Eagle's Medium supplemented with 25 mM HEPES pH 7.0, 2 mM L-glutamine and 250 µg/mL bovine serum albumin) to yield fusion protein concentrations of 33, 11, 3.7, 1.2, 0.4, and 0.1 nM. The effect of 3 mM mannose-6-phosphate, 500 nM RAP and a combination of the two on the uptake of 5 nM RAP-GAA was also assayed. The GM244 fibroblasts was seeded into 12-well plates and allowed to grow for 3 days prior to the uptake experiment.

To initiate uptake, the growth medium was aspirated from the wells and each sample dispensed into duplicate wells at 1 ml per well. Plates were incubated for 4 hours at 37° C., 5% $CO_2$. Samples were then aspirated from each well, the wells washed with phosphate-buffered saline (PBS), and pre-warmed 0.25% trypsin/0.1% EDTA added to each well at 37° for 5 minutes to release the adherent cells. Released cells were pelleted and rinsed with chilled PBS. Pre-chilled lysis buffer (phosphatecitrate buffer, pH 4.0 with 0.15% Triton X-100) was then added and the pellets resuspended by gentle vortexing. Lysed cells could be stored at −80° C.

To measure the levels of GAA activity in the lysed cells, the frozen lysates were thawed at room temperature. Lysate (50 µl) was added directly to duplicate wells in 96-well opaque microtiter plates. Pre-warmed GAA fluorescent substrate (4-methylumbelliferyl-alpha-D-glucoside, 100 µL) was added to each well to initiate the reaction. The plate was incubated at 37° C. for 30 minutes and the reaction terminated by addition of 150 µl glycine/carbonate buffer pH 10. Fluorescence was measured in a plate reader at an excitation wavelength of 366 nm and an emission wavelength of 446 nm.

The results in FIG. 13 show that RAP-GAA is taken up by GM244 fibroblast cells. The $K_{uptake}$ was ~19 nM as determined by a non-linear fit enzymatic algorithm described in the GraFit software program (Sando and Neufeld 1977). Approximately 60-fold more RAP-GAA gets into the fibroblasts than recombinant GAA ($V_{max}$ ratio); 25-fold more at 10 nM. Additionally, 90% of the RAP-GAA fusion uptake is inhibited by 50 nM RAP while only 20% of the uptake is inhibited by 3 mM mannose 6-phosphate. The uptake of the native GAA is almost completely inhibited by mannose 6-phosphate, suggesting alternate receptor pathways for RAP-GAA and recombinant GAA.

Example V

Measurement of RAP-GAA Uptake and Lysosomal Localization in LRPnull CHO Cells Expressing Different LRP Receptor Family Members (LRP1B, LDLR, VLDLR) and into BN Cells Expressing Only LRP2 (Megalin, gp330)

Iodine labeling: RAP-GAA or recombinant GAA were radiolabeled with $^{125}I$ using the IODO-GEN reagent.

Cells were seeded in 12-well plates at a density of 200,000 cells/well and used after overnight culture. On the day of the experiment, cells were rinsed twice in ice-cold ligand binding buffer (Minimal Eagle's medium containing 0.6% bovine serum albumin (BSA)), and $^{125}I$-RAP-GAA or GAA alone were then added in the same buffer (0.5 ml/well). The initial ligand concentrations tested were 10 nM. Binding was carried out at 4° C. for 30 min with gentle rocking in the presence or absence of unlabeled 500 nM RAP or 10 mM mannose-6-phosphate to confirm receptor-binding specificity. Unbound ligand was then removed by washing cell monolayers three times with ice-cold binding buffer. Ice-cold stop/strip solution (0.2 M acetic acid, pH 2.6, 0.1 M NaCl) was then added to one set of plates without warming and kept on ice prior to counting. Dissociation constants for the receptor-ligand complexes were determined from the resulting binding data. The remaining plates were then placed in a 37° C. water bath, and 0.5 ml of ligand binding buffer prewarmed to 37° C. was added to the well monolayers to initiate internalization. At each time point (every 30 seconds for 2 2minutes and every 3 minutes thereafter) the wells were placed on ice, and the ligand-binding buffer replaced with ice-cold stop/strip solution. Ligand that remained on the cell surface was stripped by incubation for 20 minutes (0.75 ml for 10 minutes, twice) and counted. Internalization rates were determined from this data. Cell monolayers were then solubilized with SDS lysis buffer (62.5 mM Tris-HCl, pH 6.8, 0.2% SDS, and 10% (v/v) glycerol) and counted. The sum of ligand that was internalized added to that which remained on the cell surface after each assay was used as the maximum potential internalization. The fraction of internalized ligand after each time point was calculated and plotted.

Measurement of ligand degradation efficiency (transport to lysosomes after internalization): Cells were seeded at a density of 200,000 cells/well into 12-well dishes 1 day prior to assays. On the day of the experiment, pre-warmed assay buffer containing RAP-GAA or GAA alone was added to cell monolayers in the presence or absence of unlabeled 500 nM RAP or 10 mM mannose 6-phosphate, followed by incubation for 4 hours at 37° C. Following incubation, the medium overlaying the cell monolayers was removed and proteins were precipitated by addition of BSA to 10 mg/ml and trichloroacetic acid to a final concentration of 20%. Lysosomal degradation of ligands was defined as the appearance of radioactive fragments in the medium that were soluble in 20% trichloroacetic acid. The protein concentrations of each cell lysate were measured in parallel dishes that did not contain LRP ligands. The RAP-GAA and GAA degradation efficiencies were calculated as the value of degraded radioactive material (soluble cpm/mg cell protein) divided by the number of cell surface LRP family receptors (as determined previously by flow cytometry, data not shown).

Example VI

Measurement of Specific Uptake of RAP-LE in to Enzyme-deficient Patient Fibroblasts with Concomitant Clearance of Stored Glycosaminoglyeans Patient fibroblasts are seeded and grown to confluence in 12-well plates. On the day of the experiment, cells are fed with fresh medium lacking $MgSO_4$ and containing 4 µCi/mL of $Na_2{}^{35}SO_4$. Cells are also supplemented with RAP-LE fusion or LE alone in the presence or absence of 500 nM RAP or 10 mM mannose 6-phosphate. Cells are harvested each day for 4 days. After rinsing with PBS, cells are lysed by freeze-thaw. Stored GAG is assayed by precipitation with 80% ethanol and quantitated by scintillation counting. Stored GAG values are normalized to the protein content of the cell lysates.

Example VII

Measurement of Lysosomal Distribution and Clearance of Storage in Intravenously-administered RAP-GAA in GAA-deficient Mice GAA knock out mice (C57B1/6 background) were randomized to four treatment groups and treated every two days with 100 µl of either phosphate-buffered saline, 1.3 mg/kg or 0.33 mg/kg RAP-GAA fusion protein four times via intravenous tail vein injection. Forty-eight hours after the fourth injection, mice were euthanized by carbon dioxide inhalation and the brain, heart, diaphragm, upper and lower body skeletal muscle and liver immediately collected and flash frozen. Three age-matched wild-type mice were also euthanized and tissues collected and frozen. Each tissue is prepared for GAA immunohistochemical staining by embedding in OCT blocks, and for glycogen staining by fixing in glutaraldehyde and embedding in paraffin. The remaining tissues were tested for GAA activity using the fluorescent substrate assay described in Example IV. Serum was collected at sacrifice and tested for GAA antibody.

Dosing Regimen

| Group | #Animals | Test Articles Or Vehicle Articles | Dose (mg/kg) | #Doses | Dose Volume (μl) |
|---|---|---|---|---|---|
| 1 | 6 KO | PBS | — | 4 | 100 |
| 2 | 6 KO | RAP-GAA | 0.33 | 4 | 100 |
| 3 | 6 KO | RAP-GAA | 1.30 | 4 | 100 |
| 4 | 6 KO | GAA | 1.30 | 4 | 100 |
| 5 | 3 WT | None | None | None | None |

| | |
|---|---|
| Study day 0 | Inject groups 1-4 |
| Study day 2 | Inject groups 1-4 |
| Study day 4 | Inject groups 1-4 |
| Study day 7 | Inject groups 1-4 |
| Study day 9 | Bleed groups 1-4 and Sacrifice groups 1-5, Collect tissues groups 1-5 |

Example VIII

Treatment of Patients with MPS-I Disorder

A pharmaceutical composition comprising a conjugated agent comprising therapeutic enzyme linked to RAP is administered intravenously. The final dosage form of the fluid includes the conjugated agent, normal saline, phosphate buffer at pH 5.8 and human albumin at 1 mg/ml. These are prepared in a bag of normal saline.

A preferred composition comprises the conjugated agent (therapeutic enzyme linked to RAP) in an amount ranging from 0.05-0.5 mg/mL or 12,500-50,000 units per mL; sodium solution 150 mM; sodium phosphate buffer 10-50 mM, pH 5.8; human albumin 1 mg/mL. The composition may be in an intravenous bag of 50 to 250 ml.

Human patients manifesting a clinical phenotype of deficiency of lysosomal enzyme, such as in patients with MPS I with an alpha-L-iduronidase level of less than 1% of normal in leukocytes and fibroblasts are included in the study. All patients manifest some clinical evidence of visceral and soft tissue accumulation of glycosaminoglycans with varying degrees of functional impairment. Efficacy is determined by measuring the percentage reduction in urinary GAG excretion over time. The urinary GAG levels in MPS-I patients are compared to normal excretion values. There is a wide range of urine GAG values in untreated MPS-I patients. A greater than 50% reduction in excretion of undegraded GAGs following therapy with the conjugated agent is a valid means to measure an individual's response to therapy. For example, data is collected measuring the leukocyte iduronidase activity and buccal iduronidase activity before and after therapy in MPS I patients. Clinical assessment of liver and spleen size is performed as it is the most widely accepted means for evaluating successful bone marrow transplant treatment in MPS-I patients (Hoogerbrugge, et al., *Lancet* 345:1398 (1995)).

Example IX

Lysosomal Storage Diseases that may be Treated with Corresponding RAP-LE Conjugates The diseases that can be treated or prevented using the methods of the present invention are: Mucopolysaccharidosis I (MPS I), MPS II, MPS IIIA, MPS IIIB, Metachromatic Leukodystrophy (MLD), Krabbe, Pompe, Ceroid Lipofuscinosis, Tay-Sachs, Niemann-Pick A and B, and other lysosomal diseases. For each disease the conjugated agent would comprise a specific compound or enzyme. For methods involving MPS I, the preferred compound or enzyme is α-L-iduronidase. For methods involving MPS II, the preferred compound or enzyme iduronate-2-sulfatase. For methods involving MPS IIIA, the preferred compound or enzyme is heparan N-sulfatase. For methods involving MPS IIIB, the preferred compound or enzyme is α-N-acetylglucosaminidase. For methods involving Metachromatic Leukodystropy (MLD), the preferred compound or enzyme is arylsulfatase A. For methods involving Krabbe, the preferred compound or enzyme is galactosylceramidase. For methods involving Pompe, the preferred compound or enzyme is acid α-glucosidase. For methods involving CLN, the preferred compound or enzyme is tripeptidyl peptidase. For methods involving Tay-Sachs, the preferred compound or enzyme is hexosaminidase alpha. For methods involving Niemann-Pick A and B the preferred compound or enzyme is acid sphingomyelinase.

Each publication, patent application, patent, and other reference cited in any part of the specification is incorporated herein by reference in its entirety to the extent that it is not inconsistent with the present disclosure.

Based on the invention and examples disclosed herein, those skilled in the art will be able to develop other embodiments of the invention. The examples are not intended to limit the scope of the claims set out below in any way. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

We claim:

1. A method of delivering a therapeutic or diagnostic/investigational agent across the blood brain baffler (BBB) into the central nervous system in a subject in need thereof, said method comprising:
   administering to said subject a chimeric RAP fusion protein comprising said therapeutic or diagnostic/investigational agent, wherein the RAP portion of the chimeric RAP fusion protein consists of an amino acid sequence at least 80% identical to amino acids 221-323 of SEQ ID NO: 1.

2. The method of claim 1 wherein the agent is a therapeutic agent.

3. The method of claim 2 wherein the therapeutic agent is selected from the group consisting of neurotransmitters, glial-derived neurotrophic factor (GDNF), Nerve Growth Factor, Brain-Derived Neurotrophic Factor, Neurotrophin-3, Neurotrophin-4/5, aFGF, bFGF, CNTF, Leukemia Inhibitory Factor, Cardiotrophin-1, TGFβ, BMPs, GDFs, Neurturin, Artemin, Persephin, EGF, TGFα, Neuregulins, IGF-1, IGF-2, ADNF, PDGFs, caspase inhibitors, antibodies, antimicrobial agents and lymphokines.

4. The method of claim 1, wherein the subject is suffering from a neurological or psychological condition or disease.

5. The method of claim 4, wherein the subject is suffering from Alzheimer's disease (AD), Parkinson's disease (PD), multiple sclerosis (MS), or amyotrophic lateral sclerosis (ALS), schizophrenia, epilepsy, a neurological infection, or a neurological inflammatory condition.

6. The method of claim 4, wherein the subject is suffering from a brain tumor or tumor metastases in the brain and the chimeric RAP fusion protein further comprises a chemotherapeutic agent.

7. The method of claim 6 wherein the chemotherapeutic agent is adriamycin, cisplatin, 5-fluorouracil, camtothecin, or paclitaxel.

8. The method of claim 1 wherein the agent is a diagnostic/investigational agent and comprises a detectable label.

9. The method of claim 1 wherein the agent is conjugated to the RAP amino acid sequence via covalent bonding.

10. The method of claim 1 wherein the agent is conjugated to the RAP amino acid sequence via a peptide linker.

11. The method of claim 1 wherein said fragment is missing the endoplasmic reticulum retention signal at residues 320-323 of SEQ ID NO: 1.

12. A method of delivering a therapeutic or diagnostic/investigational agent across the blood brain barrier (BBB) into the central nervous system in a subject in need thereof, said method comprising:
    administering to said subject a chimeric RAP fusion protein comprising said therapeutic or diagnostic/investigational agent, wherein the RAP portion of the chimeric RAP fusion protein consists of a RAP fragment of 50 to 103 consecutive amino acids within residues 221-323 of SEQ ID NO: 1.

* * * * *

SEQUENCE LISTING

```
<160> NUMBER OF SEQ ID NOS: 28

<210> SEQ ID NO 1
<211> LENGTH: 323
<212> TYPE: PRT
<213> ORGANISM: Homo sapiens
```

<400> SEQUENCE: 1

```
Tyr Ser Arg Glu Lys Asn Gln Pro Lys Pro Ser Pro Lys Arg Glu Ser
1               5                   10                  15
Gly Glu Glu Phe Arg Met Glu Lys Leu Asn Gln Leu Trp Glu Lys Ala
            20                  25                  30
Gln Arg Leu His Leu Pro Pro Val Arg Leu Ala Glu Leu His Ala Asp
        35                  40                  45
Leu Lys Ile Gln Glu Arg Asp Glu Leu Ala Trp Lys Lys Leu Lys Leu
    50                  55                  60
Asp Gly Leu Asp Glu Asp Gly Lys Glu Ala Arg Leu Ile Arg Asn
65                  70                  75                  80
Leu Asn Val Ile Leu Ala Lys Tyr Gly Leu Asp Gly Lys Lys Asp Ala
                85                  90                  95
Arg Gln Val Thr Ser Asn Ser Leu Ser Gly Thr Gln Glu Asp Gly Leu
            100                 105                 110
Asp Asp Pro Arg Leu Glu Lys Leu Trp His Lys Ala Lys Thr Ser Gly
        115                 120                 125
Lys Phe Ser Gly Glu Glu Leu Asp Lys Leu Trp Arg Glu Phe Leu His
    130                 135                 140
His Lys Glu Lys Val His Glu Tyr Asn Val Leu Leu Glu Thr Leu Ser
145                 150                 155                 160
Arg Thr Glu Glu Ile His Glu Asn Val Ile Ser Pro Ser Asp Leu Ser
                165                 170                 175
Asp Ile Lys Gly Ser Val Leu His Ser Arg His Thr Glu Leu Lys Glu
            180                 185                 190
Lys Leu Arg Ser Ile Asn Gln Gly Leu Asp Arg Leu Arg Arg Val Ser
        195                 200                 205
His Gln Gly Tyr Ser Thr Glu Ala Glu Phe Glu Glu Pro Arg Val Ile
    210                 215                 220
Asp Leu Trp Asp Leu Ala Gln Ser Ala Asn Leu Thr Asp Lys Glu Leu
225                 230                 235                 240
Glu Ala Phe Arg Glu Glu Leu Lys His Phe Glu Ala Lys Ile Glu Lys
                245                 250                 255
His Asn His Tyr Gln Lys Gln Leu Glu Ile Ala His Glu Lys Leu Arg
            260                 265                 270
His Ala Glu Ser Val Gly Asp Gly Glu Arg Val Ser Arg Ser Arg Glu
        275                 280                 285
Lys His Ala Leu Leu Glu Gly Arg Thr Lys Glu Leu Gly Tyr Thr Val
    290                 295                 300
Lys Lys His Leu Gln Asp Leu Ser Gly Arg Ile Ser Arg Ala Arg His
305                 310                 315                 320
Asn Glu Leu
```

<210> SEQ ID NO 2
<211> LENGTH: 209
<212> TYPE: PRT
<213> ORGANISM: Homo sapiens

<400> SEQUENCE: 2

```
Pro Arg Leu Glu Lys Leu Trp His Lys Ala Lys Thr Ser Gly Lys Phe
1               5                   10                  15
Ser Gly Glu Glu Leu Asp Lys Leu Trp Arg Glu Phe Leu His His Lys
            20                  25                  30
Glu Lys Val His Glu Tyr Asn Val Leu Leu Glu Thr Leu Ser Arg Thr
```

-continued

```
                35                  40                  45
Glu Glu Ile His Glu Asn Val Ile Ser Pro Ser Asp Leu Ser Asp Ile
 50                  55                  60

Lys Gly Ser Val Leu His Ser Arg His Thr Glu Leu Lys Glu Lys Leu
 65                  70                  75                  80

Arg Ser Ile Asn Gln Gly Leu Asp Arg Leu Arg Arg Val Ser His Gln
                 85                  90                  95

Gly Tyr Ser Thr Glu Ala Glu Phe Glu Pro Arg Val Ile Asp Leu
                100                 105                 110

Trp Asp Leu Ala Gln Ser Ala Asn Leu Thr Asp Lys Glu Leu Glu Ala
            115                 120                 125

Phe Arg Glu Glu Leu Lys His Phe Glu Ala Lys Ile Glu Lys His Asn
        130                 135                 140

His Tyr Gln Lys Gln Leu Glu Ile Ala His Glu Lys Leu Arg His Ala
145                 150                 155                 160

Glu Ser Val Gly Asp Gly Glu Arg Val Ser Arg Ser Arg Glu Lys His
                165                 170                 175

Ala Leu Leu Glu Gly Arg Thr Lys Glu Leu Gly Tyr Thr Val Lys Lys
            180                 185                 190

His Leu Gln Asp Leu Ser Gly Arg Ile Ser Arg Ala Arg His Asn Glu
        195                 200                 205

Leu

<210> SEQ ID NO 3
<211> LENGTH: 33
<212> TYPE: DNA
<213> ORGANISM: Artificial sequence
<220> FEATURE:
<223> OTHER INFORMATION: Synthetic primer

<400> SEQUENCE: 3
ccgcgtggat cccccaggct ggaaaagctg tgg                                     33

<210> SEQ ID NO 4
<211> LENGTH: 35
<212> TYPE: DNA
<213> ORGANISM: Artificial sequence
<220> FEATURE:
<223> OTHER INFORMATION: Synthetic primer

<400> SEQUENCE: 4
tcaatgaatt ctcagagttc gttgtgccga gctct                                   35

<210> SEQ ID NO 5
<211> LENGTH: 205
<212> TYPE: PRT
<213> ORGANISM: Homo sapiens

<400> SEQUENCE: 5

Pro Arg Leu Glu Lys Leu Trp His Lys Ala Lys Thr Ser Gly Ile Ser
 1               5                  10                  15

Val Arg Leu Thr Ser Cys Ala Arg Val Leu His Tyr Lys Glu Lys Ile
                 20                  25                  30

His Glu Tyr Asn Val Leu Leu Asp Thr Leu Ser Arg Ala Glu Glu Gly
                 35                  40                  45

Tyr Glu Asn Leu Leu Ser Pro Ser Asp Met Thr His Ile Lys Ser Asp
 50                  55                  60

Thr Leu Ala Ser Lys His Ser Glu Leu Lys Asp Arg Leu Arg Ser Ile
```

```
                65                  70                  75                  80
Asn Gln Gly Leu Asp Arg Leu Arg Lys Val Ser His Gln Leu Arg Pro
                    85                  90                  95

Ala Thr Glu Phe Glu Glu Pro Arg Val Ile Asp Leu Trp Asp Leu Ala
                100                 105                 110

Gln Ser Ala Asn Phe Thr Glu Lys Glu Leu Glu Ser Phe Arg Glu Glu
            115                 120                 125

Leu Lys His Phe Glu Ala Lys Ile Glu Lys His Asn His Tyr Gln Lys
    130                 135                 140

Gln Leu Glu Ile Ser His Gln Lys Leu Lys His Val Glu Ser Ile Gly
145                 150                 155                 160

Asp Pro Glu His Ile Ser Arg Asn Lys Glu Lys Tyr Val Leu Leu Glu
                165                 170                 175

Glu Lys Thr Lys Glu Leu Gly Tyr Lys Val Lys Lys His Leu Gln Asp
                180                 185                 190

Leu Ser Ser Arg Val Ser Arg Ala Arg His Asn Glu Leu
            195                 200                 205

<210> SEQ ID NO 6
<211> LENGTH: 3702
<212> TYPE: DNA
<213> ORGANISM: Artificial sequence
<220> FEATURE:
<223> OTHER INFORMATION: RAP-GAA fusion sequence

<400> SEQUENCE: 6
cttaccgcca tgcggggtcc gagcggggct ctgtggctgc tcctggctct gcgcaccgtg      60
ctcggatcct actcgcggga gaagaaccag cccaagccgt ccccgaaacg cgagtccgga     120
gaggagttcc gcatggagaa gttgaaccag ctgtgggaga aggcccagcg actgcatctt     180
cctcccgtga ggctggccga gctccacgct gatctgaaga tacaggagag ggacgaactc     240
gcctggaaga aactaaagct tgacggcttg gacgaagatg gggagaagga agcgagactc     300
atacgcaacc tcaatgtcat cttggccaag tatggtctgg acggaaagaa ggacgctcgg     360
caggtgacca gcaactccct cagtggcacc caggaagacg ggctggatga ccccaggctg     420
gaaaagctgt ggcacaaggc gaagacctct gggaaattct ccggcgaaga actggacaag     480
ctctggcggg agttcctgca tcacaaagag aaagttcacg agtacaacgt cctgctggag     540
accctgagca ggaccgaaga atccacgag acgtcatta gccctcgga cctgagcgac      600 atcaagggca gcgtcctgca cagcaggcac acggagctga ggagaagct gcgcagcatc     660 aaccagggcc tggaccgcct gcgcagggtc agccaccagg gctacagcac tgaggctgag     720
ttcgaggagc ccagggtgat tgacctgtgg gacctggcgc agtccgccaa cctcacggac     780
aaggagctgg aggcgttccg ggaggagctc aagcacttcg agccaaaat cgagaagcac     840 aaccactacc agaagcagct ggagattgca cacgagaagc tgaggcacgc agagagcgtg     900
ggcgacggcg agcgtgtgag ccgcagccgc gagaagcacg ccctgctgga ggggcggacc     960
aaggagctgg gctacacggt gaagaagcat ctgcaggacc tgtccggcag gatctccaga    1020
gctcgcgccg aggcagaaac cggtgcacac cccggccgtc ccagagcagt gcccacacag    1080
tgcgacgtcc cccccaacag ccgcttcgat tgcccctg acaaggccat acccaggaa     1140 cagtgcgagg cccgcggctg ctgctacatc cctgcaaagc aggggctgca gggagcccag    1200
atggggcagc ctggtgcttc ttcccaccc agctaccca gctacaagct ggagaacctg    1260
agctcctctg aaatgggcta cacggccacc ctgacccgta ccacccccac cttcttcccc    1320
```

```
aaggacatcc tgaccctgcg gctggacgtg atgatggaga ctgagaaccg cctccacttc   1380
acgatcaaag atccagctaa caggcgctac gaggtgccct ggagaccccg cgtgtccac    1440
agccgggcac cgtccccact ctacagcgtg gagttctccg aggagccctt cggggtgatc   1500
gtgcaccggc agctggacgg ccgcgtgctg ctgaacacga cggtggcgcc cctgttcttt   1560
gcggaccagt tccttcagct gtccacctcg ctgcccctcgc agtatatcac aggcctcgcc  1620
gagcacctca gtcccctgat gctcagcacc agctggacca ggatcaccct gtggaaccgg   1680
gaccttgcgc ccacgcccgg tgcgaacctc tacgggtctc accctttcta cctggcgctg   1740
gaggacggcg ggtcggcaca cggggtgttc ctgctaaaca gcaatgccat ggatgtggtc   1800
ctgcagccga gccctgccct tagctggagg tcgacaggtg ggatcctgga tgtctacatc   1860
ttcctgggcc cagagcccaa gagcgtggtg cagcagtacc tggacgttgt gggatacccg   1920
ttcatgccgc catactgggg cctgggcttc acctgtgcc gctggggcta ctcctccacc    1980
gctatcaccc gccaggtggt ggagaacatg accagggccc acttcccct ggacgtccaa    2040
tggaacgacc tggactacat ggactcccgg agggacttca cgttcaacaa ggatggcttc   2100
cgggacttcc cggccatggt gcaggagctg caccagggcg gccggcgcta catgatgatc   2160
gtggatcctg ccatcagcag ctcgggcccct gccgggagct acaggcccta cgacgagggt  2220
ctgcggaggg gggttttcat caccaacgag accggccagc cgctgattgg gaaggtatgg   2280
cccgggtcca ctgccttccc cgacttcacc aaccccacag ccctggcctg gtgggaggac   2340
atggtggctg agttccatga ccaggtgccc ttcgacggct tgtggattga catgaacgag   2400
ccttccaact tcatcagagg ctctgaggac ggctgcccca caatgagct ggagaaccca    2460
ccctacgtgc ctggggtggt tgggggggacc ctccaggcgg ccaccatctg tgcctccagc  2520
caccagtttc tctccacaca ctacaacctg cacaacctct acggcctgac cgaagccatc   2580
gcctcccaca gggcgctggt gaaggctcgg gggacacgcc catttgtgat ctcccgctcg   2640
acctttgctg ccacggccg atacgccggc cactggacgg gggacgtgtg gagctcctgg   2700
gagcagctcg cctcctccgt gccagaaatc ctgcagtttta acctgctggg ggtgcctctg   2760
gtcggggccg acgtctgcgg cttcctgggc aacacctcag aggagctgtg tgtgcgctgg   2820
acccagctgg gggccttcta ccccttcatg cggaaccaca acagcctgct cagtctgccc   2880
caggagccgt acagcttcag cgagccggcc cagcaggcca tgaggaaggc cctcacccg   2940
cgctacgcac tcctcccca cctctacaca ctgttccacc aggcccacgt cgcgggggag   3000
accgtggccc ggcccctctt cctggagttc cccaaggact ctagcacctg gactgtggac   3060
caccagctct gtgggggga ggccctgctc atcacccccag tgctccaggc cgggaaggcc   3120
gaagtgactg gctacttccc cttgggcaca tggtacgacc tgcagacggt gccaatagag   3180
gcccttggca gctcccacc cccacctgca gctccccgtg agccagccat ccacagcgag   3240
gggcagtggg tgacgctgcc ggccccctg gacaccatca cgtccacct ccgggctggg    3300
tacatcatcc ccctgcaggg ccctggcctc acaaccacag agtccgcca gcagcccatg    3360
gccctggctg tggccctaac caagggtgga gaggcccgag gggagctgtt ctgggacgat   3420
ggagagagcc tggaagtgct ggagcgaggg gcctacacac aggtcatctt cctggccagg   3480
aataacacga tcgtgaatga gctggtacgt gtgaccagtg agggagctgg cctgcagctg   3540
cagaaggtga ctgtcctggg cgtgccacg gcgcccagc aggtcctctc caacggtgtc     3600
cctgtctcca acttcaccta cagccccgac accaaggtcc tggacatctg tgtctcgctg   3660
```
ttgatgggag agcagtttct cgtcagctgg tgttgactcg ag          3702

<210> SEQ ID NO 7
<211> LENGTH: 1228
<212> TYPE: PRT
<213> ORGANISM: Artificial sequence
<220> FEATURE:
<223> OTHER INFORMATION: RAP-GAA fusion sequence

<400> SEQUENCE: 7

Met Arg Gly Pro Ser Gly Ala Leu Trp Leu Leu Leu Ala Leu Arg Thr
1               5                   10                  15

Val Leu Gly Ser Tyr Ser Arg Glu Lys Asn Gln Pro Lys Pro Ser Pro
            20                  25                  30

Lys Arg Glu Ser Gly Glu Glu Phe Arg Met Glu Lys Leu Asn Gln Leu
        35                  40                  45

Trp Glu Lys Ala Gln Arg Leu His Leu Pro Pro Val Arg Leu Ala Glu
    50                  55                  60

Leu His Ala Asp Leu Lys Ile Gln Glu Arg Asp Glu Leu Ala Trp Lys
65                  70                  75                  80

Lys Leu Lys Leu Asp Gly Leu Asp Glu Asp Gly Glu Lys Glu Ala Arg
                85                  90                  95

Leu Ile Arg Asn Leu Asn Val Ile Leu Ala Lys Tyr Gly Leu Asp Gly
            100                 105                 110

Lys Lys Asp Ala Arg Gln Val Thr Ser Asn Ser Leu Ser Gly Thr Gln
        115                 120                 125

Glu Asp Gly Leu Asp Asp Pro Arg Leu Glu Lys Leu Trp His Lys Ala
    130                 135                 140

Lys Thr Ser Gly Lys Phe Ser Gly Glu Glu Leu Asp Lys Leu Trp Arg
145                 150                 155                 160

Glu Phe Leu His His Lys Glu Lys Val His Glu Tyr Asn Val Leu Leu
                165                 170                 175

Glu Thr Leu Ser Arg Thr Glu Glu Ile His Glu Asn Val Ile Ser Pro
            180                 185                 190

Ser Asp Leu Ser Asp Ile Lys Gly Ser Val Leu His Ser Arg His Thr
        195                 200                 205

Glu Leu Lys Glu Lys Leu Arg Ser Ile Asn Gln Gly Leu Asp Arg Leu
    210                 215                 220

Arg Arg Val Ser His Gln Gly Tyr Ser Thr Glu Ala Glu Phe Glu Glu
225                 230                 235                 240

Pro Arg Val Ile Asp Leu Trp Asp Leu Ala Gln Ser Ala Asn Leu Thr
                245                 250                 255

Asp Lys Glu Leu Glu Ala Phe Arg Glu Glu Leu Lys His Phe Glu Ala
            260                 265                 270

Lys Ile Glu Lys His Asn His Tyr Gln Lys Gln Leu Glu Ile Ala His
        275                 280                 285

Glu Lys Leu Arg His Ala Glu Ser Val Gly Asp Gly Glu Arg Val Ser
    290                 295                 300

Arg Ser Arg Glu Lys His Ala Leu Leu Glu Gly Arg Thr Lys Glu Leu
305                 310                 315                 320

Gly Tyr Thr Val Lys Lys His Leu Gln Asp Leu Ser Gly Arg Ile Ser
                325                 330                 335

Arg Ala Arg Ala Glu Ala Glu Thr Gly Ala His Pro Gly Arg Pro Arg
            340                 345                 350

Ala Val Pro Thr Gln Cys Asp Val Pro Pro Asn Ser Arg Phe Asp Cys

-continued

```
            355                 360                 365
Ala Pro Asp Lys Ala Ile Thr Gln Glu Gln Cys Glu Ala Arg Gly Cys
            370                 375                 380
Cys Tyr Ile Pro Ala Lys Gln Gly Leu Gln Gly Ala Gln Met Gly Gln
385                 390                 395                 400
Pro Trp Cys Phe Phe Pro Pro Ser Tyr Pro Ser Tyr Lys Leu Glu Asn
                    405                 410                 415
Leu Ser Ser Ser Glu Met Gly Tyr Thr Ala Thr Leu Thr Arg Thr Thr
                420                 425                 430
Pro Thr Phe Phe Pro Lys Asp Ile Leu Thr Leu Arg Leu Asp Val Met
            435                 440                 445
Met Glu Thr Glu Asn Arg Leu His Phe Thr Ile Lys Asp Pro Ala Asn
450                 455                 460
Arg Arg Tyr Glu Val Pro Leu Glu Thr Pro Arg Val His Ser Arg Ala
465                 470                 475                 480
Pro Ser Pro Leu Tyr Ser Val Glu Phe Ser Glu Glu Pro Phe Gly Val
                485                 490                 495
Ile Val His Arg Gln Leu Asp Gly Arg Val Leu Leu Asn Thr Thr Val
                500                 505                 510
Ala Pro Leu Phe Phe Ala Asp Gln Phe Leu Gln Leu Ser Thr Ser Leu
            515                 520                 525
Pro Ser Gln Tyr Ile Thr Gly Leu Ala Glu His Leu Ser Pro Leu Met
            530                 535                 540
Leu Ser Thr Ser Trp Thr Arg Ile Thr Leu Trp Asn Arg Asp Leu Ala
545                 550                 555                 560
Pro Thr Pro Gly Ala Asn Leu Tyr Gly Ser His Pro Phe Tyr Leu Ala
                565                 570                 575
Leu Glu Asp Gly Gly Ser Ala His Gly Val Phe Leu Leu Asn Ser Asn
                580                 585                 590
Ala Met Asp Val Val Leu Gln Pro Ser Pro Ala Leu Ser Trp Arg Ser
            595                 600                 605
Thr Gly Gly Ile Leu Asp Val Tyr Ile Phe Leu Gly Pro Glu Pro Lys
            610                 615                 620
Ser Val Val Gln Gln Tyr Leu Asp Val Val Gly Tyr Pro Phe Met Pro
625                 630                 635                 640
Pro Tyr Trp Gly Leu Gly Phe His Leu Cys Arg Trp Gly Tyr Ser Ser
                645                 650                 655
Thr Ala Ile Thr Arg Gln Val Val Glu Asn Met Thr Arg Ala His Phe
                660                 665                 670
Pro Leu Asp Val Gln Trp Asn Asp Leu Asp Tyr Met Asp Ser Arg Arg
            675                 680                 685
Asp Phe Thr Phe Asn Lys Asp Gly Phe Arg Asp Phe Pro Ala Met Val
            690                 695                 700
Gln Glu Leu His Gln Gly Gly Arg Arg Tyr Met Met Ile Val Asp Pro
705                 710                 715                 720
Ala Ile Ser Ser Ser Gly Pro Ala Gly Ser Tyr Arg Pro Tyr Asp Glu
                725                 730                 735
Gly Leu Arg Arg Gly Val Phe Ile Thr Asn Glu Thr Gly Gln Pro Leu
                740                 745                 750
Ile Gly Lys Val Trp Pro Gly Ser Thr Ala Phe Pro Asp Phe Thr Asn
            755                 760                 765
Pro Thr Ala Leu Ala Trp Trp Glu Asp Met Val Ala Glu Phe His Asp
            770                 775                 780
```

-continued

```
Gln Val Pro Phe Asp Gly Leu Trp Ile Asp Met Asn Glu Pro Ser Asn
785                 790                 795                 800

Phe Ile Arg Gly Ser Glu Asp Gly Cys Pro Asn Asn Glu Leu Glu Asn
                805                 810                 815

Pro Pro Tyr Val Pro Gly Val Val Gly Gly Thr Leu Gln Ala Ala Thr
            820                 825                 830

Ile Cys Ala Ser Ser His Gln Phe Leu Ser Thr His Tyr Asn Leu His
        835                 840                 845

Asn Leu Tyr Gly Leu Thr Glu Ala Ile Ala Ser His Arg Ala Leu Val
    850                 855                 860

Lys Ala Arg Gly Thr Arg Pro Phe Val Ile Ser Arg Ser Thr Phe Ala
865                 870                 875                 880

Gly His Gly Arg Tyr Ala Gly His Trp Thr Gly Asp Val Trp Ser Ser
                885                 890                 895

Trp Glu Gln Leu Ala Ser Ser Val Pro Glu Ile Leu Gln Phe Asn Leu
            900                 905                 910

Leu Gly Val Pro Leu Val Gly Ala Asp Val Cys Gly Phe Leu Gly Asn
        915                 920                 925

Thr Ser Glu Glu Leu Cys Val Arg Trp Thr Gln Leu Gly Ala Phe Tyr
    930                 935                 940

Pro Phe Met Arg Asn His Asn Ser Leu Leu Ser Leu Pro Gln Glu Pro
945                 950                 955                 960

Tyr Ser Phe Ser Glu Pro Ala Gln Gln Ala Met Arg Lys Ala Leu Thr
                965                 970                 975

Leu Arg Tyr Ala Leu Leu Pro His Leu Tyr Thr Leu Phe His Gln Ala
            980                 985                 990

His Val Ala Gly Glu Thr Val Ala Arg Pro Leu Phe Leu Glu Phe Pro
        995                 1000                1005

Lys Asp Ser Ser Thr Trp Thr Val Asp His Gln Leu Leu Trp Gly
    1010                1015                1020

Glu Ala Leu Leu Ile Thr Pro Val Leu Gln Ala Gly Lys Ala Glu
    1025                1030                1035

Val Thr Gly Tyr Phe Pro Leu Gly Thr Trp Tyr Asp Leu Gln Thr
    1040                1045                1050

Val Pro Ile Glu Ala Leu Gly Ser Leu Pro Pro Pro Ala Ala
    1055                1060                1065

Pro Arg Glu Pro Ala Ile His Ser Glu Gly Gln Trp Val Thr Leu
    1070                1075                1080

Pro Ala Pro Leu Asp Thr Ile Asn Val His Leu Arg Ala Gly Tyr
    1085                1090                1095

Ile Ile Pro Leu Gln Gly Pro Gly Leu Thr Thr Thr Glu Ser Arg
    1100                1105                1110

Gln Gln Pro Met Ala Leu Ala Val Ala Leu Thr Lys Gly Gly Glu
    1115                1120                1125

Ala Arg Gly Glu Leu Phe Trp Asp Asp Gly Glu Ser Leu Glu Val
    1130                1135                1140

Leu Glu Arg Gly Ala Tyr Thr Gln Val Ile Phe Leu Ala Arg Asn
    1145                1150                1155

Asn Thr Ile Val Asn Glu Leu Val Arg Val Thr Ser Glu Gly Ala
    1160                1165                1170

Gly Leu Gln Leu Gln Lys Val Thr Val Leu Gly Val Ala Thr Ala
    1175                1180                1185
```

```
Pro Gln Gln Val Leu Ser Asn Gly Val Pro Val Ser Asn Phe Thr
   1190               1195                1200

Tyr Ser Pro Asp Thr Lys Val Leu Asp Ile Cys Val Ser Leu Leu
   1205               1210                1215

Met Gly Glu Gln Phe Leu Val Ser Trp Cys
   1220               1225

<210> SEQ ID NO 8
<211> LENGTH: 2937
<212> TYPE: DNA
<213> ORGANISM: Artificial sequence
<220> FEATURE:
<223> OTHER INFORMATION: RAP-IDU fusion sequence

<400> SEQUENCE: 8
aagcttaccg ccatgcgggg tccgagcggg gctctgtggc tgctcctggc tctgcgcacc      60
gtgctcggat cctactcgcg ggagaagaac cagcccaagc cgtccccgaa acgcgagtcc     120
ggagaggagt tccgcatgga aagttgaac cagctgtggg agaaggccca gcgactgcat      180
```

```
Pro Gln Gln Val Leu Ser Asn Gly Val Pro Val Ser Asn Phe Thr
   1190               1195                1200

Tyr Ser Pro Asp Thr Lys Val Leu Asp Ile Cys Val Ser Leu Leu
   1205               1210                1215

Met Gly Glu Gln Phe Leu Val Ser Trp Cys
   1220               1225

<210> SEQ ID NO 8
<211> LENGTH: 2937
<212> TYPE: DNA
<213> ORGANISM: Artificial sequence
<220> FEATURE:
<223> OTHER INFORMATION: RAP-IDU fusion sequence

<400> SEQUENCE: 8
aagcttaccg ccatgcgggg tccgagcggg gctctgtggc tgctcctggc tctgcgcacc      60
gtgctcggat cctactcgcg ggagaagaac cagcccaagc cgtccccgaa acgcgagtcc     120
ggagaggagt tccgcatgga aagttgaac cagctgtggg agaaggccca gcgactgcat     180
cttcctcccg tgaggctggc cgagctccac gctgatctga agatacagga gagggacgaa     240
ctcgcctgga agaaactaaa gcttgacggc ttggacgaag atggggagaa ggaagcgaga     300
ctcatacgca acctcaatgt catcttggcc aagtatggtc tggacggaaa gaaggacgct     360
cggcaggtga ccagcaactc cctcagtggc acccaggaag acgggctgga tgacccagg      420 ctggaaaagc tgtggcacaa ggcgaagacc tctgggaaat ctccggcga agaactggac     480 aagctctggc gggagttcct gcatcacaaa gagaaagttc acgagtacaa cgtcctgctg     540
gagaccctga gcaggaccga gaaatccac gagaacgtca ttagcccctc ggacctgagc     600
gacatcaagg cagcgtcct gcacagcagg cacacggagc tgaaggagaa gctgcgcagc     660
atcaaccagg gcctggaccg cctgcgcagg gtcagccacc agggctacag cactgaggct     720
gagttcgagg agcccagggt gattgacctg tgggacctgg cgcagtccgc caacctcacg     780
gacaaggagc tggaggcgtt ccgggaggag ctcaagcact tcgaagccaa atcgagaag     840 cacaaccact accagaagca gctggagatt gcgcacgaga gctgaggca cgcagagagc     900 gtgggcgacg gcgagcgtgt gagccgcagc gcgagaagc acgccctgct ggaggggcgg     960
accaaggagc tgggctacac ggtgaagaag catctgcagg acctgtccgg caggatctcc    1020
agagctcgcg ccgaggcaga aaccggtgag gccccgcacc tggtgcatgt ggacgcggcc    1080
cgcgcgctgt ggccctgcg gcgcttctgg aggagcacag gcttctgccc ccgctgcca     1140 cacagccagg ctgaccagta cgtcctcagc tgggaccagc agctcaacct cgcctatgtg    1200
ggcgccgtcc ctcaccgcgg catcaagcag gtccggaccc actggctgct ggagcttgtc    1260
accaccaggg ggtccactgg acggggcctg agctacaact tcacccacct ggacgggtac    1320
ttggaccttc tcagggagaa ccagctcctc ccagggtttg agctgatggg cagcgcctcg    1380
ggccacttca ctgactttga ggacaagcag caggtgtttg agtggaagga cttggtctcc    1440
agcctggcca ggagatacat cggtaggtac ggactggcgc atgtttccaa gtggaacttc    1500
gagacgtgga atgagccaga ccaccacgac tttgacaacg tctccatgac catgcaaggc    1560
ttcctgaact actacgatgc ctgctcggag ggtctgcgcg ccgccagccc cgccctgcgg    1620
ctgggaggcc ccggcgactc cttccacacc ccaccgcgat cccgctgag ctggggcctc     1680 ctgcgccact gccacgacgg taccaacttc ttcactgggg aggcgggcgt gcggctggac    1740
tacatctccc tccacaggaa gggtgcgcgc agctccatct ccatcctgga gcaggagaag    1800
```

-continued

```
gtcgtcgcgc agcagatccg gcagctcttc cccaagttcg cggacacccc catttacaac    1860
gacgaggcgg acccgctggt gggctggtcc ctgccacagc cgtggagggc ggacgtgacc    1920
tacgcggcca tggtggtgaa ggtcatcgcg cagcatcaga acctgctact ggccaacacc    1980
acctccgcct tccctacgc gctcctgagc aacgacaatg ccttcctgag ctaccacccg    2040
caccccttcg cgcagcgcac gctcaccgcg cgcttccagg tcaacaacac ccgcccgccg    2100
cacgtgcagc tgttgcgcaa gccggtgctc acggccatgg ggctgctggc gctgctggat    2160
gaggagcagc tctgggccga agtgtcgcag gccgggaccg tcctggacag caaccacacg    2220
gtgggcgtcc tggccagcgc ccaccgcccc cagggcccgg ccgacgcctg gcgcgccgcg    2280
gtgctgatct acgcgagcga cgacacccgc gcccacccca accgcagcgt cgcggtgacc    2340
ctgcggctgc gcggggtgcc ccccggcccg ggcctggtct acgtcacgcg ctacctggac    2400
aacgggctct gcagccccga cggcgagtgg cggcgcctgg gccggcccgt cttccccacg    2460
gcagagcagt tccggcgcat gcgcgcgggct gaggacccgg tggccgcggc gccccgcccc    2520
ttacccgccg gcggccgcct gaccctgcgc cccgcgctgc ggctgccgtc gcttttgctg    2580
gtgcacgtgt gtgcgcgccc cgagaagccc cccgggcagg tcacgcggct ccgcgccctg    2640
cccctgaccc aagggcagct ggttctggtc tggtcggatg aacacgtggg ctccaagtgc    2700
ctgtggacat acgagatcca gttctctcag gacggtaagg cgtacacccc ggtcagcagg    2760
aagccatcga ccttcaacct ctttgtgttc agcccagaca caggtgctgt ctctggctcc    2820
taccgagttc gagccctgga ctactgggcc cgaccaggcc ccttctcgga ccctgtgccg    2880
tacctggagg tccctgtgcc aagagggccc ccatccccgg gcaatccatg actcgag     2937
```

<210> SEQ ID NO 9
<211> LENGTH: 972
<212> TYPE: PRT
<213> ORGANISM: Artificial sequence
<220> FEATURE:
<223> OTHER INFORMATION: RAP-IDU fusion sequence

<400> SEQUENCE: 9

```
Met Arg Gly Pro Ser Gly Ala Leu Trp Leu Leu Leu Ala Leu Arg Thr
1               5                   10                  15

Val Leu Gly Ser Tyr Ser Arg Glu Lys Asn Gln Pro Lys Pro Ser Pro
            20                  25                  30

Lys Arg Glu Ser Gly Glu Glu Phe Arg Met Glu Lys Leu Asn Gln Leu
        35                  40                  45

Trp Glu Lys Ala Gln Arg Leu His Leu Pro Pro Val Arg Leu Ala Glu
    50                  55                  60

Leu His Ala Asp Leu Lys Ile Gln Glu Arg Asp Glu Leu Ala Trp Lys
65                  70                  75                  80

Lys Leu Lys Leu Asp Gly Leu Asp Glu Asp Gly Glu Lys Glu Ala Arg
                85                  90                  95

Leu Ile Arg Asn Leu Asn Val Ile Leu Ala Lys Tyr Gly Leu Asp Gly
            100                 105                 110

Lys Lys Asp Ala Arg Gln Val Thr Ser Asn Ser Leu Ser Gly Thr Gln
        115                 120                 125

Glu Asp Gly Leu Asp Asp Pro Arg Leu Glu Lys Leu Trp His Lys Ala
    130                 135                 140

Lys Thr Ser Gly Lys Phe Ser Gly Glu Glu Leu Asp Lys Leu Trp Arg
145                 150                 155                 160

Glu Phe Leu His His Lys Glu Lys Val His Glu Tyr Asn Val Leu Leu
```

-continued

```
            165                 170                 175
Glu Thr Leu Ser Arg Thr Glu Ile His Glu Asn Val Ile Ser Pro
        180                 185                 190
Ser Asp Leu Ser Asp Ile Lys Gly Ser Val Leu His Ser Arg His Thr
        195                 200                 205
Glu Leu Lys Glu Lys Leu Arg Ser Ile Asn Gln Gly Leu Asp Arg Leu
        210                 215                 220
Arg Arg Val Ser His Gln Gly Tyr Ser Thr Glu Ala Glu Phe Glu Glu
225                 230                 235                 240
Pro Arg Val Ile Asp Leu Trp Asp Leu Ala Gln Ser Ala Asn Leu Thr
                245                 250                 255
Asp Lys Glu Leu Glu Ala Phe Arg Glu Glu Leu Lys His Phe Glu Ala
        260                 265                 270
Lys Ile Glu Lys His Asn His Tyr Gln Lys Gln Leu Glu Ile Ala His
        275                 280                 285
Glu Lys Leu Arg His Ala Glu Ser Val Gly Asp Gly Glu Arg Val Ser
        290                 295                 300
Arg Ser Arg Glu Lys His Ala Leu Leu Glu Gly Arg Thr Lys Glu Leu
305                 310                 315                 320
Gly Tyr Thr Val Lys Lys His Leu Gln Asp Leu Ser Gly Arg Ile Ser
                325                 330                 335
Arg Ala Arg Ala Glu Ala Glu Thr Gly Glu Ala Pro His Leu Val His
            340                 345                 350
Val Asp Ala Ala Arg Ala Leu Trp Pro Leu Arg Arg Phe Trp Arg Ser
        355                 360                 365
Thr Gly Phe Cys Pro Pro Leu Pro His Ser Gln Ala Asp Gln Tyr Val
    370                 375                 380
Leu Ser Trp Asp Gln Gln Leu Asn Leu Ala Tyr Val Gly Ala Val Pro
385                 390                 395                 400
His Arg Gly Ile Lys Gln Val Arg Thr His Trp Leu Leu Glu Leu Val
                405                 410                 415
Thr Thr Arg Gly Ser Thr Gly Arg Gly Leu Ser Tyr Asn Phe Thr His
            420                 425                 430
Leu Asp Gly Tyr Leu Asp Leu Arg Glu Asn Gln Leu Leu Pro Gly
        435                 440                 445
Phe Glu Leu Met Gly Ser Ala Ser Gly His Phe Thr Asp Phe Glu Asp
    450                 455                 460
Lys Gln Gln Val Phe Glu Trp Lys Asp Leu Val Ser Ser Leu Ala Arg
465                 470                 475                 480
Arg Tyr Ile Gly Arg Tyr Gly Leu Ala His Val Ser Lys Trp Asn Phe
                485                 490                 495
Glu Thr Trp Asn Glu Pro Asp His His Asp Phe Asp Asn Val Ser Met
            500                 505                 510
Thr Met Gln Gly Phe Leu Asn Tyr Tyr Asp Ala Cys Ser Glu Gly Leu
        515                 520                 525
Arg Ala Ala Ser Pro Ala Leu Arg Leu Gly Gly Pro Gly Asp Ser Phe
    530                 535                 540
His Thr Pro Pro Arg Ser Pro Leu Ser Trp Gly Leu Leu Arg His Cys
545                 550                 555                 560
His Asp Gly Thr Asn Phe Phe Thr Gly Glu Ala Gly Val Arg Leu Asp
                565                 570                 575
Tyr Ile Ser Leu His Arg Lys Gly Ala Arg Ser Ser Ile Ser Ile Leu
            580                 585                 590
```

```
Glu Gln Glu Lys Val Val Ala Gln Gln Ile Arg Gln Leu Phe Pro Lys
            595                 600                 605

Phe Ala Asp Thr Pro Ile Tyr Asn Asp Glu Ala Asp Pro Leu Val Gly
        610                 615                 620

Trp Ser Leu Pro Gln Pro Trp Arg Ala Asp Val Thr Tyr Ala Ala Met
625                 630                 635                 640

Val Val Lys Val Ile Ala Gln His Gln Asn Leu Leu Leu Ala Asn Thr
                645                 650                 655

Thr Ser Ala Phe Pro Tyr Ala Leu Leu Ser Asn Asp Asn Ala Phe Leu
            660                 665                 670

Ser Tyr His Pro His Pro Phe Ala Gln Arg Thr Leu Thr Ala Arg Phe
        675                 680                 685

Gln Val Asn Asn Thr Arg Pro Pro His Val Gln Leu Leu Arg Lys Pro
690                 695                 700

Val Leu Thr Ala Met Gly Leu Leu Ala Leu Leu Asp Glu Gln Leu
705                 710                 715                 720

Trp Ala Glu Val Ser Gln Ala Gly Thr Val Leu Asp Ser Asn His Thr
                725                 730                 735

Val Gly Val Leu Ala Ser Ala His Arg Pro Gln Gly Pro Ala Asp Ala
            740                 745                 750

Trp Arg Ala Ala Val Leu Ile Tyr Ala Ser Asp Asp Thr Arg Ala His
        755                 760                 765

Pro Asn Arg Ser Val Ala Val Thr Leu Arg Leu Arg Gly Val Pro Pro
770                 775                 780

Gly Pro Gly Leu Val Tyr Val Thr Arg Tyr Leu Asp Asn Gly Leu Cys
785                 790                 795                 800

Ser Pro Asp Gly Glu Trp Arg Arg Leu Gly Arg Pro Val Phe Pro Thr
                805                 810                 815

Ala Glu Gln Phe Arg Arg Met Arg Ala Ala Glu Asp Pro Val Ala Ala
            820                 825                 830

Ala Pro Arg Pro Leu Pro Ala Gly Gly Arg Leu Thr Leu Arg Pro Ala
        835                 840                 845

Leu Arg Leu Pro Ser Leu Leu Leu Val His Val Cys Ala Arg Pro Glu
850                 855                 860

Lys Pro Pro Gly Gln Val Thr Arg Leu Arg Ala Leu Pro Leu Thr Gln
865                 870                 875                 880

Gly Gln Leu Val Leu Val Trp Ser Asp Glu His Val Gly Ser Lys Cys
                885                 890                 895

Leu Trp Thr Tyr Glu Ile Gln Phe Ser Gln Asp Gly Lys Ala Tyr Thr
            900                 905                 910

Pro Val Ser Arg Lys Pro Ser Thr Phe Asn Leu Phe Val Phe Ser Pro
        915                 920                 925

Asp Thr Gly Ala Val Ser Gly Ser Tyr Arg Val Arg Ala Leu Asp Tyr
930                 935                 940

Trp Ala Arg Pro Gly Pro Phe Ser Asp Pro Val Pro Tyr Leu Glu Val
945                 950                 955                 960

Pro Val Pro Arg Gly Pro Pro Ser Pro Gly Asn Pro
                965                 970

<210> SEQ ID NO 10
<211> LENGTH: 1398
<212> TYPE: DNA
<213> ORGANISM: Artificial sequence
<220> FEATURE:
```

-continued

<223> OTHER INFORMATION: RAP-GDNF fusion sequence

<400> SEQUENCE: 10

```
atgggggtt cttactcgcg ggagaagaac cagcccaagc cgtccccgaa acgcgagtcc      60
ggagaggagt tccgcatgga gaagttgaac cagctgtggg agaaggccca gcgactgcat    120
cttcctcccg tgaggctggc cgagctccac gctgatctga agatacagga gagggacgaa    180
ctcgcctgga agaaactaaa gcttgacggc ttggacgaag atgggggagaa ggaagcgaga    240
ctcatacgca acctcaatgt catcttggcc aagtatggtc tggacggaaa gaaggacgct    300
cggcaggtga ccagcaactc cctcagtggc acccaggaag acgggctgga tgaccccagg    360
ctggaaaagc tgtggcacaa ggcgaagacc tctgggaaat ctccggcga gaactggac    420
aagctctggc gggagttcct gcatcacaaa gagaaagttc acgagtacaa cgtcctgctg    480
gagaccctga gcaggaccga gaaatccac gagaacgtca ttagccctc ggacctgagc    540
gacatcaagg gcagcgtcct gcacagcagg cacacggagc tgaaggagaa gctgcgcagc    600
atcaaccagg gcctggaccg cctgcgcagg gtcagccacc agggctacag cactgaggct    660
gagttcgagagc cccagggt gattgacctg tgggacctgg cgcagtccgc caacctcacg    720
gacaaggagc tggaggcgtt ccgggaggag ctcaagcact tcgaagccaa atcgagaag    780
cacaaccact accagaagca gctggagatt gcgcacgaga gctgaggca cgcagagagc    840
gtgggcgacg gcgagcgtgt gagccgcagc cgcgagaagc acgccctgct ggaggggcgg    900
accaaggagc tgggctacac ggtgaagaag catctgcagg acctgtccgg caggatctcc    960
agagctcggg ccgaggcaga aaccggttca ccagataaac aaatggcagt gcttcctaga   1020
agagagcgga tcggcaggc tgcagctgcc aacccagaga attccagagg aaaaggtcgg   1080
agaggccaga ggggcaaaaa ccggggttgt gtcttaactg caatacattt aaatgtcact   1140
gacttgggtc tgggctatga accaaggag gaactgattt ttaggtactg cagcggctct   1200
tgcgatgcag ctgagacaac gtacgacaaa atattgaaaa acttatccag aaatagaagg   1260
ctggtgagtg acaaagtagg gcaggcatgt tgcagaccca tcgcctttga tgatgacctg   1320
tcgttttta atgataaccct ggtttaccat attctaagaa agcattccgc taaaggtgt    1380
ggatgtatct gatctaga                                                  1398
```

<210> SEQ ID NO 11
<211> LENGTH: 463
<212> TYPE: PRT
<213> ORGANISM: Artificial sequence
<220> FEATURE:
<223> OTHER INFORMATION: RAP-GDNF fusion sequence

<400> SEQUENCE: 11

```
Met Gly Gly Ser Tyr Ser Arg Glu Lys Asn Gln Pro Lys Pro Ser Pro
1               5                   10                  15

Lys Arg Glu Ser Gly Glu Glu Phe Arg Met Glu Lys Leu Asn Gln Leu
                20                  25                  30

Trp Glu Lys Ala Gln Arg Leu His Leu Pro Pro Val Arg Leu Ala Glu
            35                  40                  45

Leu His Ala Asp Leu Lys Ile Gln Glu Arg Asp Glu Leu Ala Trp Lys
        50                  55                  60

Lys Leu Lys Leu Asp Gly Leu Asp Glu Asp Gly Glu Lys Glu Ala Arg
65                  70                  75                  80

Leu Ile Arg Asn Leu Asn Val Ile Leu Ala Lys Tyr Gly Leu Asp Gly
                85                  90                  95
```

Lys Lys Asp Ala Arg Gln Val Thr Ser Asn Ser Leu Ser Gly Thr Gln
                100                 105                 110

Glu Asp Gly Leu Asp Asp Pro Arg Leu Glu Lys Leu Trp His Lys Ala
            115                 120                 125

Lys Thr Ser Gly Lys Phe Ser Gly Glu Leu Asp Lys Leu Trp Arg
        130                 135                 140

Glu Phe Leu His His Lys Glu Lys Val His Glu Tyr Asn Val Leu Leu
145                 150                 155                 160

Glu Thr Leu Ser Arg Thr Glu Glu Ile His Glu Asn Val Ile Ser Pro
                165                 170                 175

Ser Asp Leu Ser Asp Ile Lys Gly Ser Val Leu His Ser Arg His Thr
            180                 185                 190

Glu Leu Lys Glu Lys Leu Arg Ser Ile Asn Gln Gly Leu Asp Arg Leu
        195                 200                 205

Arg Arg Val Ser His Gln Gly Tyr Ser Thr Glu Ala Glu Phe Glu Glu
    210                 215                 220

Pro Arg Val Ile Asp Leu Trp Asp Leu Ala Gln Ser Ala Asn Leu Thr
225                 230                 235                 240

Asp Lys Glu Leu Glu Ala Phe Arg Glu Glu Leu Lys His Phe Glu Ala
                245                 250                 255

Lys Ile Glu Lys His Asn His Tyr Gln Lys Gln Leu Glu Ile Ala His
            260                 265                 270

Glu Lys Leu Arg His Ala Glu Ser Val Gly Asp Gly Glu Arg Val Ser
        275                 280                 285

Arg Ser Arg Glu Lys His Ala Leu Leu Glu Gly Arg Thr Lys Glu Leu
    290                 295                 300

Gly Tyr Thr Val Lys Lys His Leu Gln Asp Leu Ser Gly Arg Ile Ser
305                 310                 315                 320

Arg Ala Arg Ala Glu Ala Glu Thr Gly Ser Pro Asp Lys Gln Met Ala
                325                 330                 335

Val Leu Pro Arg Arg Glu Arg Asn Arg Gln Ala Ala Ala Asn Pro
            340                 345                 350

Glu Asn Ser Arg Gly Lys Gly Arg Gly Gln Arg Gly Lys Asn Arg
        355                 360                 365

Gly Cys Val Leu Thr Ala Ile His Leu Asn Val Thr Asp Leu Gly Leu
    370                 375                 380

Gly Tyr Glu Thr Lys Glu Glu Leu Ile Phe Arg Tyr Cys Ser Gly Ser
385                 390                 395                 400

Cys Asp Ala Ala Glu Thr Thr Tyr Asp Lys Ile Leu Lys Asn Leu Ser
                405                 410                 415

Arg Asn Arg Arg Leu Val Ser Asp Lys Val Gly Gln Ala Cys Cys Arg
            420                 425                 430

Pro Ile Ala Phe Asp Asp Leu Ser Phe Leu Asp Asp Asn Leu Val
        435                 440                 445

Tyr His Ile Leu Arg Lys His Ser Ala Lys Arg Cys Gly Cys Ile
    450                 455                 460

<210> SEQ ID NO 12
<211> LENGTH: 49
<212> TYPE: DNA
<213> ORGANISM: Artificial sequence
<220> FEATURE:
<223> OTHER INFORMATION: Synthetic primer

<400> SEQUENCE: 12

```
gcgataggat cctactcgcg ggagaagaac cagcccaagc cgtccccga                    49

<210> SEQ ID NO 13
<211> LENGTH: 57
<212> TYPE: DNA
<213> ORGANISM: Artificial sequence
<220> FEATURE:
<223> OTHER INFORMATION: Synthetic primer

<400> SEQUENCE: 13
gcgataaacc ggtttctgcc tcggcgcgag ctctggagat cctgccggac aggtcct         57

<210> SEQ ID NO 14
<211> LENGTH: 39
<212> TYPE: DNA
<213> ORGANISM: Artificial sequence
<220> FEATURE:
<223> OTHER INFORMATION: Synthetic primer

<400> SEQUENCE: 14
gcgataaccg gtgcacaccc cggccgtccc agagcagtg                              39

<210> SEQ ID NO 15
<211> LENGTH: 37
<212> TYPE: DNA
<213> ORGANISM: Artificial sequence
<220> FEATURE:
<223> OTHER INFORMATION: Synthetic primer

<400> SEQUENCE: 15
gcgatactcg agtcaacacc agctgacgag aaactgc                                37

<210> SEQ ID NO 16
<211> LENGTH: 46
<212> TYPE: DNA
<213> ORGANISM: Artificial sequence
<220> FEATURE:
<223> OTHER INFORMATION: Synthetic primer

<400> SEQUENCE: 16
gcgataaccg gtgaggcccc ccgcacctgg tgcatgtgga cgcggc                      46

<210> SEQ ID NO 17
<211> LENGTH: 45
<212> TYPE: DNA
<213> ORGANISM: Artificial sequence
<220> FEATURE:
<223> OTHER INFORMATION: Synthetic primer

<400> SEQUENCE: 17
gcgatactcg agtcatggat tgcccgggga tggggccct cttgg                        45

<210> SEQ ID NO 18
<211> LENGTH: 33
<212> TYPE: DNA
<213> ORGANISM: Artificial sequence
<220> FEATURE:
<223> OTHER INFORMATION: Synthetic primer

<400> SEQUENCE: 18
acagtgaccg gttcaccaga taaacaaatg gca                                    33

<210> SEQ ID NO 19
<211> LENGTH: 38
<212> TYPE: DNA
```

```
<213> ORGANISM: Artificial sequence
<220> FEATURE:
<223> OTHER INFORMATION: Synthetic primer

<400> SEQUENCE: 19
acagtgctcg agtctagatc agatacatcc acacctttt                              38

<210> SEQ ID NO 20
<211> LENGTH: 51
<212> TYPE: DNA
<213> ORGANISM: Artificial sequence
<220> FEATURE:
<223> OTHER INFORMATION: Synthetic primer

<400> SEQUENCE: 20
acagtggcca tgggggttc ttactcgcgg gagaagaacc agcccaagcc g                 51

<210> SEQ ID NO 21
<211> LENGTH: 357
<212> TYPE: PRT
<213> ORGANISM: Homo sapiens

<400> SEQUENCE: 21
```

Met Ala Pro Arg Arg Val Arg Ser Phe Leu Arg Gly Leu Pro Ala Leu
1               5                   10                  15

Leu Leu Leu Leu Phe Leu Gly Pro Trp Pro Ala Ala Ser His Gly
            20                  25                  30

Gly Lys Tyr Ser Arg Glu Lys Asn Gln Pro Lys Pro Ser Pro Lys Arg
        35                  40                  45

Glu Ser Gly Glu Glu Phe Arg Met Glu Lys Leu Asn Gln Leu Trp Glu
    50                  55                  60

Lys Ala Gln Arg Leu His Leu Pro Pro Val Arg Leu Ala Glu Leu His
65                  70                  75                  80

Ala Asp Leu Lys Ile Gln Glu Arg Asp Glu Leu Ala Trp Lys Lys Leu
                85                  90                  95

Lys Leu Asp Gly Leu Asp Glu Asp Gly Glu Lys Glu Ala Arg Leu Ile
            100                 105                 110

Arg Asn Leu Asn Val Ile Leu Ala Lys Tyr Gly Leu Asp Gly Lys Lys
        115                 120                 125

Asp Ala Arg Gln Val Thr Ser Asn Ser Leu Ser Gly Thr Gln Glu Asp
    130                 135                 140

Gly Leu Asp Asp Pro Arg Leu Glu Lys Leu Trp His Lys Ala Lys Thr
145                 150                 155                 160

Ser Gly Lys Phe Ser Gly Glu Glu Leu Asp Lys Leu Trp Arg Glu Phe
                165                 170                 175

Leu His His Lys Glu Lys Val His Glu Tyr Asn Val Leu Leu Glu Thr
            180                 185                 190

Leu Ser Arg Thr Glu Glu Ile His Glu Asn Val Ile Ser Pro Ser Asp
        195                 200                 205

Leu Ser Asp Ile Lys Gly Ser Val Leu His Ser Arg His Thr Glu Leu
    210                 215                 220

Lys Glu Lys Leu Arg Ser Ile Asn Gln Gly Leu Asp Arg Leu Arg Arg
225                 230                 235                 240

Val Ser His Gln Gly Tyr Ser Thr Glu Ala Glu Phe Glu Glu Pro Arg
                245                 250                 255

Val Ile Asp Leu Trp Asp Leu Ala Gln Ser Ala Asn Leu Thr Asp Lys
            260                 265                 270

```
Glu Leu Glu Ala Phe Arg Glu Leu Lys His Phe Glu Ala Lys Ile
        275                 280                 285

Glu Lys His Asn His Tyr Gln Lys Gln Leu Glu Ile Ala His Glu Lys
        290                 295                 300

Leu Arg His Ala Glu Ser Val Gly Asp Gly Arg Val Ser Arg Ser
305                 310                 315                 320

Arg Glu Lys His Ala Leu Leu Glu Gly Arg Thr Lys Glu Leu Gly Tyr
                325                 330                 335

Thr Val Lys Lys His Leu Gln Asp Leu Ser Gly Arg Ile Ser Arg Ala
                340                 345                 350

Arg His Asn Glu Leu
        355

<210> SEQ ID NO 22
<211> LENGTH: 378
<212> TYPE: PRT
<213> ORGANISM: Mus musculus

<400> SEQUENCE: 22

Met Gly Gly Pro Thr Arg Pro Ser Pro Val Ser Leu Leu Ala Leu Gln
1               5                   10                  15

Arg Lys Met Ala Pro Arg Arg Glu Arg Val Ser Thr Leu Pro Arg Leu
            20                  25                  30

Gln Leu Leu Val Leu Leu Leu Pro Leu Met Leu Val Pro Gln Pro
        35                  40                  45

Ile Ala Gly His Gly Gly Lys Tyr Ser Arg Glu Lys Asn Glu Pro Glu
    50                  55                  60

Met Ala Ala Lys Arg Glu Ser Gly Glu Glu Phe Arg Met Glu Lys Leu
65                  70                  75                  80

Asn Gln Leu Trp Glu Lys Ala Lys Arg Leu His Leu Ser Pro Val Arg
                85                  90                  95

Leu Ala Glu Leu His Ser Asp Leu Lys Ile Gln Glu Arg Asp Glu Leu
            100                 105                 110

Asn Trp Lys Lys Leu Lys Val Glu Gly Leu Asp Lys Asp Gly Glu Lys
        115                 120                 125

Glu Ala Lys Leu Ile His Asn Leu Asn Val Ile Leu Ala Arg Tyr Gly
    130                 135                 140

Leu Asp Gly Arg Lys Asp Ala Gln Met Val His Ser Asn Ala Leu Asn
145                 150                 155                 160

Glu Asp Thr Gln Asp Glu Leu Gly Asp Pro Arg Leu Glu Lys Leu Trp
                165                 170                 175

His Lys Ala Lys Thr Ser Gly Lys Phe Ser Ser Glu Glu Leu Asp Lys
            180                 185                 190

Leu Trp Arg Glu Phe Leu His Tyr Lys Glu Lys Ile Gln Glu Tyr Asn
        195                 200                 205

Val Leu Leu Asp Thr Leu Ser Arg Ala Glu Glu Gly Tyr Glu Asn Leu
    210                 215                 220

Leu Ser Pro Ser Asp Met Ala His Ile Lys Ser Asp Thr Leu Ile Ser
225                 230                 235                 240

Lys His Ser Glu Leu Lys Asp Arg Leu Arg Ser Ile Asn Gln Gly Leu
                245                 250                 255

Asp Arg Leu Arg Lys Val Ser His Gln Gly Tyr Gly Ser Thr Thr Glu
            260                 265                 270

Phe Glu Glu Pro Arg Val Ile Asp Leu Trp Asp Leu Ala Gln Ser Ala
        275                 280                 285
```

```
Asn Phe Thr Glu Lys Glu Leu Glu Ser Phe Arg Glu Glu Leu Lys His
            290                 295                 300

Phe Glu Ala Lys Ile Glu Lys His Asn His Tyr Gln Lys Gln Leu Glu
305                 310                 315                 320

Ile Ser His Gln Lys Leu Lys His Val Glu Ser Ile Gly Asp Pro Glu
                325                 330                 335

His Ile Ser Arg Asn Lys Glu Lys Tyr Val Leu Leu Glu Glu Lys Thr
            340                 345                 350

Lys Glu Leu Gly Tyr Lys Val Lys Lys His Leu Gln Asp Leu Ser Ser
                355                 360                 365

Arg Val Ser Arg Ala Arg His Asn Glu Leu
            370                 375

<210> SEQ ID NO 23
<211> LENGTH: 357
<212> TYPE: PRT
<213> ORGANISM: Rat

<400> SEQUENCE: 23

Leu Arg Asp Arg Val Ser Thr Leu Pro Arg Leu Gln Leu Leu Val Leu
1               5                   10                  15

Leu Leu Leu Pro Leu Leu Val Pro Gln Pro Ile Ala Gly His Gly
            20                  25                  30

Gly Lys Tyr Ser Arg Glu Lys Asn Glu Pro Glu Met Ala Ala Lys Arg
                35                  40                  45

Glu Ser Gly Glu Glu Phe Arg Met Glu Lys Leu Asn Gln Leu Trp Glu
50                  55                  60

Lys Ala Lys Arg Leu His Leu Ser Pro Val Arg Leu Ala Glu Leu His
65                  70                  75                  80

Ser Asp Leu Lys Ile Gln Glu Arg Asp Glu Leu Asn Trp Lys Lys Leu
                85                  90                  95

Lys Val Glu Gly Leu Asp Gly Asp Gly Glu Lys Glu Ala Lys Leu Val
            100                 105                 110

His Asn Leu Asn Val Ile Leu Ala Arg Tyr Gly Leu Asp Gly Arg Lys
            115                 120                 125

Asp Thr Gln Thr Val His Ser Asn Ala Leu Asn Glu Asp Thr Gln Asp
130                 135                 140

Glu Leu Gly Asp Pro Arg Leu Glu Lys Leu Trp His Lys Ala Lys Thr
145                 150                 155                 160

Ser Gly Lys Phe Ser Ser Glu Glu Leu Asp Lys Leu Trp Arg Glu Phe
                165                 170                 175

Leu His Tyr Lys Glu Lys Ile His Glu Tyr Asn Val Leu Leu Asp Thr
            180                 185                 190

Leu Ser Arg Ala Glu Glu Gly Tyr Glu Asn Leu Leu Ser Pro Ser Asp
            195                 200                 205

Met Thr His Ile Lys Ser Asp Thr Leu Ala Ser Lys His Ser Glu Leu
210                 215                 220

Lys Asp Arg Leu Arg Ser Ile Asn Gln Gly Leu Asp Arg Leu Arg Lys
225                 230                 235                 240

Val Ser His Gln Gly Tyr Gly Pro Ala Thr Glu Phe Glu Glu Pro Arg
                245                 250                 255

Val Ile Asp Leu Trp Asp Leu Ala Gln Ser Ala Asn Phe Thr Glu Lys
            260                 265                 270

Glu Leu Glu Ser Phe Arg Glu Glu Leu Lys His Phe Glu Ala Lys Ile
```

```
                275                 280                 285
Glu Lys His Asn His Tyr Gln Lys Gln Leu Glu Ile Ser His Gln Lys
    290                 295                 300
Leu Lys His Val Glu Ser Ile Gly Asp Pro Glu His Ile Ser Arg Asn
305                 310                 315                 320
Lys Glu Lys Tyr Val Leu Leu Glu Glu Lys Thr Lys Glu Leu Gly Tyr
                325                 330                 335
Lys Val Lys Lys His Leu Gln Asp Leu Ser Ser Arg Val Ser Arg Ala
            340                 345                 350
Arg His Asn Glu Leu
        355

<210> SEQ ID NO 24
<211> LENGTH: 348
<212> TYPE: PRT
<213> ORGANISM: Chicken

<400> SEQUENCE: 24

Met Gly Ala Thr Arg Thr Leu Val Ala Val Met Ala Ala Phe Leu Ala
1               5                   10                  15
Val Ser Thr Arg Ala Ser Lys Tyr Thr Arg Glu Ala Asn Glu Gly Leu
                20                  25                  30
Ala Asp Ala Lys Arg Arg Glu Ala Gly Glu Phe Arg Val Val Arg Leu
            35                  40                  45
Asn Gln Val Trp Glu Lys Ala Gln Arg Leu Gln Leu Ser Ala Val Lys
    50                  55                  60
Leu Ala Glu Leu His Ser Asp Leu Lys Ile Gln Glu Lys Asp Glu Leu
65                  70                  75                  80
Ser Trp Lys Lys Leu Lys Ala Glu Gly Leu Gly Glu Asp Gly Glu Lys
                85                  90                  95
Glu Ala Lys Leu Arg Arg Asn Ile Asn Val Ile Met Thr Lys Tyr Gly
            100                 105                 110
Met Asn Gly Lys Lys Asp Ser His Leu Thr Asp Thr Asn Tyr Ile Lys
        115                 120                 125
Asp Gly Thr Glu Ser Asp Thr Leu Asp Asp Pro Arg Leu Glu Lys Leu
    130                 135                 140
Trp Ser Lys Ala Lys Thr Ser Gly Lys Phe Ser Asp Glu Glu Leu Asp
145                 150                 155                 160
Lys Leu Trp Arg Glu Phe Lys His His Lys Glu Lys Ile Arg Glu Tyr
                165                 170                 175
Asn Ile Leu Leu Glu Thr Val Ser Arg Thr Glu Asp Ile His Lys Lys
            180                 185                 190
Val Ile Asn Pro Ser Glu Glu Asn Pro Val Lys Glu Glu Val Leu His
        195                 200                 205
Asn Lys His Arg Glu Leu Lys Glu Lys Leu Arg Ser Ile Asn Gln Gly
    210                 215                 220
Phe Glu Arg Leu Arg Lys Val Ser His Gln Gly Tyr Asp Ala Thr Ser
225                 230                 235                 240
Glu Phe Glu Glu Pro Arg Val Ile Asp Leu Trp Asp Met Ala Lys Ser
                245                 250                 255
Ala Asn Phe Thr Glu Lys Glu Leu Glu Ser Phe Arg Glu Glu Leu Lys
            260                 265                 270
His Phe Glu Ala Lys Ile Glu Lys His His Tyr Gln Lys Gln Leu
        275                 280                 285
```

```
Glu Ile Ser His Glu Lys Leu Lys His Ile Glu Gly Thr Gly Asp Lys
    290                 295                 300

Glu His Leu Asn Arg Asn Arg Glu Lys Tyr Ala Met Leu Glu Glu Lys
305                 310                 315                 320

Thr Lys Glu Leu Gly Tyr Lys Val Lys His Leu Gln Asp Leu Ser
                325                 330                 335

Ser Arg Ile Ser Gln Gly Leu Gln His Asn Glu Leu
                340                 345

<210> SEQ ID NO 25
<211> LENGTH: 331
<212> TYPE: PRT
<213> ORGANISM: Zebrafish

<400> SEQUENCE: 25

Met Ala Gly Lys Tyr Ser Lys Glu Met Asn Glu Lys Asn Ala Ser Asp
1               5                   10                  15

Lys Ser Asn Asn Gln Val Glu Phe Arg Ile Ala Lys Leu Asn Gln Val
                20                  25                  30

Trp Glu Lys Ala Ile Arg Met Gln Leu Ala Pro Val Arg Leu Ser Glu
            35                  40                  45

Leu His Ser Asp Leu Lys Ile Gln Glu Lys Asp Glu Leu Gln Trp Lys
    50                  55                  60

Lys Leu Lys Ala Glu Gly Met Asp Glu Asp Gly Arg Glu Ala Lys
65                  70                  75                  80

Leu Arg Arg Asn Phe Asn Ile Ile Leu Ala Lys Tyr Gly Met Asp Gly
                85                  90                  95

Lys Lys Asp Thr Arg Thr Leu Asp Ser Asn Arg Leu Lys Asp His Glu
                100                 105                 110

Val Lys Ile Gly Asp Thr Phe Asp Asp Pro Lys Leu Asp Lys Leu Trp
            115                 120                 125

Asn Lys Ala Arg Thr Ser Gly Lys Phe Ser Asp Glu Glu Leu Gln Thr
    130                 135                 140

Leu His Arg Glu Phe Gln His His Lys Asp Lys Ile His Glu Tyr Asn
145                 150                 155                 160

Ile Val Met Asp Thr Val Ser Arg Thr Glu Glu Ile His Lys Asn Val
                165                 170                 175

Ile Ser Pro Leu Glu Gly Asp Val Lys Glu Asn Val Leu His Gln Lys
                180                 185                 190

His Thr Asp Leu Lys Gln Arg Met Arg Asp Leu Asn Gln Gly Phe Glu
            195                 200                 205

Arg Leu Arg Lys Ile Thr His Glu Gly Tyr Thr Asp Asp Ser Glu Phe
    210                 215                 220

Arg Glu Pro Arg Val Ile Glu Leu Trp Glu Met Ala Lys Arg Ser Asn
225                 230                 235                 240

Leu Ser Glu Asp Glu Leu Asp Ser Leu Lys Glu Leu Arg His Phe
                245                 250                 255

Glu Thr Lys Val Glu Lys His Gln His Tyr Gln Glu Gln Leu Glu Leu
                260                 265                 270

Ser His Gln Lys Leu Lys His Val Glu Ala Leu Gly Asp Glu Asp His
            275                 280                 285

Ile Met Arg Asn Lys Glu Lys Tyr Asn Thr Leu Ala Glu Lys Ala Arg
    290                 295                 300

Glu Met Gly Tyr Lys Met Lys Lys His Leu Gln Asp Leu Thr Asn Lys
305                 310                 315                 320
```

Leu Ser Lys Asn Gly Leu Gln His Asn Glu Leu
                325                 330

<210> SEQ ID NO 26
<211> LENGTH: 379
<212> TYPE: PRT
<213> ORGANISM: Fruit fly

<400> SEQUENCE: 26

Met Val Arg Ser Ala Leu Val Val Ala Ala Ile Ala Leu Ser Val Leu
1               5                   10                  15

Ile Ala Leu Gln Gly Val Asp Ala Asp Lys Lys Gln Ser Lys Lys Tyr
            20                  25                  30

Ser Lys Glu Ala Asn Asp Pro His Phe Gln Val Lys Gln Glu Lys
        35                  40                  45

Tyr Asp Pro Asp Phe Lys Ser Ile Gln Arg Pro Phe Arg Met Ala Lys
    50                  55                  60

Leu Asn Leu Val Trp Ala Lys Ala Gln Asn Arg Leu Thr Glu Pro Lys
65                  70                  75                  80

Leu Lys Ser Leu Tyr Met Glu Leu Lys Ile His Asp Lys Glu Ile
                85                  90                  95

Ala Trp Lys Gln Leu Asn Ser Gln His Lys Asp Lys Asp Gly Leu Lys
            100                 105                 110

Ala Asp Glu Leu Arg Arg Lys Leu Ile Gly Ile Met Ser Ser Tyr Asp
        115                 120                 125

Leu Leu Glu His Phe Asp Asp Thr Gln Asp Thr Glu Lys Leu Lys Pro
    130                 135                 140

Tyr Lys Lys Phe His Asp Ala Glu Glu Arg His Arg Asn Lys Ser Leu
145                 150                 155                 160

Phe Lys Asp Lys Lys Leu Asn Arg Leu Trp Glu Lys Ala Glu Ile Ser
                165                 170                 175

Gly Phe Thr Ala Glu Glu Leu Lys Ser Leu Lys Gln Glu Phe Asp His
            180                 185                 190

His Gln Asp Lys Val Asp Val Tyr Tyr Ser Leu Leu Glu Asn Ile Gly
        195                 200                 205

Thr Val Asp Thr Asp Lys His Glu Asn Ala Ile Asn Thr Glu Asp Leu
    210                 215                 220

Asp Thr Tyr Asn Leu Ile Ser Asn Asp Val Asn Glu Asn Asp Ile Lys
225                 230                 235                 240

Thr His Ala Gln Asn Val Lys Ser Phe Glu Asn Asp Leu Asn Thr Leu
                245                 250                 255

Arg Gly His His Thr Gly Ile Lys Asp His Tyr Asp Arg Leu Glu Arg
            260                 265                 270

Leu Val Ser Ser Gly Pro His Ser Gln Asp Phe Ile Glu Pro Lys Val
        275                 280                 285

Gln Gly Leu Trp Arg Val Ala Gln Ala Ser Asn Phe Thr Val Lys Glu
    290                 295                 300

Leu Glu Ser Ile Lys Thr Glu Leu His His Phe Glu Ser Arg Leu Leu
305                 310                 315                 320

Lys Leu Arg His Leu His Ala Glu His Ala Leu Gln Lys Glu Lys Tyr
                325                 330                 335

Lys Gly Glu Lys Val Lys Asp Lys Ser Ser Arg Phe Glu Glu Met Glu
            340                 345                 350

Asp Gln Leu Lys Lys Gln Thr Arg Lys Val Glu Lys Leu Gln Glu Asn

```
                    355                 360                 365
Ile Glu Lys Thr Ile Phe Lys His Thr Glu Leu
    370                 375

<210> SEQ ID NO 27
<211> LENGTH: 400
<212> TYPE: PRT
<213> ORGANISM: Mosquito

<400> SEQUENCE: 27

Glu Leu Cys Pro Ile Ala Arg Arg Lys Arg Gly Ile Lys His Thr Leu
1               5                   10                  15

Thr Met Pro Leu Phe Thr Arg Leu Cys Val Ile Val Phe Thr Val Leu
            20                  25                  30

Val Cys Asn His Val Val Gln Ser Glu Lys Ala His Ser Lys Tyr Ser
        35                  40                  45

Lys His Ala Asn Ala Leu Pro Asp Ser Glu Ile Tyr Glu Pro Asp Phe
    50                  55                  60

Arg Asn Ile Gln Arg Pro Phe Arg Met Ala Lys Leu Asn Leu Val Trp
65                  70                  75                  80

Thr Lys Ala Gln His Arg Leu Thr Glu Pro Lys Leu Lys Ser Leu Tyr
                85                  90                  95

Thr Glu Leu Lys Leu His Asp Lys Glu Leu Thr Tyr Lys Gln Leu
            100                 105                 110

Lys Glu Lys Asp Lys Asp Gly Leu Lys Glu Ala Glu Leu Arg Asn Lys
        115                 120                 125

Leu Val Ser Ile Met Ser Thr Tyr Gly Leu Leu Glu His Phe Asp Asp
    130                 135                 140

Thr Gln Asp Pro Glu Lys Tyr Lys Leu Ala Lys Ser Ser Asp Gly Ala
145                 150                 155                 160

Pro Lys Lys Asp Thr Tyr Lys Asn Lys Ser Leu Phe Lys Asp Lys Lys
                165                 170                 175

Leu Asn Lys Leu Trp Asp Lys Ala Glu Ser Ala Gly Phe Thr Lys Glu
            180                 185                 190

Glu Leu Asp Ala Leu Arg Glu Glu Phe Asp His His Gln Ala Lys Ile
        195                 200                 205

Asp Val Tyr Tyr Ser Leu Leu Glu Arg Leu Gly Asp Asp Asp Gly
    210                 215                 220

Gly Ala Ala Gly Gln Gly Ser Arg Arg Asp Asp Asp Ala Leu Leu Asn
225                 230                 235                 240

Ala Val Asn Asp Glu Glu His Asp Arg Tyr Asn Glu Val Asp Arg Ala
                245                 250                 255

Glu Glu Thr Asp Arg Ser Gln Pro Gly Ala Asn Lys Gln His Ala Tyr
            260                 265                 270

Leu His Lys Ser Asn Gln Leu Arg Glu Lys His Arg Glu Ile Arg Asp
        275                 280                 285

Asn Phe Asp Arg Leu Asp Arg Ile Ala Ser Lys Gly Pro Lys Ser Gln
    290                 295                 300

Asp Phe Val Glu Pro Lys Val Gln Gly Leu Trp Arg Val Ala Leu Ala
305                 310                 315                 320

Ser Asp Phe Ser Ala Asp Glu Leu Ala Ser Leu Lys Val Glu Leu Leu
                325                 330                 335

His Tyr Glu Ser Arg Leu Leu Lys Leu Arg His Met His Ala Glu His
            340                 345                 350
```

```
Ala Leu Ser Leu Glu Lys His Lys His Ser Asp Ala Lys Ala Asp Thr
        355                 360                 365

His Lys Leu Met Glu Asp Asn Ile Lys Lys Gln Thr Arg Lys Val Glu
    370                 375                 380

Lys Met Gln Glu Glu Val Glu Arg Arg Ile Phe Lys His Ser Glu Leu
385                 390                 395                 400

<210> SEQ ID NO 28
<211> LENGTH: 331
<212> TYPE: PRT
<213> ORGANISM: Flatworm

<400> SEQUENCE: 28

Met Arg Asn His Phe Ser Phe Leu Leu Phe Leu Leu Val Ile Gly Ser
1               5                   10                  15

Ala His Asn Lys Lys Thr Gln Tyr Arg Thr Glu Arg Ile Asn Phe Ile
            20                  25                  30

Tyr Glu Lys Ala Leu Gln His Val Thr Asp Arg Gln Asn Leu Ala Arg
        35                  40                  45

Leu Glu Lys Glu Leu Ser Gly Tyr Asp Ala Ile Tyr Leu Ala Ser Lys
    50                  55                  60

Ser Asn Arg Gln Gly Thr Gln Gly Thr Lys Glu Ile Asp Lys Ile Asp
65                  70                  75                  80

Asp Lys Leu Gly Lys Ile Leu Glu Lys Tyr Gly Leu Glu Lys Ala Val
                85                  90                  95

Leu Ala Phe Lys Glu Lys Tyr Lys His Lys Asn Leu Phe Gln Gln Thr
            100                 105                 110

Asp Asp Asn Glu Pro Leu Pro Ser Gly Lys Phe Thr Asp Gln Asn Leu
        115                 120                 125

Gln Lys Leu Trp Ser Gln Ala Gln Asn Gly Lys Phe Ser Gln Lys Glu
    130                 135                 140

Leu Asn Ala Leu His Gly Glu Leu Lys Glu Val Glu Gln Lys Met Arg
145                 150                 155                 160

Val Tyr Glu Asp Gln Leu Asp Asp Phe Lys Lys Val Pro His Glu Asn
                165                 170                 175

Ser Ile Gln His Asp Ile Glu Ser Ile Gly Asp Lys Thr Lys Lys Leu
            180                 185                 190

Lys Ala Ala Asn Arg Glu Leu Asn Asp His Leu Asp Glu Val His Arg
        195                 200                 205

Lys Val Thr Ser Glu Glu Phe Ser Pro Phe Asn Glu Pro Arg Val Lys
    210                 215                 220

Arg Leu Trp Lys Leu Ala Gln Glu Asn Glu Lys Leu Thr Pro His Glu
225                 230                 235                 240

Leu Ser Val Leu Lys Asp Glu Leu Ser His Phe Glu Ser Gln Leu Lys
                245                 250                 255

Lys Ile Glu Phe His Lys Val Phe Phe Val Ala Asn Ser Cys Pro
            260                 265                 270

Lys Arg Gly Lys Asn Glu Glu Val Ser Arg Leu Gln Glu Asp Ala Glu
        275                 280                 285

Glu Arg Gly Lys Asp Lys Ser Gln Val Tyr Glu Asn Leu Glu Leu Ser
    290                 295                 300
```

```
-continued

Ile Lys His Glu Lys Leu Asn Arg Lys Ala Arg Lys Leu Glu Lys Tyr
305                 310                 315                 320

Ile Glu Glu Lys Ile Ile Ile His Arg Glu Leu
                325                 330
```